United States Patent [19]
Yonemura et al.

[11] Patent Number: 5,693,499
[45] Date of Patent: Dec. 2, 1997

[54] PROCESS FOR PREPARING HUMAN COAGULATION FACTOR VIII PROTEIN COMPLEX

[75] Inventors: Hiroshi Yonemura; Yoshitaka Tajima; Keishin Sugawara, all of Kumamoto; Kenichi Masuda, Hachioji, all of Japan

[73] Assignees: Juridical Foundation The Chemo-Sero Therapeutic Research Institute, Kumamoto; Teijin Limited, Osaka, both of Japan

[21] Appl. No.: 276,594

[22] Filed: Jul. 18, 1994

Related U.S. Application Data

[63] Continuation of Ser. No. 950,191, Sep. 24, 1992, abandoned.

[30] Foreign Application Priority Data

Sep. 24, 1991 [JP] Japan .................................. 3-243262

[51] Int. Cl.[6] .............................. C12N 5/10; C12N 15/12; C12N 15/63; C12N 15/79
[52] U.S. Cl. .................. 435/69.6; 435/240.2; 435/320.1; 530/383; 536/23.5
[58] Field of Search .......................... 435/69.6, 320.1, 435/172.3, 240.2, 252.3, 69.8; 530/383; 930/100; 536/23.5

[56] References Cited

U.S. PATENT DOCUMENTS 4,980,456  12/1990  Scandella et al. .................. 530/383
5,004,803  4/1991  Kaufman et al. .................. 530/383

FOREIGN PATENT DOCUMENTS 0232112  8/1987  European Pat. Off. .
8800831  2/1988  WIPO .
9107490  5/1991  WIPO .

OTHER PUBLICATIONS

Robson et al. 1986, Introduction to Protein Engineering, Elsevier, New York, p. 41.

Fay, P.J. 1988, Archives of Biochem and Biophys. 262(2)525–531.

R.L. Burke et al., "The Functional Domains of Coagulation Factor VIII:C", The Journal of Biological Chemistry, vol. 261, No. 27, 25 Sep. 1986, Baltimore, Maryland, pp. 12574–12578.

Primary Examiner—Dian C. Jacobson
Attorney, Agent, or Firm—Foley & Lardner

[57] ABSTRACT

A plasmid for expression of human coagulation factor VIII H-chain, a plasmid for expression of human coagulation factor VIII L-chain, an animal cell transformed with either said H-chain expression plasmid or said L-chain expression plasmid or with both thereof, and a process for preparing a human coagulation factor VIII protein complex which comprises forming a transformed animal cell by introducing both said H-chain expression plasmid and said L-chain expression plasmid into said animal cell, culturing said cell to produce the human coagulation factor VIII protein complex in the culture medium and collecting the same. The process of the present invention allows for the production of a safe factor VIII at a high expression level applicable for the production of Factor VIII on an industrial scale.

11 Claims, 12 Drawing Sheets

PROCESS FOR PREPARING HUMAN COAGULATION FACTOR VIII PROTEIN COMPLEX

This application is a continuation of U.S. application Ser. No. 07/950,191 filed Sep. 24, 1992, now abandoned.

The present invention relates to an expression of a human coagulation factor VIII (hereinafter referred to as "Factor VIII"), and to a process for preparing a novel Factor VIII protein complex having a coagulation activity, said process being capable of obtaining a large amount of said protein complex, a plasmid for expression of Factor VIII and a transformed cell used in said process. More particularly, the present invention relates to a plasmid for expression of a heavy chain (hereinafter referred to as "H-chain") or a light chain (hereinafter referred to as "L-chain") protein of Factor VIII in a separate cistron or for expression of an active complex of said H-chain and L-chain proteins in a large amount, to a transformed cell obtained by introducing said expression plasmid(s) into a suitable animal cell, and to a process for effectively preparing Factor VIII using said expression plasmid and transformed cell.

PRIOR ART

Human Factor VIII is a plasma protein involved in the intrinsic pathway of blood coagulation and acts as a coenzyme for promoting the activation of Factor X by the activated Factor IX. Factor VIII, forming a complex with von Willebrand factor in vivo, circulates in blood.

Factor VIII has the following nucleotide and amino acid sequences (SEQ ID NOS 1 and 2 respectively):

```
GCC ACC AGA AGA TAC TAC CTG GGT GCA GTG GAA CTG TCA TGG GAC TAT
Ala Thr Arg Arg Tyr Tyr Leu Gly Ala Val Glu Leu Ser Trp Asp Tyr
 1           5                   10                  15

ATG CAA AGT GAT CTC GGT GAG CTG CCT GTG GAC GCA AGA TTT CCT CCT
Met Gln Ser Asp Leu Gly Glu Leu Pro Val Asp Ala Arg Phe Pro Pro
            20                  25                  30

AGA GTG CCA AAA TCT TTT CCA TTC AAC ACC TCA GTC GTG TAC AAA AAG
Arg Val Pro Lys Ser Phe Pro Phe Asn Thr Ser Val Val Tyr Lys Lys
        35                  40                  45

ACT CTG TTT GTA GAA TTC ACG GAT CAC CTT TTC AAC ATC GCT AAG CCA
Thr Leu Phe Val Glu Phe Thr Asp His Leu Phe Asn Ile Ala Lys Pro
    50                  55                  60

AGG CCA CCC TGG ATG GGT CTG CTA GGT CCT ACC ATC CAG GCT GAG GTT
Arg Pro Pro Trp Met Gly Leu Leu Gly Pro Thr Ile Gln Ala Glu Val
65              70                  75                      80

TAT GAT ACA GTG GTC ATT ACA CTT AAG AAC ATG GCT TCC CAT CCT GTC
Tyr Asp Thr Val Val Ile Thr Leu Lys Asn Met Ala Ser His Pro Val
                85                  90                  95

AGT CTT CAT GCT GTT GGT GTA TCC TAC TGG AAA GCT TCT GAG GGA GCT
Ser Leu His Ala Val Gly Val Ser Tyr Trp Lys Ala Ser Glu Gly Ala
            100                 105                 110

GAA TAT GAT GAT CAG ACC AGT CAA AGG GAG AAA GAA GAT GAT AAA GTC
Glu Tyr Asp Asp Gln Thr Ser Gln Arg Glu Lys Glu Asp Asp Lys Val
        115                 120                 125

TTC CCT GGT GGA AGC CAT ACA TAT GTC TGG CAG GTC CTG AAA GAG AAT
Phe Pro Gly Gly Ser His Thr Tyr Val Trp Gln Val Leu Lys Glu Asn
    130                 135                 140

GGT CCA ATG GCC TCT GAC CCA CTG TGC CTT ACC TAC TCA TAT CTT TCT
Gly Pro Met Ala Ser Asp Pro Leu Cys Leu Thr Tyr Ser Tyr Leu Ser
145                 150                 155                 160

CAT GTG GAC CTG GTA AAA GAC TTG AAT TCA GGC CTC ATT GGA GCC CTA
His Val Asp Leu Val Lys Asp Leu Asn Ser Gly Leu Ile Gly Ala Leu
                165                 170                 175

CTA GTA TGT AGA GAA GGG AGT CTG GCC AAG GAA AAG ACA CAG ACC TTG
Leu Val Cys Arg Glu Gly Ser Leu Ala Lys Glu Lys Thr Gln Thr Leu
            180                 185                 190

CAC AAA TTT ATA CTA CTT TTT GCT GTA TTT GAT GAA GGG AAA AGT TGG
His Lys Phe Ile Leu Leu Phe Ala Val Phe Asp Glu Gly Lys Ser Trp
        195                 200                 205

CAC TCA GAA ACA AAG AAC TCC TTG ATG CAG GAT AGG GAT GCT GCA TCT
His Ser Glu Thr Lys Asn Ser Leu Met Gln Asp Arg Asp Ala Ala Ser
    210                 215                 220

GCT CGG GCC TGG CCT AAA ATG CAC ACA GTC AAT GGT TAT GTA AAC AGG
Ala Arg Ala Trp Pro Lys Met His Thr Val Asn Gly Tyr Val Asn Arg
225                 230                 235                 240
```

```
TCT CTG CCA GGT CTG ATT GGA TGC CAC AGG AAA TCA GTC TAT TGG CAT
Ser Leu Pro Gly Leu Ile Gly Cys His Arg Lys Ser Val Tyr Trp His
            245                 250                 255

GTG ATT GGA ATG GGC ACC ACT CCT GAA GTG CAC TCA ATA TTC CTC GAA
Val Ile Gly Met Gly Thr Thr Pro Glu Val His Ser Ile Phe Leu Glu
            260                 265                 270

GGT CAC ACA TTT CTT GTG AGG AAC CAT CGC CAG GCG TCC TTG GAA ATC
Gly His Thr Phe Leu Val Arg Asn His Arg Gln Ala Ser Leu Glu Ile
            275                 280                 285

TCG CCA ATA ACT TTC CTT ACT GCT CAA ACA CTC TTG ATG GAC CTT GGA
Ser Pro Ile Thr Phe Leu Thr Ala Gln Thr Leu Leu Met Asp Leu Gly
    290                 295                 300

CAG TTT CTA CTG TTT TGT CAT ATC TCT TCC CAC CAA CAT GAT GGC ATG
Gln Phe Leu Leu Phe Cys His Ile Ser Ser His Gln His Asp Gly Met
305                 310                 315                 320

GAA GCT TAT GTC AAA GTA GAC AGC TGT CCA GAG GAA CCC CAA CTA CGA
Glu Ala Tyr Val Lys Val Asp Ser Cys Pro Glu Glu Pro Gln Leu Arg
                325                 330                 335

ATG AAA AAT AAT GAA GAA GCG GAA GAC TAT GAT GAT GAT CTT ACT GAT
Met Lys Asn Asn Glu Glu Ala Glu Asp Tyr Asp Asp Asp Leu Thr Asp
            340                 345                 350

TCT GAA ATG GAT GTG GTC AGG TTT GAT GAT GAC AAC TCT CCT TCC TTT
Ser Glu Met Asp Val Val Arg Phe Asp Asp Asp Asn Ser Pro Ser Phe
        355                 360                 365

ATC CAA ATT CGC TCA GTT GCC AAG AAG CAT CCT AAA ACT TGG GTA CAT
Ile Gln Ile Arg Ser Val Ala Lys Lys His Pro Lys Thr Trp Val His
    370                 375                 380

TAC ATT GCT GCT GAA GAG GAG GAC TGG GAC TAT GCT CCC TTA GTC CTC
Tyr Ile Ala Ala Glu Glu Glu Asp Trp Asp Tyr Ala Pro Leu Val Leu
385                 390                 395                 400

GCC CCC GAT GAC AGA AGT TAT AAA AGT CAA TAT TTG AAC AAT GGC CCT
Ala Pro Asp Asp Arg Ser Tyr Lys Ser Gln Tyr Leu Asn Asn Gly Pro
                405                 410                 415

CAG CGG ATT GGT AGG AAG TAC AAA AAA GTC CGA TTT ATG GCA TAC ACA
Gln Arg Ile Gly Arg Lys Tyr Lys Lys Val Arg Phe Met Ala Tyr Thr
            420                 425                 430

GAT GAA ACC TTT AAG ACT CGT GAA GCT ATT CAG CAT GAA TCA GGA ATC
Asp Glu Thr Phe Lys Thr Arg Glu Ala Ile Gln His Glu Ser Gly Ile
        435                 440                 445

TTG GGA CCT TTA CTT TAT GGG GAA GTT GGA GAC ACA CTG TTG ATT ATA
Leu Gly Pro Leu Leu Tyr Gly Glu Val Gly Asp Thr Leu Leu Ile Ile
    450                 455                 460

TTT AAG AAT CAA GCA AGC AGA CCA TAT AAC ATC TAC CCT CAC GGA ATC
Phe Lys Asn Gln Ala Ser Arg Pro Tyr Asn Ile Tyr Pro His Gly Ile
465                 470                 475                 480

ACT GAT GTC CGT CCT TTG TAT TCA AGG AGA TTA CCA AAA GGT GTA AAA
Thr Asp Val Arg Pro Leu Tyr Ser Arg Arg Leu Pro Lys Gly Val Lys
                485                 490                 495

CAT TTG AAG GAT TTT CCA ATT CTG CCA GGA GAA ATA TTC AAA TAT AAA
His Leu Lys Asp Phe Pro Ile Leu Pro Gly Glu Ile Phe Lys Tyr Lys
            500                 505                 510

TGG ACA GTG ACT GTA GAA GAT GGG CCA ACT AAA TCA GAT CCT CGG TGC
Trp Thr Val Thr Val Glu Asp Gly Pro Thr Lys Ser Asp Pro Arg Cys
        515                 520                 525

CTG ACC CGC TAT TAC TCT AGT TTC CTT AAT ATG GAG AGA GAT CTA GCT
Leu Thr Arg Tyr Tyr Ser Ser Phe Val Asn Met Glu Arg Asp Leu Ala
    530                 535                 540

TCA GGA CTC ATT GGC CCT CTC CTC ATC TGC TAC AAA GAA TCT GTA GAT
Ser Gly Leu Ile Gly Pro Leu Leu Ile Cys Tyr Lys Glu Ser Val Asp
545                 550                 555                 560

CAA AGA GGA AAC CAG ATA ATG TCA GAC AAG AGG AAT GTC ATC CTG TTT
Gln Arg Gly Asn Gln Ile Met Ser Asp Lys Arg Asn Val Ile Leu Phe
                565                 570                 575
```

```
TCT GTA TTT GAT GAG AAC CGA AGC TGG TAC CTC ACA GAG AAT ATA CAA
Ser Val Phe Asp Glu Asn Arg Ser Trp Tyr Leu Thr Glu Asn Ile Gln
            580                 585                 590

CGC TTT CTC CCC AAT CCA GCT GGA GTG CAG CTT GAG GAT CCA GAG TTC
Arg Phe Leu Pro Asn Pro Ala Gly Val Gln Leu Glu Asp Pro Glu Phe
        595                 600                 605

CAA GCC TCC AAC ATC ATG CAC AGC ATC AAT GGC TAT GTT TTT GAT AGT
Gln Ala Ser Asn Ile Met His Ser Ile Asn Gly Tyr Val Phe Asp Ser
        610                 615                 620

TTG CAG TTG TCA GTT TGT TTG CAT GAG GTG GCA TAC TGG TAC ATT CTA
Leu Gln Leu Ser Val Cys Leu His Glu Val Ala Tyr Trp Tyr Ile Leu
625                 630                 635                 640

AGC ATT GGA GCA CAG ACT GAC TTC CTT TCT GTC TTC TTC TCT GGA TAT
Ser Ile Gly Ala Gln Thr Asp Phe Leu Ser Val Phe Phe Ser Gly Tyr
            645                 650                 655

ACC TTC AAA CAC AAA ATG GTC TAT GAA GAC ACA CTC ACC CTA TTC CCA
Thr Phe Lys His Lys Met Val Tyr Glu Asp Thr Leu Thr Leu Phe Pro
            660                 665                 670

TTC TCA GGA GAA ACT GTC TTC ATG TCG ATG GAA AAC CCA GGT CTA TGG
Phe Ser Gly Glu Thr Val Phe Met Ser Met Glu Asn Pro Gly Leu Trp
        675                 680                 685

ATT CTG GGG TGC CAC AAC TCA GAC TTT CGG AAC AGA GGC ATG ACC GCC
Ile Leu Gly Cys His Asn Ser Asp Phe Arg Asn Arg Gly Met Thr Ala
        690                 695                 700

TTA CTG AAG GTT TCT AGT TGT GAC AAG AAC ACT GGT GAT TAT TAC GAG
Leu Leu Lys Val Ser Ser Cys Asp Lys Asn Thr Gly Asp Tyr Tyr Glu
705                 710                 715                 720

GAC AGT TAT GAA GAT ATT TCA GCA TAC TTG CTG AGT AAA AAC AAT GCC
Asp Ser Tyr Glu Asp Ile Ser Ala Tyr Leu Leu Ser Lys Asn Asn Ala
                725                 730                 735

ATT GAA CCA AGA AGC TTC TCC CAG AAT TCA AGA CAC CGT AGC ACT AGG
Ile Glu Pro Arg Ser Phe Ser Gln Asn Ser Arg His Arg Ser Thr Arg
            740                 745                 750

CAA AAG CAA TTT AAT GCC ACC ACA ATT CCA GAA AAT GAC ATA GAG AAG
Gln Lys Gln Phe Asn Ala Thr Thr Ile Pro Glu Asn Asp Ile Glu Lys
        755                 760                 765

ACT GAC CCT TGG TTT GCA CAC AGA ACA CCT ATG CCT AAA ATA CAA AAT
Thr Asp Pro Trp Phe Ala His Arg Thr Pro Met Pro Lys Ile Gln Asn
770                 775                 780

GTC TCC TCT AGT GAT TTG TTG ATG CTC TTG CGA CAG AGT CCT ACT CCA
Val Ser Ser Ser Asp Leu Leu Met Leu Leu Arg Gln Ser Pro Thr Pro
785                 790                 795                 800

CAT GGG CTA TCC TTA TCT GAT CTC CAA GAA GCC AAA TAT GAG ACT TTT
His Gly Leu Ser Leu Ser Asp Leu Gln Glu Ala Lys Tyr Glu Thr Phe
                805                 810                 815

TCT GAT GAT CCA TCA CCT GGA GCA ATA GAC AGT AAT AAC AGC CTG TCT
Ser Asp Asp Pro Ser Pro Gly Ala Ile Asp Ser Asn Asn Ser Leu Ser
            820                 835                 830

GAA ATG ACA CAC TTC AGG CCA CAG CTC CAT CAC AGT GGG GAC ATG GTA
Glu Met Thr His Phe Arg Pro Gln Leu His His Ser Gly Asp Met Val
            835                 840                 845

TTT ACC CCT GAG TCA GGC CTC CAA TTA AGA TTA AAT GAG AAA CTG GGG
Phe Thr Pro Glu Ser Gly Leu Gln Leu Arg Leu Asn Glu Lys Leu Gly
        850                 855                 860

ACA ACT GCA GCA ACA GAG TTG AAG AAA CTT GAT TTC AAA GTT TCT AGT
Thr Thr Ala Ala Thr Glu Leu Lys Lys Leu Asp Phe Lys Val Ser Ser
865                 870                 875                 880

ACA TCA AAT AAT CTG ATT TCA ACA ATT CCA TCA GAC AAT TTG GCA GCA
Thr Ser Asn Asn Leu Ile Ser Thr Ile Pro Ser Asp Asn Leu Ala Ala
            885                 890                 895
```

-continued

| | | | | | | | | | | | | | |
|---|---|---|---|---|---|---|---|---|---|---|---|---|---|
|GGT|ACT|GAT|AAT|ACA|AGT|TCC|TTA|GGA|CCC|CCA|AGT|ATG|CCA|GTT|CAT|
|Gly|Thr|Asp|Asn|Thr|Ser|Ser|Leu|Gly|Pro|Pro|Ser|Met|Pro|Val|His|
| | | |900| | | |905| | | |910| | | | |

TAT GAT AGT CAA TTA GAT ACC ACT CTA TTT GGC AAA AAG TCA TCT CCC
Tyr Asp Ser Gln Leu Asp Thr Thr Leu Phe Gly Lys Lys Ser Ser Pro
        915             920                 925

CTT ACT GAG TCT GGT GGA CCT CTG AGC TTG AGT GAA GAA AAT AAT GAT
Leu Thr Glu Ser Gly Gly Pro Leu Ser Leu Ser Glu Glu Asn Asn Asp
    930             935                 940

TCA AAG TTG TTA GAA TCA GGT TTA ATG AAT AGC CAA GAA AGT TCA TGG
Ser Lys Leu Leu Glu Ser Gly Leu Met Asn Ser Gln Glu Ser Ser Trp
945             950                 955                 960

GGA AAA AAT GTA TCG TCA ACA GAG AGT GGT AGG TTA TTT AAA GGG AAA
Gly Lys Asn Val Ser Ser Thr Glu Ser Gly Arg Leu Phe Lys Gly Lys
                965                 970                 975

AGA GCT CAT GGA CCT GCT TTG TTG ACT AAA GAT AAT GCC TTA TTC AAA
Arg Ala His Gly Pro Ala Leu Leu Thr Lys Asp Asn Ala Leu Phe Lys
                980                 985                 990

GTT AGC ATC TCT TTG TTA AAG ACA AAC AAA ACT TCC AAT AAT TGA GCA
Val Ser Ile Ser Leu Leu Lys Thr Asn Lys Thr Ser Asn Asn Ser Ala
            995             1000                1005

ACT AAT AGA AAG ACT CAC ATT GAT GGC CCA TCA TTA TTA ATT GAG AAT
Thr Asn Arg Lys Thr His Ile Asp Gly Pro Ser Leu Leu Ile Glu Asn
    1010                1015                1020

AGT CCA TCA GTC TGG CAA AAT ATA TTA GAA AGT GAC ACT GAG TTT AAA
Ser Pro Ser Val Trp Gln Asn Ile Leu Glu Ser Asp Thr Glu Phe Lys
1025                1030                1035                1040

AAA GTG ACA CCT TTG ATT CAT GAC AGA ATG CTT ATG GAC AAA AAT GCT
Lys Val Thr Pro Leu Ile His Asp Arg Met Leu Met Asp Lys Asn Ala
                1045                1050                1055

ACA GCT TTG AGG CTA AAT CAT ATG TCA AAT AAA ACT ACT TCA TCA AAA
Thr Ala Leu Arg Leu Asn His Met Ser Asn Lys Thr Thr Ser Ser Lys
                1060                1065                1070

AAC ATG GAA ATG GTC CAA CAG AAA AAA GAG GGC CCC ATT CCA CCA GAT
Asn Met Glu Met Val Gln Gln Lys Lys Glu Gly Pro Ile Pro Pro Asp
    1075                1080                1085

GCA CAA AAT CCA GAT ATG TCG TTC TTT AAG ATG CTA TTC TTG CCA GAA
Ala Gln Asn Pro Asp Met Ser Phe Phe Lys Met Leu Phe Leu Pro Glu
    1090                1095                1100

TCA GCA AGG TGG ATA CAA AGG ACT CAT GGA AAG AAC TCT CTG AAC TCT
Ser Ala Arg Trp Ile Gln Arg Thr His Gly Lys Asn Ser Leu Asn Ser
1105                1110                1115                1120

GGG CAA GGC CCC AGT CCA AAG CAA TTA GTA TCC TTA GGA CCA GAA AAA
Gly Gln Gly Pro Ser Pro Lys Gln Leu Val Ser Leu Gly Pro Glu Lys
                1125                1130                1135

TCT GTG GAA GGT CAG AAT TTC TTG TCT GAG AAA AAC AAA GTG GTA GTA
Ser Val Glu Gly Gln Asn Phe Leu Ser Glu Lys Asn Lys Val Val Val
                1140                1145                1150

GGA AAG GGT GAA TTT ACA AAG GAC GTA GGA CTC AAA GAG ATG GTT TTT
Gly Lys Gly Glu Phe Thr Lys Asp Val Gly Leu Lys Glu Met Val Phe
        1155                1160                1165

CCA AGC AGC AGA AAC CTA TTT CTT ACT AAC TTG GAT AAT TTA CAT GAA
Pro Ser Ser Arg Asn Leu Phe Leu Thr Asn Leu Asp Asn Leu His Glu
    1170                1175                1180

AAT AAT ACA CAC AAT CAA GAA AAA AAA ATT CAG GAA GAA ATA GAA AAG
Asn Asn Thr His Asn Gln Glu Lys Lys Ile Gln Glu Glu Ile Glu Lys
1185                1190                1195                1200

AAG GAA ACA TTA ATC CAA GAG AAT GTA GTT TTG CCT CAG ATA CAT ACA
Lys Glu Thr Leu Ile Gln Glu Asn Val Val Leu Pro Gln Ile His Thr
                1205                1210                1215

GTG ACT GGC ACT AAG AAT TTC ATG AAG AAC CTT TTC TTA CTG AGC ACT
Val Thr Gly Thr Lys Asn Phe Met Lys Asn Leu Phe Leu Leu Ser Thr
        1220                1225                1230

```
AGG CAA AAT GTA GAA GGT TCA TAT GAC GGG GCA TAT GCT CCA GTA CTT
Arg Gln Asn Val Glu Gly Ser Tyr Asp Gly Ala Tyr Ala Pro Val Leu
    1235                1240                1245

CAA GAT TTT AGG TCA TTA AAT GAT TCA ACA AAT AGA ACA AAG AAA CAC
Gln Asp Phe Arg Ser Leu Asn Asp Ser Thr Asn Arg Thr Lys Lys His
    1250                1255                1260

ACA GCT CAT TTC TCA AAA AAA GGG GAG GAA GAA AAC TTG GAA GGC TTG
Thr Ala His Phe Ser Lys Lys Gly Glu Glu Glu Asn Leu Glu Gly Leu
1265                1270                1275                1280

GGA AAT CAA ACC AAG CAA ATT GTA GAG AAA TAT GCA TGC ACC ACA AGG
Gly Asn Gln Thr Lys Gln Ile Val Glu Lys Tyr Ala Cys Thr Thr Arg
                1285                1290                1295

ATA TCT CCT AAT ACA AGC CAG CAG AAT TTT GTC ACG CAA CGT AGT AAG
Ile Ser Pro Asn Thr Ser Gln Gln Asn Phe Val Thr Gln Arg Ser Lys
            1300                1305                1310

AGA GCT TTG AAA CAA TTC AGA CTC CCA CTA GAA GAA ACA GAA CTT GAA
Arg Ala Leu Lys Gln Phe Arg Leu Pro Leu Glu Glu Thr Glu Leu Glu
        1315                1320                1325

AAA AGG ATA ATT GTG GAT GAC ACC TCA ACC CAG TGG TCC AAA AAC ATG
Lys Arg Ile Ile Val Asp Asp Thr Ser Thr Gln Trp Ser Lys Asn Met
    1330                1335                1340

AAA CAT TTG ACC CCG AGC ACC CTC ACA CAG ATA GAC TAC AAT GAG AAG
Lys His Leu Thr Pro Ser Thr Leu Thr Gln Ile Asp Tyr Asn Glu Lys
1345                1350                1355                1360

GAG AAA GGG GCC ATT ACT CAG TCT CCC TTA TCA GAT TGC CTT ACG AGG
Glu Lys Gly Ala Ile Thr Gln Ser Pro Leu Ser Asp Cys Leu Thr Arg
                1365                1370                1375

AGT CAT AGC ATC CCT CAA GCA AAT AGA TCT CCA TTA CCC ATT GCA AAG
Ser His Ser Ile Pro Gln Ala Asn Arg Ser Pro Leu Pro Ile Ala Lys
            1380                1385                1390

GTA TCA TCA TTT CCA TCT ATT AGA CCT ATA TAT CTG ACC AGG GTC CTA
Val Ser Ser Phe Pro Ser Ile Arg Pro Ile Tyr Leu Thr Arg Val Leu
        1395                1400                1405

TTC CAA GAC AAC TCT TCT CAT CTT CCA GCA GCA TCT TAT AGA AAG AAA
Phe Gln Asp Asn Ser Ser His Leu Pro Ala Ala Ser Tyr Arg Lys Lys
    1410                1415                1420

GAT TCT GGG GTC CAA GAA AGC AGT CAT TTC TTA CAA GGA GCC AAA AAA
Asp Ser Gly Val Gln Glu Ser Ser His Phe Leu Gln Gly Ala Lys Lys
1425                1430                1435                1440

AAT AAC CTT TCT TTA GCC ATT CTA ACC TTG GAG ATG ACT GGT GAT CAA
Asn Asn Leu Ser Leu Ala Ile Leu Thr Leu Glu Met Thr Gly Asp Gln
                1445                1450                1455

AGA GAG GTT GGC TCC CTG GGG ACA AGT GCC ACA AAT TCA GTC ACA TAC
Arg Glu Val Gly Ser Leu Gly Thr Ser Ala Thr Asn Ser Val Thr Tyr
            1460                1465                1470

AAG AAA GTT GAG AAC ACT GTT CTC CCG AAA CCA GAC TTG CCC AAA ACA
Lys Lys Val Glu Asn Thr Val Leu Pro Lys Pro Asp Leu Pro Lys Thr
        1475                1480                1485

TCT GGC AAA GTT GAA TTG CTT CCA AAA GTT CAC ATT TAT CAG AAG GAC
Ser Gly Lys Val Glu Leu Leu Pro Lys Val His Ile Tyr Gln Lys Asp
    1490                1495                1500

CTA TTC CCT ACG GAA ACT AGC AAT GGG TCT CCT GGC CAT CTG GAT CTC
Leu Phe Pro Thr Glu Thr Ser Asn Gly Ser Pro Gly His Leu Asp Leu
1505                1510                1515                1520

GTG GAA GGG AGC CTT CTT CAG GGA ACA GAG GGA GCG ATT AAG TGG AAT
Val Glu Gly Ser Leu Leu Gln Gly Thr Glu Gly Ala Ile Lys Trp Asn
                1525                1530                1535

GAA GCA AAC AGA CCT GGA AAA GTT CCC TTT CTG AGA GTA GCA ACA GAA
Glu Ala Asn Arg Pro Gly Lys Val Pro Phe Leu Arg Val Ala Thr Glu
            1540                1545                1550
```

```
AGC TCT GCA AAG ACT CCC TCC AAG CTA TTG GAT CCT CTT GCT TGG GAT
Ser Ser Ala Lys Thr Pro Ser Lys Leu Leu Asp Pro Leu Ala Trp Asp
        1555                1560                1565

AAC CAC TAT GGT ACT CAG ATA CCA AAA GAA GAG TGG AAA TCC CAA GAG
Asn His Tyr Gly Thr Gln Ile Pro Lys Glu Glu Trp Lys Ser Gln Glu
    1570                1575                1580

AAG TCA CCA GAA AAA ACA GCT TTT AAG AAA AAG GAT ACC ATT TTG TCC
Lys Ser Pro Glu Lys Thr Ala Phe Lys Lys Lys Asp Thr Ile Leu Ser
1585            1590                1595                    1600

CTG AAC GCT TGT GAA AGC AAT CAT GCA ATA GCA GCA ATA AAT GAG GGA
Leu Asn Ala Cys Glu Ser Asn His Ala Ile Ala Ala Ile Asn Glu Gly
                1605                1610                1615

CAA AAT AAG CCC GAA ATA GAA GTC ACC TGG GCA AAG CAA GGT AGG ACT
Gln Asn Lys Pro Glu Ile Glu Val Thr Trp Ala Lys Gln Gly Arg Thr
            1620                1625                1630

GAA AGG CTG TGC TCT CAA AAC CCA CCA GTC TTG AAA CGC CAT CAA CGG
Glu Arg Leu Cys Ser Gln Asn Pro Pro Val Leu Lys Arg His Gln Arg
        1635                1640                1645

GAA ATA ACT CGT ACT ACT CTT CAG TCA GAT CAA GAG GAA ATT GAC TAT
Glu Ile Thr Arg Thr Thr Leu Gln Ser Asp Gln Glu Glu Ile Asp Tyr
    1650                1655                1660

GAT GAT ACC ATA TCA GTT GAA ATG AAG AAG GAA GAT TTT GAC ATT TAT
Asp Asp Thr Ile Ser Val Glu Met Lys Lys Glu Asp Phe Asp Ile Tyr
1665            1670                1675                    1680

GAT GAG GAT GAA AAT CAG AGC CCC CGC AGC TTT CAA AAG AAA ACA CGA
Asp Glu Asp Glu Asn Gln Ser Pro Arg Ser Phe Gln Lys Lys Thr Arg
                1685                1690                1695

CAC TAT TTT ATT GCT GCA GTG GAG AGG CTC TGG GAT TAT GGG ATG AGT
His Tyr Phe Ile Ala Ala Val Glu Arg Leu Trp Asp Tyr Gly Met Ser
            1700                1705                1710

AGC TCC CCA CAT GTT CTA AGA AAC AGG GCT CAG AGT GGC AGT GTC CCT
Ser Ser Pro His Val Leu Arg Asn Arg Ala Gln Ser Gly Ser Val Pro
        1715                1720                1725

CAG TTC AAG AAA GTT GTT TTC CAG GAA TTT ACT GAT GGC TCC TTT ACT
Gln Phe Lys Lys Val Val Phe Gln Glu Phe Thr Asp Gly Ser Phe Thr
    1730                1735                1740

CAG CCC TTA TAC CGT GGA GAA CTA AAT GAA CAT TTG GGA CTC CTG GGG
Gln Pro Leu Tyr Arg Gly Glu Leu Asn Glu His Leu Gly Leu Leu Gly
1745                1750                1755                1760

CCA TAT ATA AGA GCA GAA GTT GAA GAT AAT ATC ATG GTA ACT TTC AGA
Pro Tyr Ile Arg Ala Glu Val Glu Asp Asn Ile Met Val Thr Phe Arg
                1765                1770                1775

AAT CAG GCC TCT CGT CCC TAT TCC TTC TAT TCT AGC CTT ATT TCT TAT
Asn Gln Ala Ser Arg Pro Tyr Ser Phe Tyr Ser Ser Leu Ile Ser Tyr
            1780                1785                1790

GAG GAA GAT CAG AGG CAA GGA GCA GAA CCT AGA AAA AAC TTT GTC AAG
Glu Glu Asp Gln Arg Gln Gly Ala Glu Pro Arg Lys Asn Phe Val Lys
        1795                1800                1805

CCT AAT GAA ACC AAA ACT TAC TTT TGG AAA GTG CAA CAT CAT ATG GCA
Pro Asn Glu Thr Lys Thr Tyr Phe Trp Lys Val Gln His His Met Ala
    1810                1815                1820

CCC ACT AAA GAT GAG TTT GAC TGC AAA GCC TGG GCT TAT TTC TCT GAT
Pro Thr Lys Asp Glu Phe Asp Cys Lys Ala Trp Ala Tyr Phe Ser Asp
1825            1830                1835                    1840

GTT GAC CTG GAA AAA GAT GTG CAC TCA GGC CTG ATT GGA CCC CTT CTG
Val Asp Leu Glu Lys Asp Val His Ser Gly Leu Ile Gly Pro Leu Leu
                1845                1850                1855

GTC TGC CAC ACT AAC ACA CTG AAC CCT GCT CAT GGG AGA CAA GTG ACA
Val Cys His Thr Asn Thr Leu Asn Pro Ala His Gly Arg Gln Val Thr
            1860                1865                1870

GTA CAG GAA TTT GCT CTG TTT TTC ACC ATC TTT GAT GAG ACC AAA AGC
Val Gln Glu Phe Ala Leu Phe Phe Thr Ile Phe Asp Glu Thr Lys Ser
        1875                1880                1885
```

-continued

```
TGG TAC TTC ACT GAA AAT ATG GAA AGA AAC TGC AGG GCT CCC TGC AAT
Trp Tyr Phe Thr Glu Asn Met Glu Arg Asn Cys Arg Ala Pro Cys Asn
    1890                1895                1900

ATC CAG ATG GAA GAT CCC ACT TTT AAA GAG AAT TAT CGC TTC CAT GCA
Ile Gln Met Glu Asp Pro Thr Phe Lys Glu Asn Tyr Arg Phe His Ala
1905                1910                1915                1920

ATC AAT GGC TAC ATA ATG GAT ACA CTA CCT GGC TTA GTA ATG GCT CAG
Ile Asn Gly Tyr Ile Met Asp Thr Leu Pro Gly Leu Val Met Ala Gln
                1925                1930                1935

GAT CAA AGG ATT CGA TGG TAT CTG CTC AGC ATG GGC AGC AAT GAA AAC
Asp Gln Arg Ile Arg Trp Tyr Leu Leu Ser Met Gly Ser Asn Glu Asn
            1940                1945                1950

ATC CAT TCT ATT CAT TTC AGT GGA CAT GTG TTC ACT GTA CGA AAA AAA
Ile His Ser Ile His Phe Ser Gly His Val Phe Thr Val Arg Lys Lys
        1955                1960                1965

GAG GAG TAT AAA ATG GCA CTG TAC AAT CTC TAT CCA GGT GTT TTT GAG
Glu Glu Tyr Lys Met Ala Leu Tyr Asn Leu Tyr Pro Gly Val Phe Glu
    1970                1975                1980

ACA GTG GAA ATG TTA CCA TCC AAA GCT GGA ATT TGG CGG GTG GAA TGC
Thr Val Glu Met Leu Pro Ser Lys Ala Gly Ile Trp Arg Val Glu Cys
1985                1990                1995                2000

CTT ATT GGC GAG CAT CTA CAT GCT GGG ATG AGC ACA CTT TTT CTG GTG
Leu Ile Gly Glu His Leu His Ala Gly Met Ser Thr Leu Phe Leu Val
                2005                2010                2015

TAC AGC AAT AAG TGT CAG ACT CCC CTG GGA ATG GCT TCT GGA CAC ATT
Tyr Ser Asn Lys Cys Gln Thr Pro Leu Gly Met Ala Ser Gly His Ile
            2020                2025                2030

AGA GAT TTT CAG ATT ACA GCT TCA GGA CAA TAT GGA CAG TGG GCC CCA
Arg Asp Phe Gln Ile Thr Ala Ser Gly Gln Tyr Gly Gln Trp Ala Pro
        2035                2040                2045

AAG CTG GCC AGA CTT CAT TAT TCC GGA TCA ATC AAT GCC TGG AGC ACC
Lys Leu Ala Arg Leu His Tyr Ser Gly Ser Ile Asn Ala Trp Ser Thr
    2050                2055                2060

AAG GAG CCC TTT TCT TGG ATC AAG GTG GAT CTG TTG GCA CCA ATG ATT
Lys Glu Pro Phe Ser Trp Ile Lys Val Asp Leu Leu Ala Pro Met Ile
2065                2070                2075                2080

ATT CAC GGC ATC AAG ACC CAG GGT GCC CGT CAG AAG TTC TCC AGC CTC
Ile His Gly Ile Lys Thr Gln Gly Ala Arg Gln Lys Phe Ser Ser Leu
                2085                2090                2095

TAC ATC TCT CAG TTT ATC ATC ATG TAT AGT CTT GAT GGG AAG AAG TGG
Tyr Ile Ser Gln Phe Ile Ile Met Tyr Ser Leu Asp Gly Lys Lys Trp
            2100                2105                2110

CAG ACT TAT CGA GGA AAT TCC ACT GGA ACC TTA ATG GTC TTC TTT GGC
Gln Thr Tyr Arg Gly Asn Ser Thr Gly Thr Leu Met Val Phe Phe Gly
        2115                2120                2125

AAT GTG GAT TCA TCT GGG ATA AAA CAC AAT ATT TTT AAC CCT CCA ATT
Asn Val Asp Ser Ser Gly Ile Lys His Asn Ile Phe Asn Pro Pro Ile
    2130                2135                2140

ATT GCT CGA TAC ATC CGT TTG CAC CCA ACT CAT TAT AGC ATT CGC AGC
Ile Ala Arg Tyr Ile Arg Leu His Pro Thr His Tyr Ser Ile Arg Ser
2145                2150                2155                2160

ACT CTT CGC ATG GAG TTG ATG GGC TGT GAT TTA AAT AGT TGC AGC ATG
Thr Leu Arg Met Glu Leu Met Gly Cys Asp Leu Asn Ser Cys Ser Met
                2165                2170                2175

CCA TTG GGA ATG GAG AGT AAA GCA ATA TCA GAT GCA CAG ATT ACT GCT
Pro Leu Gly Met Glu Ser Lys Ala Ile Ser Asp Ala Gln Ile Thr Ala
            2180                2185                2190

TCA TCC TAC TTT ACC AAT ATG TTT GCC ACC TGG TCT CCT TCA AAA GCT
Ser Ser Tyr Phe Thr Asn Met Phe Ala Thr Trp Ser Pro Ser Lys Ala
        2195                2200                2205
```

-continued

```
CGA CTT CAC CTC CAA GGG AGG AGT AAT GCC TGG AGA CCT CAG GTG AAT
Arg Leu His Leu Gln Gly Arg Ser Asn Ala Trp Arg Pro Gln Val Asn
2210                    2215                2220

AAT CCA AAA GAG TGG CTG CAA GTG GAC TTC CAG AAG ACA ATG AAA GTC
Asn Pro Lys Glu Trp Leu Gln Val Asp Phe Gln Lys Thr Met Lys Val
2225            2230                2235                    2240

ACA GGA GTA ACT ACT CAG GGA GTA AAA TCT CTG CTT ACC AGC ATG TAT
Thr Gly Val Thr Thr Gln Gly Val Lys Ser Leu Leu Thr Ser Met Tyr
                2245            2250                    2255

GTG AAG GAG TTC CTC ATC TCC AGC AGT CAA GAT GGC CAT CAG TGG ACT
Val Lys Glu Phe Leu Ile Ser Ser Ser Gln Asp Gly His Gln Trp Thr
            2260            2265                2270

CTC TTT TTT CAG AAT GGC AAA GTA AAG GTT TTT CAG GGA AAT CAA GAC
Leu Phe Phe Gln Asn Gly Lys Val Lys Val Phe Gln Gly Asn Gln Asp
        2275                2280            2285

TCC TTC ACA CCT GTG GTG AAC TCT CTA GAC CCA CCG TTA CTG ACT CGC
Ser Phe Thr Pro Val Val Asn Ser Leu Asp Pro Pro Leu Leu Thr Arg
        2290            2295            2300

TAC CTT CGA ATT CAC CCC CAG AGT TGG GTG CAC CAG ATT GCC CTG AGG
Tyr Leu Arg Ile His Pro Gln Ser Trp Val His Gln Ile Ala Leu Arg
2305                2310            2315                    2320

ATG GAG GTT CTG GGC TGC GAG GCA CAG GAC CTC TAC TGA
Met Glu Val Leu Gly Cys Glu Ala Gln Asp Leu Tyr ***
                2325            2330    2332
```

In hemophilia A patients, Factor VIII is genetically defected or inactive and hence the active Factor VIII is not present or reduced in activity in blood, thereby blood coagulation failure and bleeding diseases result. Accordingly, Factor VIII is given to the hemophilia A patients for stopping the bleeding. In this therapy, Factor VIII has been used as a concentrated preparation of Factor VIII, which has a high titer but contains a large amount of contaminants such as fibrinogen, fibronectin, etc. In recent years, a highly purified Factor VIII preparation has been prepared using the immunoaffinity chromatographic technique with a monoclonal antibody.

However, even such a preparation cannot remove a risk of infection with a hepatitis virus or an unknown virus since it is prepared from a human plasma. In addition, since Factor VIII is present in the plasma only in a quite small amount, it is laborsome to obtain the highly purified Factor VIII and the available amount of human plasma is also limited. From this point of view, in order to provide a cheap and safe highly purified Factor VIII preparation which is not derived from human plasma and hence does not contain contaminants of viruses, the gene recombination technique has nowadays been used in which a gene coding for the human Factor VIII is cloned and said gene is expressed in an animal cell to produce Factor VIII. DNA of the human Factor VIII has been cloned by Gitschier et al. (J. Gitschier et al., Nature 312, 326–330, 1984) and an expression of cDNA of the human Factor VIII in hamster kidney cells has been reported by Wood et al. (W. I. Wood et al., Nature 312, 330–337, 1984). In addition, Toole et al. (J. J. Toole et al., Nature 312, 342–347, 1984), Truett et al. (M. A. Truett et al., DNA 4, 333–349, 1985), and Pavirani et al. (A. Pavirani et al., Biotechnology 5, 389–392, 1987) also reported the cloning of cDNA of the human Factor VIII and the expression thereof in a mammalian cell.

However, the expression described in the above literatures is a transient one and is not satisfactory in an industrial point of view. cDNA of the human Factor VIII comprises a nucleotide sequence of about 7000 to 8000 base pairs (bp) in which 7053 bp code for Factor VIII. Factor VIII is a protein having 2351 amino acid residues wherein a peptide portion of 19 amino acid residues at the N-terminus is a signal peptide which is cleaved by a signal peptidase when Factor VIII is released through a membrane to produce a Factor VIII comprising 2332 amino acid residues. As is clear, Factor VIII is a protein having an especially large molecular weight among those proteins found in the living body, and hence, the expression of such a gross protein using the gene recombination technique encounters various obstacles as compared to the expression of other proteins having a low molecular weight.

One of means to solve the above problems is a partial modification of a gene coding for Factor VIII. There have been various reports as to the structural analysis of Factor VIII based on the current gene recombination technique. Factor VIII has been shown to have a domain structure of A1-A2-B-A3-C1-C2 based on the homology thereof by the analysis of the amino acid sequence (G. A. Vehar et al., Nature 312, 337–342, 1984) and it is supposed that a part or most part of the B-domain is dispensable for exhibiting Factor VIII activity. For the purpose of preparing a molecular species of Factor VIII which has as low a molecular weight as possible but still shows a biochemical activity in order to increase the efficiency of the gene expression, there are several reports as to a preparation of an improved Factor VIII wherein a part or all of the B-domain is deleted.

Toole et al. have expressed an improved Factor VIII, wherein a polypeptide fragment comprising the amino acid residue No. 1 Alanine to the amino acid residue No. 981 Proline (H-chain) and a polypeptide fragment comprising the amino acid residue No. 1563 Aspartic acid to the amino acid residue No. 2332 Tyrosine (L-chain) are directly combined via the acid amid bonding (hereinafter abbreviated as "981Pro-1563Asp Factor VIII") and 759Thr-1640Pro Factor VIII, in COS cells (Proc. N. A. S. USA 83, 5939–5942, 1986) and in Chinese hamster ovary (CHO) cells (PCT application WO 86/06101) using adenovirus type 2 major late promoter. Eaton et al. have expressed 796Gln-1563Asn Factor VIII in COS cells using SV40 early promoter (D. L. Eaton et al., Biochemistry 25, 8343–8347, 1986). Although there have been attempted the expression of Factor VIII wherein the region coding for the B-domain is deleted by various groups and in fact the expression level was improved, it is not satisfactory for the production of Factor VIII on an industrial scale. In addition, since Factor VIII is expressed as a fused molecule deleted of the B-domain, the artificial amino acid sequence (junction region of H-chain and L-chain) remains without complete processing, and when administered into blood, possibly shows a novel antigenicity (Blood 76, 1593–1600, 1990). Under the circumstances, there is a desire for development of the technique for the production of the active and safe Factor VIII.

BRIEF DESCRIPTION OF THE INVENTION

Under the circumstances, the present inventors have intensively studied as to the efficient expression of human Factor VIII which contains only a naturally occurring amino acid sequence, and as a result, have found that Factor VIII H-chain and L-chain of a size in which the most part of the B-domain is deleted is expressed in a separate cistron so that each of H-chain and L-chain can be obtained in a large amount and that a Factor VIII H-chain—L-chain complex having a coagulation activity can be expressed at a high level by co-expressing these H-chain and L-chain. The present invention provides a safe Factor VIII containing no non-naturally occurring amino acid sequence at a much higher expression level as compared to the expression of the conventional full length Factor VIII or the expression of a fused molecule wherein B-domain is deleted and a process for preparing Factor VIII which is sufficiently applicable to the production of Factor VIII on an industrial level.

An object of the present invention is to provide a plasmid for expression of a human coagulation factor VIII H-chain, which comprises the following DNAs (a) to (d) within the same cistron in a transcriptional direction:

(a) a promoter capable of acting in an animal cell, (b) a DNA coding for a signal peptide including an initiation codon, (c) a DNA coding for A1-A2 domains and for α amino acids at the N-terminus of B-domain of the human coagulation factor VIII [amino acids positioned at 1 to (740+α) on the amino acid sequence of the human coagulation factor VIII, wherein α: 1≦α≦16, α is an integer], and (d) a termination codon.

Another object of the present invention is to provide a plasmid for expression of a human coagulation factor VIII L-chain, which comprises the following DNAs (a') to (d') within the same cistron in a transcriptional direction:

(a') a promoter capable of acting in an animal cell, (b') a DNA coding for a signal peptide including an initiation codon, (c') a DNA coding for β amino acids at the C-terminus of B-domain, and for A3-C1-C2 domains of the human coagulation factor VIII [amino acids positioned at (1649-β) to 2332 on the amino acid sequence of the human coagulation factor VIII, wherein β: 30≦β≦136, β is an integer], and (d') a termination codon.

Further object of the present invention is to provide a transformed animal cell which is transformed with at least either the above plasmid for expression of the human coagulation factor VIII H-chain or the above plasmid for expression of the human coagulation factor VIII L-chain.

Still another object of the present invention is to provide a transformed animal cell which is cotransformed with both the above plasmid for expression of the human coagulation factor VIII H-chain and the above plasmid for expression of the human coagulation factor VIII L-chain.

Still further object of the present invention is to provide a process for preparing a human coagulation factor VIII H-chain, which comprises forming a transformed animal cell by introducing the plasmid for expression of the human coagulation factor VIII H-chain into an animal cell, culturing said cell to produce the human coagulation factor VIII H-chain in the culture medium, and collecting the thus produced human coagulation factor VIII H-chain.

Still another object of the present invention is to provide a process for preparing a human coagulation factor VIII L-chain, which comprises forming a transformed animal cell by introducing the plasmid for expression of the human coagulation factor VIII L-chain into an animal cell, culturing said cell to produce the human coagulation factor VIII L-chain in the culture medium, and collecting the thus produced human coagulation factor VIII L-chain.

Still further object of the present invention is to provide a process for preparing a human coagulation factor VIII protein complex, which comprises forming a transformed animal cell by introducing both the plasmid for expression of the human coagulation factor VIII H-chain and the plasmid for expression of the human coagulation factor VIII L-chain into an animal cell, culturing said cell to produce the human coagulation factor VIII protein complex in the culture medium, and collecting the thus produced human coagulation factor VIII protein complex.

These and other objects and the advantages thereof will be apparent to those skilled in the art from the following description.

DETAILED DESCRIPTION OF THE INVENTION

Figure 1:
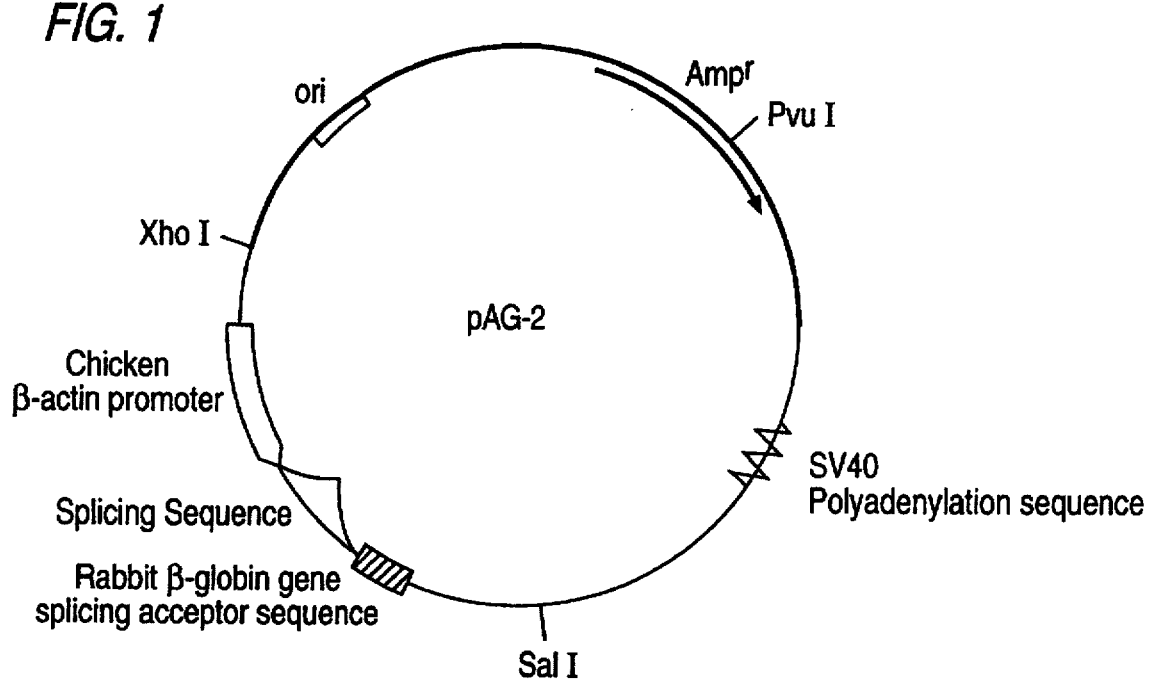
FIG. 1 illustrates the structure of the plasmid pAG-2.

According to the process of the present invention, the H-chain in which the most part of the B-domain is deleted and the full length of L-chain or the L-chain which contains a C-terminal portion of the B-domain are expressed as a separate cistron. In the gene expression in organisms, a structural gene comprises an initiation codon ATG which is an initiation signal for translation, a DNA sequence coding for an actual amino acid sequence and a termination codon as a signal for termination of the translation. In addition, a gene coding for an amino acid sequence involved in the transfer of a protein called a signal peptide is present at the 5'-terminus of the structural gene for secretion of an expressed protein. In case of Factor VIII, the signal peptide comprises 19 amino acids. In the process for expression of the present invention, the termination codon is introduced immediately downstream of a gene coding for the H-chain to be expressed within the same open reading frame, and at the same time, a gene coding for the signal peptide including the initiation codon is introduced immediately upstream of a gene coding for the L-chain to be expressed within the same open reading frame. This process for expression of the H-chain and L-chain of Factor VIII as a separate structural gene is hereinafter referred to as "separate expression".

The expression of the H-chain in the present invention is conducted with the most part of the B-domain deleted. That is, the expression is conducted in the form of the 740th Arginine which is supposed to be the C-terminus of 90 k dalton protein of Factor VIII H-chain derived from human plasma or in the form in which several amino acids at the N-terminus of the B-domain are added to said 740th Arginine. As the result of the present inventors' study, it was found that the H-chain 90 k dalton protein can be obtained at a higher expression efficiency by 10-fold or more by adding a gene coding for several amino acids at the N-terminus of the B-domain to a DNA coding for the 740th Arginine at the C-terminus of the H-chain and then introducing the termination codon immediately downstream of said gene coding for several amino acids as compared to the introduction of the termination codon into immediately downstream of the DNA coding for the 740th Arginine. According to the process of the present invention, the expression level can greatly be increased by introducing the termination codon into immediately downstream (3'-terminus) of a DNA coding for the H-chain in which 1 to 5 amino acids at the N-terminus of the B-domain are added to the 740th Arginine and then expressing the thus obtained DNA in an animal cell. In this case, it should be noted that the expression efficiency is possibly lowered when the number of the amino acids at the N-terminus of the B-domain to be added to the H-chain is too long so that the H-chain contains a sequence: Asparagine+x (optional amino acid)+Threonine or Serine, said sequence possibly allowing glycosilation, and hence, the number of the amino acids at the N-terminus of the B-domain to be added is preferably 1 to about 16 so that the H-chain does not contain said sequence.

In the separate expression of the human coagulation factor VIII of the present invention wherein the human coagulation factor VIII protein complex is produced by coexpression of the H-chain and the L-chain in the same cell, it was confirmed that a lowered expression level of the human coagulation factor VIII protein complex as a whole is especially due to a lowered expression level of the H-chain. Accordingly, by constructing the cistron for expression of the H-chain according to the present invention as mentioned above, the expression level of the human coagulation factor VIII protein complex can be improved to a high degree without revising the expression of the L-chain.

For the expression of the L-chain, there is used a DNA coding for a protein in which a signal peptide is added just prior to the L-chain protein to be expressed. The signal peptide may be selected from a variety of signal sequences reported in literatures as well as the original signal peptide of Factor VIII. For example, there can be used signal sequences of secretion proteins of eucaryotes such as immunoglobulin H-chain and L-chain, tissue plasminogen activator, albumin and the like. In addition, a newly prepared signal sequence based on an artificially synthesized sequence can also be used. When these signal peptides other than the original one is used, the introduced signal peptide must be cleaved by signal peptidase during secretion of protein so that the mature protein reserves only the amino acid sequence of the original Factor VIII.

In the process of the present invention, the expression is conducted on a DNA wherein the DNA coding for the signal peptide of Factor VIII is added just upstream of the DNA coding for the 1649th Glutamic acid at the N-terminus of 80 k dalton protein of natural human Factor VIII L-chain. This signal peptide is cleaved by a signal peptidase during secretion of the protein from cell, and as a result, a mature protein having only the amino acid sequence of the original L-chain can be obtained. Furthermore, the present inventors have also found that the L-chain 80 k dalton protein can be expressed with addition of the amino acid sequence at the C-terminus of the B-domain to the N-terminus of the original L-chain protein and thereby the expression level of the L-chain can be greatly increased.

The above-mentioned B-domain-derived sequence may comprise several to a hundred and several amino acids. According to the study of the present inventors, the expression level of the L-chain with the addition of 86 amino acids (from the 1563rd Aspartic acid to the 1648th Arginine) is higher than that of the original L-chain (starting from the 1649th Glutamic acid) by 5-fold or more. The analysis of the properties of the expressed L-chain protein with addition of a part of the B-domain showed that most of the expressed protein are processed into the 80 k dalton protein. The analysis of the amino acid sequence at the N-terminus of this protein also showed mainly an amino acid sequence starting from the 1649th Glutamic acid. The number of the amino acids at the C-terminus of the B-domain to be added is preferably from about 30 to about 136 for avoiding the addition of glycoside and not for intervening the action of signal peptidase.

For the expression of these genes, a promoter (a sequence recognized by RNA polymerase) is introduced into upstream of the structural gene. A promoter having a strong activity should be selected for the gene expression aimed at industrialization. Such a promoter having a strong activity includes, for example, SV40 early and late promoter, adenovirus promoter, cytomegalovirus promoter, metallothionein promoter, and the like.

In the preferred embodiment of the present invention, a chicken β-actin promoter is used. Using this promoter, the present inventors have attained a high expression system of an animal culture cell (Japanese Patent First Publication (Kokai) No. 5890/1990). The separate expression of Factor VIII using the β-actin promoter could realize an extremely high expression level of Factor VIII.

In order to increase the promoter activity, the plasmids for expression of Factor VIII H-chain or L-chain of the present invention may further comprise various enhancer sequences upstream of the promoter. The enhancer sequence includes a variety of sequences capable of acting as an enhancer in eucaryotic cells, such as SV40 enhancer, cytomegalovirus enhancer, polyoma stem cell enhancer, and the like.

In addition, a Kozak's consensus sequence can be introduced into the initiation codon at the N-terminus of the signal peptide in order to increase the translation efficiency from messenger RNA to an amino acid (M. Kozak, Nucl. Acids Res., 9, 5233, 1981). The present inventors also have found that the introduction of this sequence can increase the expression level of Factor VIII H-chain by several times.

The human Factor VIII expression vector of the present invention preferably comprises a gene sequence comprising the gene coding for the human Factor VIII H-chain or L-chain and the polyadenylation signal situated downstream thereof, including the gene coding for the signal peptide necessary for secretion in animal cells and the chicken β-actin promoter, and a gene sequence comprising a replication origin in $E.\ coli$ and drug resistance gene ligated to the above gene sequence. For example, the human Factor VIII can be obtained in a large amount by inserting the gene coding for the human Factor VIII into the downstream of the chicken β-actin promoter of a vector such as pAG-2 or pCAGS-2 (FIG. 1, 8).

A host cell to which the human Factor VIII expression vector is introduced may be any animal cell in which the human Factor VIII can be expressed. The host cell is preferably such an animal cell that the desired transformant can easily be separated, for example, Chinese hamster ovary (CHO) cell.

The gene fragment for transfection can be introduced into the host cell by the known method, for example, the calcium phosphate method, the DEAE-DEXTRAN method, the Lipofectin method, the electroporation, and the like. For easy selection of the transformant, an animal cell deprived of the marker gene present on the expression vector is used. For example, when CHO cells defected of dihydrofolate reductase (DHFR) gene were cotransfected with the DHFR expression vector such as pSV2-dhfr (Mol. Cell. Biol. 1, 854–864, 1981) and Factor VIII expression vector, the transformed CHO cells in which the DHFR gene was introduced and expressed can be selected and isolated by culturing the cells on a selection culture medium deprived of nucleoside, said CHO cells at the same time have a high possibility of introduction of the human Factor VIII gene. More preferably, a Factor VIII—DHFR coexpression vector wherein the DHFR expression unit is previously incorporated into Factor VIII expression vector is introduced into the host cell, thereby Factor VIII gene and the DHFR gene can be concurrently and efficiently incorporated adjacent to each other on the chromosomal gene of the host cell. In addition, the thus prepared transformant is advantageous in that the amplification of Factor VIII gene can be obtained as mentioned hereinbelow, and as a result, there can be obtained a transformant capable of producing Factor VIII in a large amount.

When the amplifiable gene such as DHFR gene is used, the transformant is cultured under conditions suitable for the gene amplification, in the presence of methotrexate (MTX) in case of the DHFR gene, so that Factor VIII gene incorporated into the transformant is concurrently amplified with the DHFR gene. As a result, the production rate per cell becomes higher and a large amount of Factor VIII can be secreted into the culture medium.

As mentioned above, in the separate expression system of Factor VIII H-chain and L-chain of the present invention, the H-chain or L-chain gene is incorporated into the abovementioned expression plasmid which is then introduced into an animal cell. In this case, the animal cell can be cotransfected with the plasmid for expression of H-chain and the plasmid for expression of L-chain to give a transformant capable of expressing both H and L-chains. The expressed H-chain and L-chain from the transformant form a complex and show a coagulation activity of Factor VIII. Furthermore, when the animal cell is cotransformed with plasmids for expression of H-chain or L-chain wherein the DHFR gene is incorporated and the gene amplification is applied as mentioned above, the expression level of both H and L-chains and eventually of Factor VIII having the coagulation activity can greatly be increased.

The method of introduction of the DNA coding for Factor VIII H-chain and L-chain into a cell in a separate plasmid has been reported in Japanese Patent First Publication (Kokai) No. 282594/1987. However, this publication shows merely a basic concept on the expression of H-chain and L-chain with a separate plasmid but does not describe or even suggest that the expression level of Factor VIII is greatly increased by selecting the molecular size of the H-chain and L-chain like the process of the present invention. The expression level shown in Examples of said publication is quite insufficient for production of Factor VIII on an industrial scale and quite low in comparison with that of the process of the present invention. On the contrary, the process of the present invention employs the plasmids designed for expression of a specific size of the H-chain and L-chain molecules to express Factor VIII and thereby allows for a quite higher expression level which has hitherto never been reported. That is, the present invention provides a technique enabling a high expression of Factor VIII which is well applicable to the industrial production.

In the culture of the transformant, various additives may be added during the culture so that the production efficiency of Factor VIII by the transformant can greatly be increased. Such an additive preferably includes a protein derived from the living body such as albumin (one of plasma protein), von Willebrand factor, etc. Another additive includes a butyrate, polyethylene glycol, sodium selenite, cyclodextrin, a surfactant such as Pluronic F-68, an inhibitor of protease such as ε-aminocaproic acid, aprotinin, phenylmethanesulfonyl fluoride (PMSF), and the like.

The isolation and purification of Factor VIII protein formed and accumulated in the culture medium can be conducted in the usual manner, i.e. after removing the cells, the desired protein can be isolated and purified by concentrating the culture medium and using a suitable combination of the known isolation methods. The known method for isolation and purification includes a method utilizing a difference of solubility such as a salting out and a solvent precipitating method; a method utilizing a difference of a molecular weight such as a dialysis, an ultrafiltration, a gel filtration and an SDS-polyacrylamide gel electrophoresis; a method utilizing a difference of an electric charge such as an ion exchange chromatography; a method utilizing a specific affinity such as an affinity chromatography; a method utilizing a difference of hydrophobicity such as a reversed phase high performance liquid chromatography; a method utilizing a difference of an isoelectric point such as an isoelectric focusing, and the like. The obtained solution containing Factor VIII protein can optionally be lyophilized to powder. The lyophilization can be conducted by using a stabilizing agent such as sorbitol, mannitol, dextrose, an amino acid, maltose, glycerol, human serum albumin (HSA), and the like.

The free H-chain and L-chain formed in the separate expression of the present invention which do not form the complex can be converted into the H-chain–L-chain complex having the coagulation activity by reconstituting the free H and L-chains by allowing to stand in reducing conditions at room temperature in the presence of a bivalent ion in vitro. When this procedure is conducted on the culture supernatant obtained in the separate expression, Factor VIII protein having the activity can be obtained more efficiently.

According to the process of the present invention, the production efficiency of Factor VIII can greatly be increased by the gene recombination procedure in which the high expression level of Factor VIII has been quite difficult. In addition, a non-natural amino acid sequence, which has been produced in the expression of a fused molecule deleted of B-domain, cannot be formed in the separate expression system of the present invention due to its principle of the process, and hence, a quite safe Factor VIII preparation with no risk of heteroantigenicity can be obtained.

The present invention is explained in more detail by the following Examples but should not be construed to be limited thereto.

EXAMPLE 1

Construction of expression plasmid; pAG.dhfr

Figure 2:
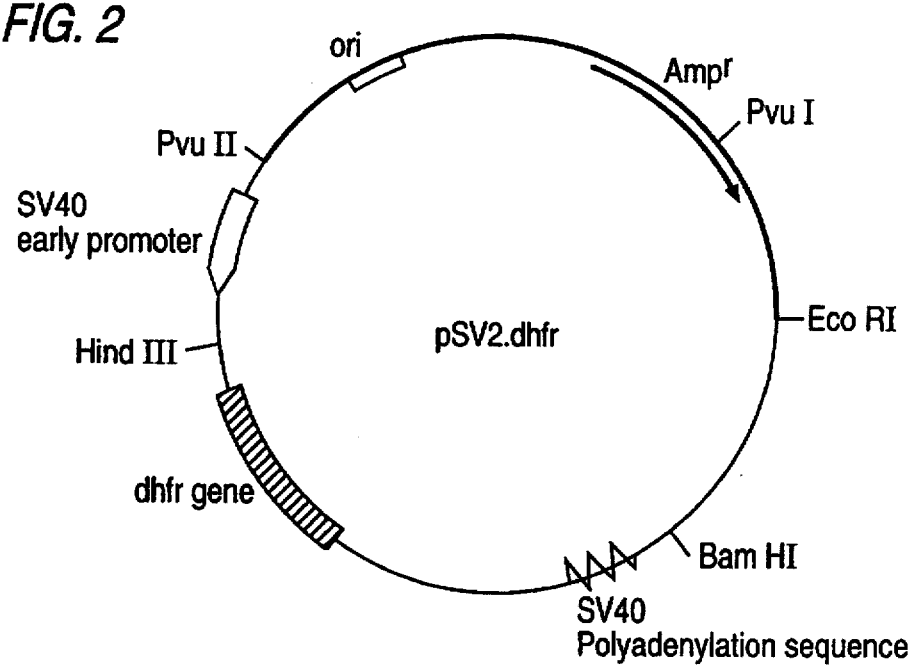
FIG. 2 illustrates the structure of the plasmid pSV2.dhfr.
Figure 3:
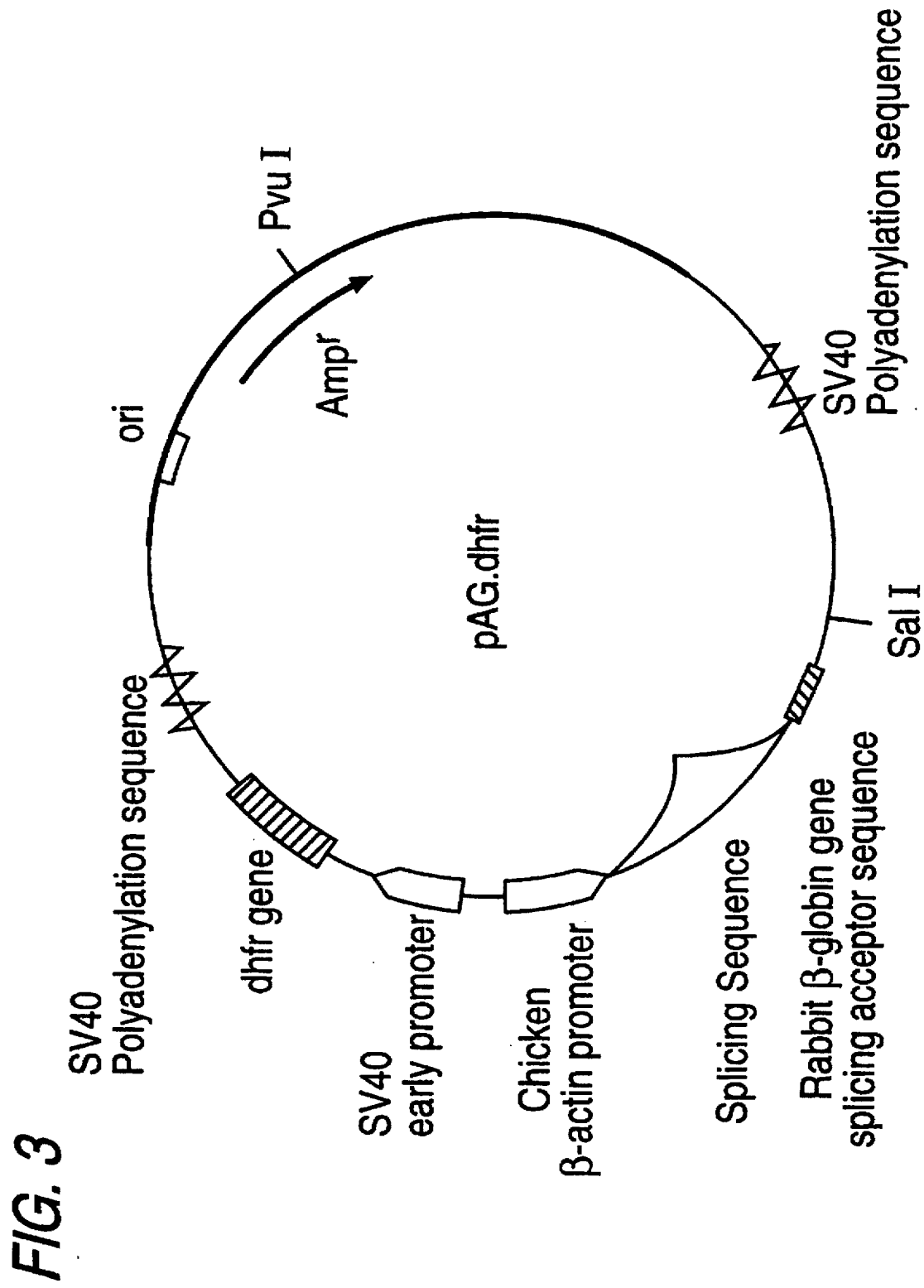
FIG. 3 illustrates the structure of the plasmid pAG.dhfr constructed in Example 1.

To achieve an efficient gene expression in an animal cell, there was constructed an expression plasmid wherein an expression cassette having β-actin promoter and an expression cassette for dihydrofolate reductase (DHFR) were introduced into the same plasmid. The plasmid pAG-2 (Japanese Patent First Publication (Kokai) No. 168087/1991; FIG. 1) which contains the β-actin promoter expression cassette was digested with restriction enzyme XhoI and blunt-ended with T4-DNA polymerase. The DHFR expression cassette was obtained from the expression plasmid pSV2-DHFR (Mol. Cell. Biol., 1, 854–864, 1981; FIG. 2).

pSV2-DHFR was digested with restriction enzymes PvuII and EcoRI and blunt-ended with T4-DNA polymerase. Then, fragments were subjected to an agarose gel electrophoresis and a DNA fragment of about 2.7 kbp containing the DHFR expression cassette was extracted from the gel. This fragment was inserted into the XhoI site of the above blunt-ended pAG-2 to construct an expression plasmid paG.dhfr (FIG. 3).

EXAMPLE 2

Construction of FVIII H-chain 740 type expression plasmid pAG.H740.dhfr

Figure 4:
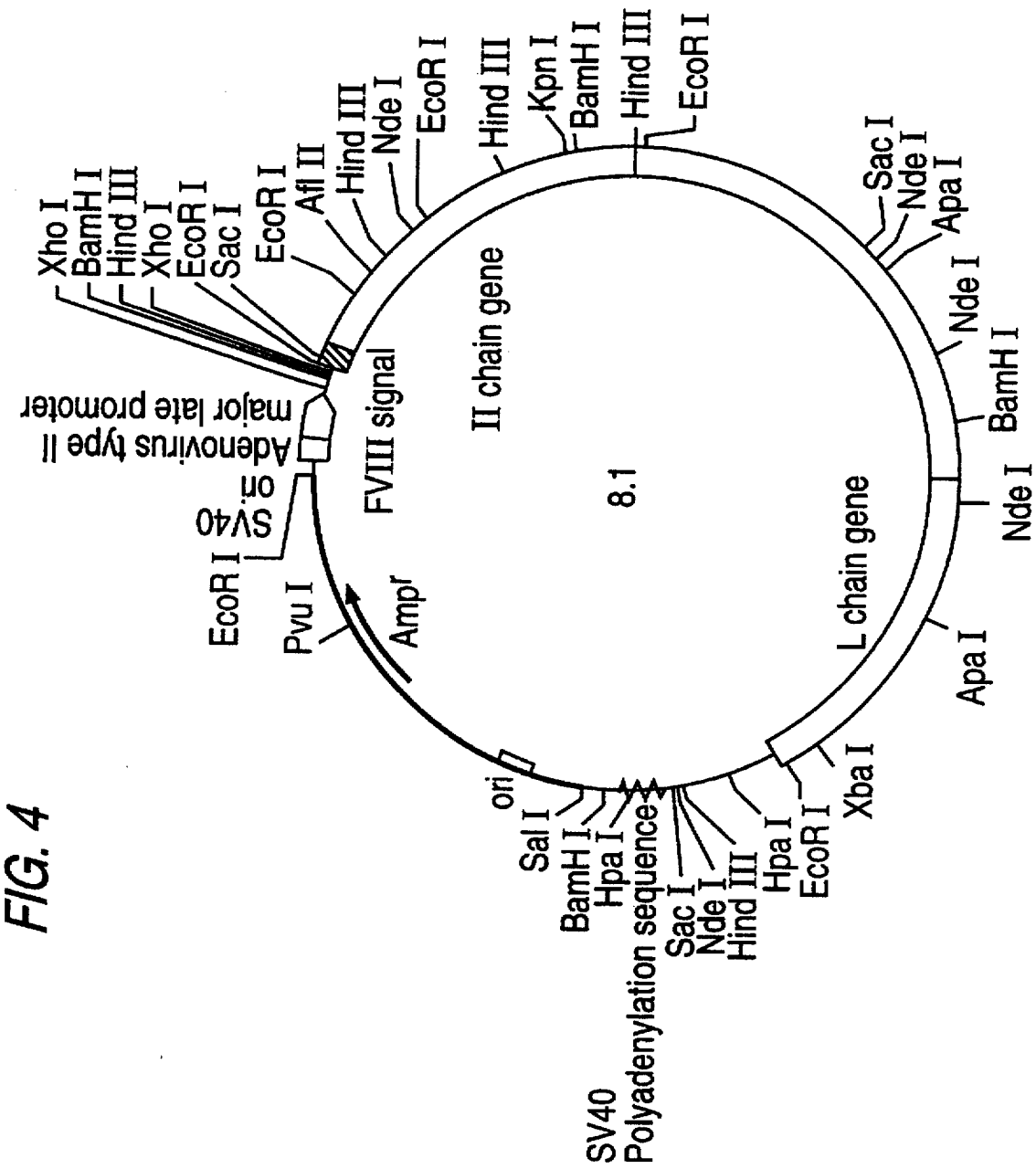
FIG. 4 illustrates the structure of the plasmid 8.1.

Using the Polymerase Chain Reaction (PCR) method utilizing the expression plasmid 8.1 containing the full length of Factor VIII (hereinafter referred to as "FVIII") cDNA (Japanese Patent First Publication No. 503275/1983; FIG. 4) as a template, the termination codon was introduced immediately downstream of the DNA coding for the 740th Arginine. The following two synthetic olygomers were employed as a primer of PCR. The primer 2 was modified at the 5'-end in order to induce a mutation so that the termination codon is introduced immediately downstream of the DNA coding for the 740th Arginine and the restriction site SalI for cloning is introduced downstream thereof.

Primer 1(SEQ ID NO:3): 5'-AGAGATCTAGCTTCA
Primer 2(SEQ ID NO:4): 5'-CCGGTCGACCCTCATCTTGGTTCAATGGCA The PCR reaction was conducted in 25 cycles, each cycle comprising a denaturation reaction (95° C., 1 min.), an annealing reaction (55° C., 2 min.) and a polymerase reaction (72° C., 2 min.). The polymerase reaction in the last cycle was conducted at 72° C. for 5 minutes.

After completion of the reaction, a phenol extraction and an ethanol precipitation were carried out and then the PCR product was digested with restriction enzymes KpnI and SalI. Then, fragments were subjected to an agarose gel electrophoresis and a desired 0.5 kbp fragment was extracted from the gel. In order to ligate this fragment with the DNA coding for the N-terminal portion of the H-chain, the plasmid 8.1 (FIG. 4) was digested with restriction enzymes KpnI and SalI and then treated with an alkaline phosphatase derived from calf small intestine to dephosphorylate the cleaved ends. The fragments were subjected to an agarose gel electrophoresis and a 5.5 kbp fragment coding for the 5'-end portion of the FVIII was extracted from the gel. This fragment and the above fragment were ligated to cyclize with T4-DNA ligase to construct a plasmid p11.740. The region obtained by the PCR reaction was sequenced by the dideoxy sequencing method and the correct insertion of the termination codon and the like was confirmed.

Figure 5:
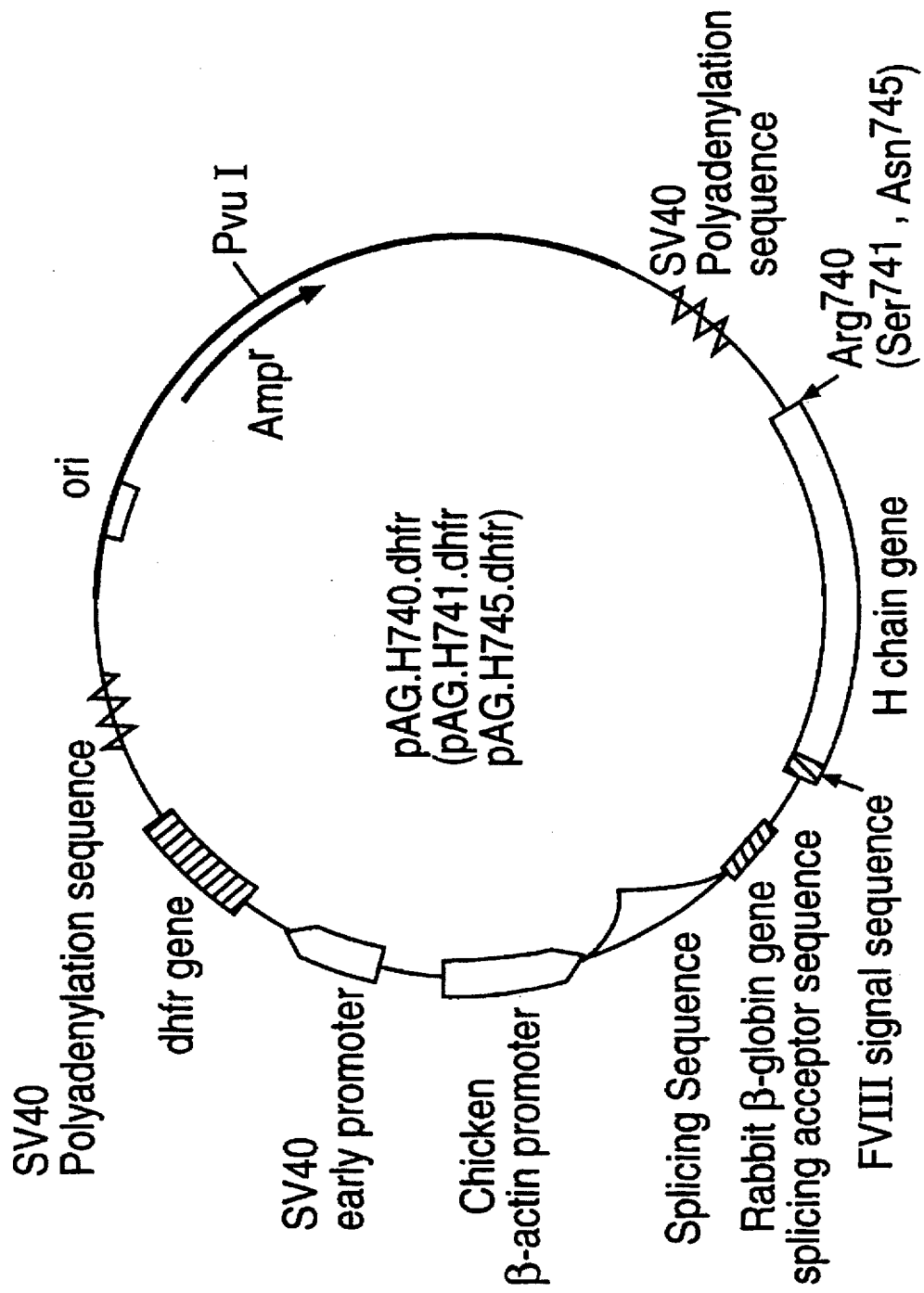
FIG. 5 illustrates the structure of the plasmids pAG.H740.dhfr, pAG.H741.dhfr and pAG.H745.dhfr constructed in Example 2, Example 3 and Example 4, respectively.

The plasmid p11.740 was digested with restriction enzymes XhoI and SalI. The obtained fragments were subjected to an agarose gel electrophoresis and about 2.3 kbp fragment coding for the DNA coding for the FVIII H-chain 90 k was extracted from the gel. The chicken β-actin promoter expression plasmid pAG.dhfr (FIG. 3) constructed in Example 1 was digested with restriction enzyme SalI and then treated with an alkaline phosphatase derived from calf small intestine to dephosphorylate the cleaved ends. This linearized plasmid and the above H-chain fragment were ligated to cyclize with T4-DNA ligase to construct an H-chain 740 type expression plasmid pAG.H740.dhfr (FIG. 5).

EXAMPLE 3

Construction of FVIII H-chain 741 type expression plasmid pAG.H741.dhfr

The plasmid pUC18 (manufactured by Takara Shuzo; #3218) was digested with restriction enzyme HindIII, blunt-ended with T4-DNA polymerase and ligated to cyclize with T4-DNA ligase to construct a plasmid pUC.Hn wherein the HindIII site of the plasmid pUC18 was deleted. Then, the expression plasmid 8.1 (FIG. 4) containing the full length of FVIII cDNA was digested with restriction enzymes KpnI-XbaI. The obtained fragments were subjected to an agarose gel electrophoresis and 5.1 kbp fragment coding for the C-terminal portion of the H-chain, the B-domain and the N-terminal portion of the L-chain was extracted from the gel. This DNA fragment was ligated to cyclize with a KpnI-XbaI fragment of pUC.Hn with T4-DNA ligase to construct pUC.11.KX.

The plasmid pUC.11.KX was digested with restriction enzyme HindIII, blunt-ended with T4-DNA polymerase and thereto was inserted a phosphorylated NcoI linker (manufactured by Takara Shuzo; #4765P; 10mer) to cyclize with T4-DNA ligase to construct pUC11.KX-Nco wherein the termination codon was introduced just downstream of the 741st Serine. The plasmid pUC.11.KX-Nco was digested with restriction enzyme NcoI and blunt-ended with T4-DNA polymerase and thereto was inserted a phosphorylated SalI linker (manufactured by Takara Shuzo; #4780P) to cyclize with T4-DNA ligase to construct pUC.11.KX.H741.

The plasmid pCU.11.KX.H741 was digested with restriction enzymes KpnI-SalI. The obtained fragments were subjected to an agarose gel electrophoresis and an fragment of about 0.5 kbp was extracted from the gel. The plasmid 8.1 (FIG. 4) was digested with restriction enzymes KpnI-SalI. The obtained fragments were subjected to an agarose gel electrophoresis and a fragment of about 5.5 kbp containing a replication origin (ori) in *E. coli* and an ampicillin resistance gene was extracted from the gel. This DNA fragment and the above 0.5 kbp fragment were ligated with T4-DNA ligase to cyclize to construct p11.H741. The plasmid p11.H741 was digested with restriction enzymes XhoI-SalI. The obtained fragments were subjected to an agarose gel electrophoresis and a DNA fragment of about 2.3 kbp coding for FVIII H-chain was extracted from the gel. This fragment was inserted into the SalI site of the expression plasmid pAG.dhfr (FIG. 3) constructed in Example 1 to construct a 741 type expression vector pAG.H741.dhfr (FIG. 5).

EXAMPLE 4

Construction of FVIII H-chain 90 k 745 type expression plasmid pAG.H745.dhfr

The plasmid pUC18 was digested with restriction enzyme EcoRI, blunt-ended with T4-DNA polymerase and ligated to cyclize with T4-DNA ligase to construct a plasmid pUC.En wherein the EcoRI site of the plasmid pUC18 was deleted.

Then, the expression plasmid 8.1 (FIG. 4) obtained in Example 3 was digested with restriction enzymes KpnI and XbaI. The obtained fragment was inserted into the KpnI-XbaI site of the above pUC.En to construct pUC.11.KXEn. The plasmid pUC.11.KXEn was digested with restriction enzyme EcoRI, blunt-ended with T4-DNA polymerase and thereto was inserted a phosphorylated NcoI linker (manufactured by Takara Shuzo; #4765P) to cyclize with T4-DNA ligase to construct pUC11.KXEn-Nco wherein the termination codon was introduced just downstream of the 745th Asparagine. The plasmid pUC.11.KXEn-Nco was digested with restriction enzyme NcoI and blunt-ended with T4-DNA polymerase and thereto was inserted a phosphorylated SalI linker to cyclize with T4-DNA ligase to construct pUC.11.KX.H745.

The plasmid pCU.11.KX.H745 was digested with restriction enzymes KpnI-SalI. The obtained fragments were subjected to an agarose gel electrophoresis and an fragment of about 0.5 kbp was extracted from the gel. The plasmid 8.1 (FIG. 4) was digested with restriction enzymes KpnI-SalI. The obtained fragments were subjected to an agarose gel electrophoresis and a fragment of about 5.5 kbp containing a replication origin (ori) in *E. coli* and an ampicillin resistance gene was extracted from the gel. This DNA fragment and the above 0.5 kbp fragment were ligated to cyclize with T4-DNA ligase to construct p11.H745. The plasmid p11.H745 was digested with restriction enzymes XhoI-SalI. The obtained fragments were subjected to an agarose gel electrophoresis and a DNA fragment of about 2.3 kbp coding for the FVIII H-chain was extracted from the gel. This fragment was inserted into the SalI site of the expression plasmid pAG.dhfr (FIG. 3) constructed in Example 1 to construct a 745 type expression vector pAG.H745.dhfr (FIG. 5).

EXAMPLE 5

Transfection of CHO cell with H-chain 740 type, 741type and 745 type expression plasmids pAG.H740.dhfr, pAG.H741.dhfr and pAG.H745.dhfr, and gene amplification thereof In order to determine the expression level of H-chain alone, CHO cells were transformed with the H-chain expression plasmids.

The H-chain expression plasmids pAG.H740.dhfr (Example 2), pAG.H741.dhfr (Example 3) and pAG.H745.dhfr (Example 4) (FIG. 5) were previously digested with restriction enzyme PvuI to linearize. DHFR-deficient CHO cells DG44 (Somatic Cell and Molecular Genetics 12, 555–565, 1986) were inoculated onto a 6-well multiplate (manufactured by Falcon; #3046) at $3 \times 10^5$ cells/well using a serum medium (MEM-alpha medium containing 10% fetal calf serum) and incubated in $CO_2$ incubator overnight. The introduction of DNA into the cells was conducted by using Lipofectin reagent manufactured by BRL. The above linearized plasmid (10 μg/25 μl) was mixed with an equivalent volume of Lipofectin reagent (manufactured by BRL; #8929SA) using a polystyrene tube (manufactured by Falcon; #2054) was charged with an aqueous solution (25 μl) containing and thereto was added. The mixture was stirred and then allowed to stand at room temperature for 15 minutes. CHO cells DG44 were washed twice with PBS(−) before use and the culture medium was replaced with 2 ml of ASF culture medium 104 (manufactured by Ajinomoto; #RITC578A). To the cells was added dropwise the DNA-Lipofectin solution and the cells were incubated in $CO_2$ incubator overnight. The next day, the cells were washed twice with PBS(−) and cultured on the above serum culture medium overnight. Then, the culture medium was replaced with 3 ml of DHFR selection medium (nucleoside free MEM-alpha medium containing 10% dialyzed fetal calf serum) and the culture was continued while replacing the culture medium with this selection medium every 3 to 4 days to select DHFR(+) cells. After 10 days, the FVIII H-chain antigen in the culture medium was determined by the following method.

The transformed cells were inoculated onto a 6-well multiplate at $1 \times 10^6$ cells/well and cultured overnight. The next day, the culture medium was replaced with a fresh culture medium and the FVIII antigen in the culture medium was determined. The measurement of the antigen was conducted by a sandwich ELISA using a monoclonal antibody specific for the H-chain. The results are shown in Table 1.

Furthermore, the gene amplification was conducted on the transformed cells. The cells were grown on the above selection culture medium overnight and the culture medium was replaced with a selection culture medium containing 10 nM methotrexate (MTX; manufactured by Wako Pure Chemical Industries, Ltd; #133-08083). The culture was continued while replacing the culture medium every 3 to 4 days and thereby only MTX resistant cells were able to grow. After about 3 weeks, the expression level of the H-chain antigen was measured by the same method as above. The results are shown in Table 1.

TABLE 1

| | Expression level of H-chain antigen | |
|---|---|---|
| Plasmid | Before addition of MTX | 10 nM MTX resistant cells |
| pAG.H740.dhfr | n.d. | 2 |
| pAG.H741.dhfr | 10 | 60 |
| pAG.H745.dhfr | 24 | 150 |

Unit: mU/day/$10^6$ cells

EXAMPLE 6

Construction of FVIII L-chain 1649 type expression plasmid pAG.LE.dhfr

The FVIII signal sequence was linked to the upstream of the 1649th Glutamic acid at the N-terminus of the L-chain. PCR method was used for the construction. The DNAs coding for the signal sequence and for the N-terminal portion of the L-chain were amplified by the PCR method. For the amplification of the signal sequence portion, there were used a synthetic oligonucleotide comprising 20 base pairs corresponding to the vicinity of the restriction enzyme XhoI site upstream of the signal sequence as the first primer, and a synthetic oligonucleotide comprising 20 base pairs corresponding to the 3'-terminus of the signal sequence as the second primer, and about 100 base pairs between these areas were amplified.

Primer 1(SEQ ID NO:5); 5'-ACTGGATCCAAGCTT
Primer 2(SEQ ID NO:6); 5'-ACTAAAGCAGAATCG The end of the primer 2 was phosphorylated with T4 polynucleotide kinase before the PCR reaction.

The following two synthetic oligonucleotides were used for amplification of the N-terminal portion of the L-chain.

Primer 3(SEQ ID NO:7); 5'-GAAATAACTCGTACT
Primer 4(SEQ ID NO:8); 5'-AGCTTTGGGGCCCAC The plasmid 8.1 (FIG. 4) was used as a template DNA for each PCR reaction. The PCR reaction was conducted under the same conditions as in Example 2. After the reaction, the phenol extraction and the ethanol precipitation were carried out. The PCR products for the signal portion and for the N-terminal portion of the L-chain were subjected to a polyacrylamide gel electrophoresis and an agarose gel electrophoresis, respectively, and DNA fragments of a desired length were extracted from the gel. Then, in order to remove Adenine added at the 3'-end due to the side reaction of Taq DNA polymerase used in the PCR reaction, the obtained DNA fragments were blunt-ended with T4-DNA polymerase and ligated with T4-DNA ligase. In order to obtain a DNA fragment in which the signal portion and the N-terminal portion of the L-chain are correctly linked, the PCR reaction was again carried out on a part of the mixture after the reaction using the primer 1 for amplification of the signal portion and the primer 4 for amplification of the L-chain. After the reaction, the PCR reaction solution was subjected to the phenol extraction and the ethanol precipitation. The PCR products were digested with restriction enzymes XhoI and ApaI, the obtained fragments were subjected to an agarose gel electrophoresis and a DNA fragment of a desired length was extracted from the gel. A phage vector pBluescript II KS+ (manufactured by Stratagene; #212207) was digested with restriction enzymes XhoI and ApaI and the ends were dephosphorylated with an alkaline phosphatase derived from calf small intestine. The above fragment was subcloned into this vector by ligation with T4-DNA ligase and cyclization to give a plasmid pBS.LE.

The single chain phage DNA of the plasmid pBS.LE was obtained by the usual method using a helper phage and a DNA-sequencing was conducted by the dideoxy sequencing method. As a result, it was confirmed that the signal portion and the L-chain portion were correctly ligated in the same open reading frame and the nucleotide sequence was also correct.

Then, in order to construct the whole length of the L-chain, the plasmid 8.1 (FIG. 4) was digested with restriction enzyme HpaI and ligated to cyclize with T4-DNA ligase under the presence of a phosphorylated XhoI linker to construct a plasmid p11.3X wherein the SV40 polyadenylation portion was deleted and a new restriction enzyme XhoI recognition site was introduced thereto. The plasmid pBS.LE was digested with restriction enzymes SacI and NdeI, the obtained fragments were subjected to an agarose gel electrophoresis and a DNA fragment of about 1.3 kbp coding for the signal portion and the N-terminal portion of the L-chain was extracted from the gel. The plasmid p11.3X was digested with restriction enzymes SacI and NdeI and the ends were dephosphorylated with an alkaline phosphatase derived from calf small intestine. The fragments were subjected to an agarose gel electrophoresis and a DNA fragment of about 5.7 kbp coding for the C-terminal portion of the L-chain and the sequence derived from $E.\ coli$ was extracted from the gel. This fragment was ligated to the above 1.3 kbp fragment with T4-DNA ligase to cyclize to construct p11.LE.3X.

Figure 6:
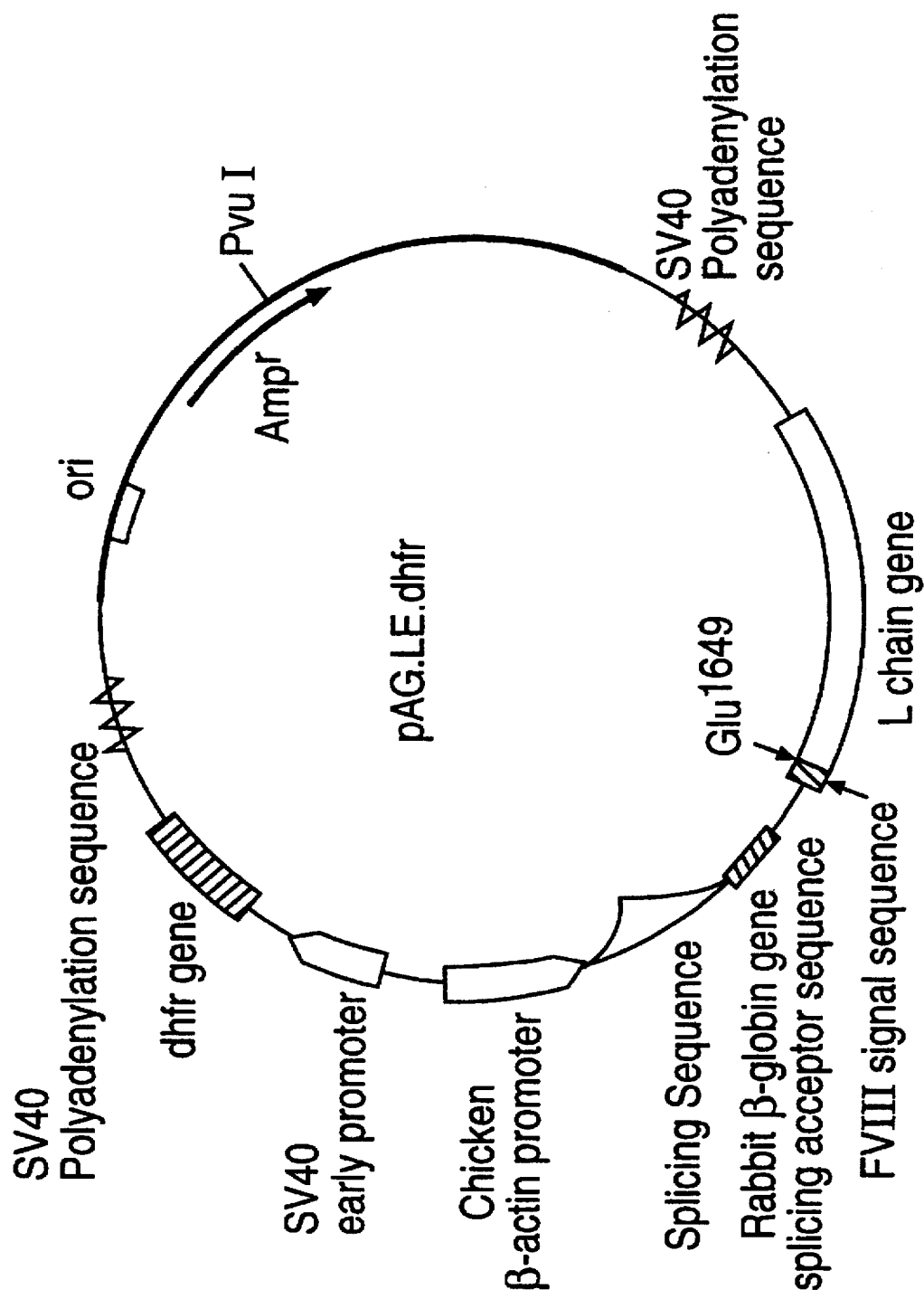
FIG. 6 illustrates the structure of the plasmid pAG.LE.dhfr constructed in Example 6.

The plasmid p11.LE.3X was digested with restriction enzyme XhoI, the fragments were subjected to an agarose gel electrophoresis and a DNA fragment of 2.5 kbp coding for the L-chain was extracted from the gel. The expression plasmid pAG.dhfr (FIG. 3) constructed in Example 1 was digested with restriction enzyme SalI and the ends were dephosphorylated and thereto was inserted the above 2.5 kbp DNA fragment with T4-DNA ligase to construct an L-chain 1649 type expression plasmid pAG.LE.dhfr (FIG. 6).

EXAMPLE 7

Construction of FVIII L-chain 1563 type expression plasmid pAG.LD.dhfr

The original signal sequence of FVIII was introduced immediately upstream of the 1563rd Aspartic acid. Since the BamHI site is present at the portion coding for the 1563rd Aspartic acid, the plasmid pUC11.KX used in Example 3 was digested with restriction enzyme BamHI and blunt-ended with T4-DNA polymerase. The fragments were subjected to an agarose gel electrophoresis and a fragment of 4 kbp was extracted from the gel. This fragment was ligated to the PCR fragment of about 100 bp coding for the signal portion of FVIII prepared in Example 6 to cyclize to construct a plasmid pUC.11.LD.KX. The plasmid pUC.11.LD.KX was digested with restriction enzymes KpnI-XbaI, the fragments were subjected to an agarose gel electrophoresis and a fragment of about 2.3 kbp was extracted from the gel.

The plasmid p11.3X constructed in Example 6 was digested with restriction enzymes KpnI-XbaI, the fragments were subjected to an agarose gel electrophoresis and a fragment of about 6.4 kbp containing the replication origin (ori) in $E.\ coli$ and the ampicillin resistance portion was extracted from the gel. This fragment was ligated to the above 2.3 kbp fragment to cyclize to construct a plasmid p11.LD.3X.

Figure 7:
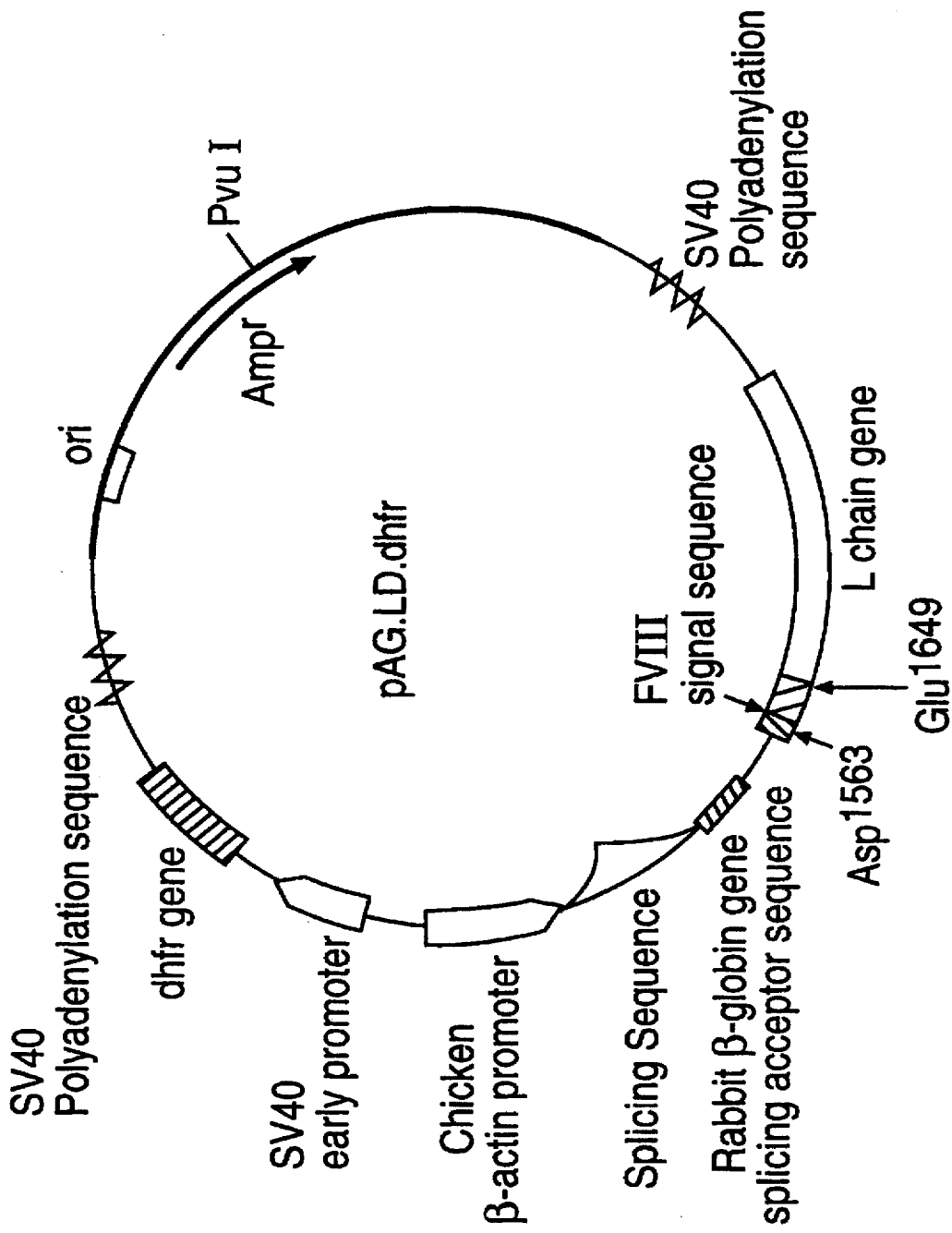
FIG. 7 illustrates the structure of the plasmid pAG.LD.dhfr constructed in Example 7.

The plasmid p11.LD.3X was digested with restriction enzyme XhoI, the fragments were subjected to an agarose gel electrophoresis and a DNA fragment of about 2.8 kbp coding for the L-chain was extracted from the gel. The expression plasmid pAG.dhfr (FIG. 3) was digested with restriction enzyme SalI, the ends were dephosphorylated with an alkaline phosphatase derived from calf small intestine and thereto was inserted the above 2.8 kbp DNA fragment to cyclize to construct an L-chain expression plasmid pAG.LD.dhfr (FIG. 7).

EXAMPLE 8

Transfection of CHO cell with the L-chain expression plasmids and gene amplification thereof The expression level of antigen was also determined on the L-chain alone. The 1649 type expression plasmid pAG.LE.dhfr (FIG. 6) constructed in Example 6 and the 1563 type expression plasmid pAG.LD.dhfr (FIG. 7) constructed in Example 7 were previously digested with restriction enzyme PvuI to linearize.

The preparation of cells and the transfection were conducted in the same manner as in Example 4. After selection of DHFR(+) by culturing on the DHFR selection culture medium, the expression level of the L-chain antigen was measured by a sandwich ELISA using an L-chain-specific monoclonal antibodies. The results are shown in Table 2.

The gene amplification by MTX was also carried out on these transformed cells as in the case of the H-chain. The results are shown in Table 2.

TABLE 2

| Plasmid | Expression level of L-chain antigen | |
|---|---|---|
| | Before addition of MTX | 20 nM MTX resistant cells |
| pAG.LE.dhfr | 200 | 2,400 |
| pAG.LD.dhfr | 1,200 | 12,300 |

Unit; mU/day/$10^6$ cells

EXAMPLE 9

Analysis of expression products in L-chain 1649 type and 1563 type expression plasmids In order to study as to whether a precise processing is occurred in the L-chain expression, especially in the expression of the 1649 type, the radio immunoprecipitation analysis was conducted.

The 1649 type expression cells and the 1563 type expression cells obtained in Example 8 were inoculated onto a 6-well multiplate and cultured on a DHFR selection culture medium containing 3.7 MBq of [$^{35}$S] methionine (Amersham Japan, SJ1015) overnight. The radiolabelled FVIII protein in the medium was specifically precipitated using a monoclonal antibody specific for the L-chain. The precipitates were subjected to an SDS polyacrylamide gel electrophoresis, and after fixation and fluorography, to an autoradiography to detect the protein bands.

Figure 12:
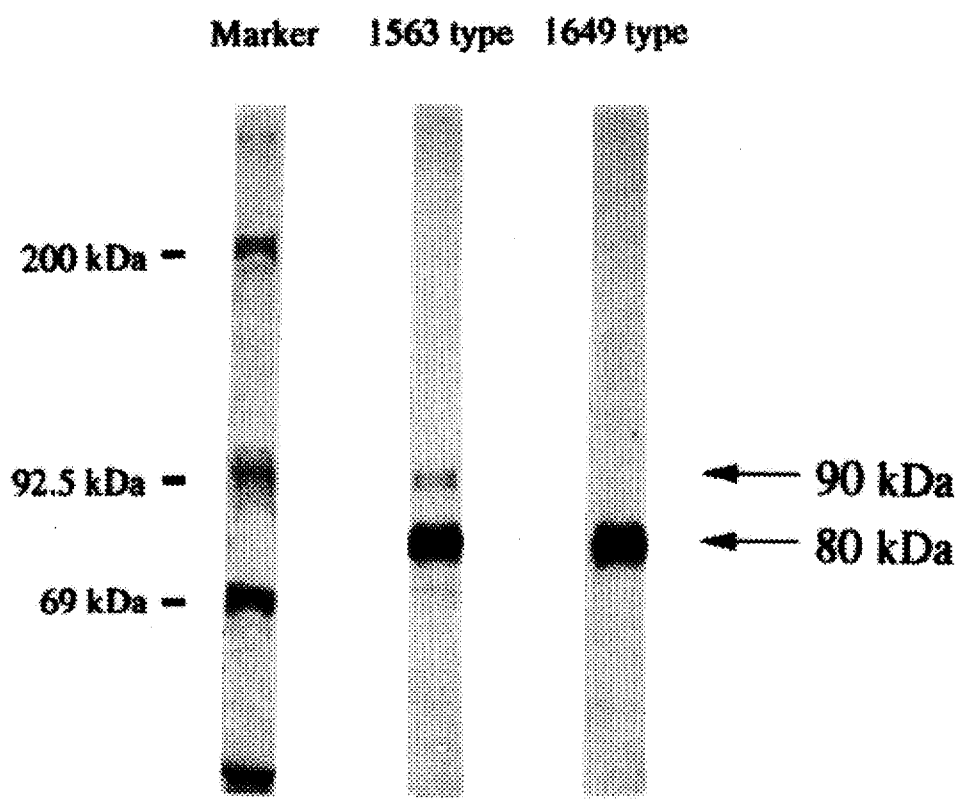
FIG. 12 shows the result of the immunoprecipitation conducted in Example 9.

The results are shown in FIG. 12. As is clear from FIG. 12, when the 1563 type L-chain was expressed, the most protein was expressed as an 80 k dalton protein wherein the B-domain derived 86 amino acid portion was processed. The band patterns of protein at the 80 k dalton portion were almost the same in the 1649 type and the 1563 type. The 1563 type produced minor bands at approximately 90 K dalton portion, which was densitometically less than 5% of the 80K dalton portion.

CHO cells capable of expressing the L-chain 1563 type at a high expression level were cultured in Cell Factory 10 (manufactured by Nunc; #164327) and the culture medium was concentrated through membrane. Then, the protein was purified by immunoaffinity chromatography using an L-chain-specific monoclonal antibody. The obtained L-chain was subjected to an SDS polyacrylamide gel electrophoresis and then electrophoretically transferred to polyvinylidene difluoride membrane. After staining with Amido Black 10B, a desired main band of 80 k dalton portion and a minor band of 90 k dalton portion were cut from the membrane and the amino acid sequence at the N-terminus was determined by automatic Edman method using a gas phase protein sequencer (Applied Biosystems 477A Protein Sequencer). The results are shown as follows:

The amino acid sequence at the N-terminus of the L-chain 80 k: Glu-Ile-Thr-Arg-Thr-Thr-Leu-Gln- The amino acid sequence at the N-terminus of the L-chain 90 k: Asp-Pro-Leu-Ala-Trp-Asp-Asn-His- As a result, the amino acid sequence at the N-terminus of the 1563 type L-chain 80 k dalton portion main band was a sequence starting from the 1649th Glutamic acid, and hence, identified to be the same as the amino acid sequence at the N-terminus of the natural L-chain 80 k dalton protein derived from plasma. The amino acid sequence at the N-terminus of the 90 k dalton portion band detected in the expression of the 1563 type L-chain was also analyzed in the same way. The sequence Asp-Pro-Leu was detected from the 90 k dalton portion and corresponded to Asp1563-Ile1565 of FVIII. This results show that the signal peptide was correctly cleaved.

EXAMPLE 10

Cotransfecion of CHO cell DG44 with the H-chain expression plasmid and L-chain expression plasmid CHO cells DG44 were cotransfected with the H-chain expression plasmid constructed in Examples 2, 3 and 4 and the L-chain expression plasmid constructed in Examples 6 and 7.

The transformation was carried out in 6 combinations of the H-chain expression plasmid pAG.H740.dhfr (Example 2), pAG.H741.dhfr (Example 3) or pAG.H745.dhfr (Example 4) and the L-chain expression plasmid pAG.LE.dhfr (Example 6) or pAG.LD.dhfr (Example 7). The plasmids were previously digested with restriction enzyme PvuI to linearize. CHO cells DG44 were inoculated onto a 6-well multiplate for cell culture at $3 \times 10^5$ cells/well using a serum culture medium (MEM alpha medium containing 10% fetal calf serum) and cultured in $CO_2$ incubator overnight. The introduction of DNA into the cells was conducted by using Lipofectin reagent manufactured by BRL as in Example 5. The above linearized plasmids for H-chain and L-chain (each 7 μg) were mixed in 25 μl $H_2O$ using polystyrene tube, and then mixed with an equivalent volume of Lipofectin reagent. The mixture was allowed to stand at room temperature for 15 minutes. CHO cells DG44 were washed twice with PBS(−) before use and the culture medium was replaced with 2 ml of a serum free culture medium (ASF culture medium 104). The DNA-Lipofectin solution was added dropwise to the cells and the cells were incubated in $CO_2$ incubator overnight. The next day, the cells were washed twice with PBS(−) and cultured on the above-serum culture medium overnight. Then, the culture medium was replaced with 3 cc of a DHFR selection medium (nucleoside free MEM-alpha medium containing 10% dialyzed fetal calf serum) and the culture was continued to select DHFR(+) cells wherein the DNA was introduced. The culture was continued while replacing the culture medium with this selection medium every 3 to 4 days and thereby only DHFR(+) cells could grow. After 2 weeks, the FVIII activity in the medium was determined by the following method.

The transformed cells were inoculated onto a 6-well multiplate for cell culture at $1 \times 10^6$ cells/well and cultured overnight. The next day, the culture medium was replaced with a fresh culture medium and the FVIII activity in the medium was determined after 24 hours. The measurement of the activity was conducted using Coatest kit manufactured by Kabi. The results are shown in Table 3.

TABLE 3

| H-chain expression plasmid + L-chain expression plasmid | Factor VIII activity |
|---|---|
| pAG.H740.dhfr + pAG.LE.dhfr | 2.4 |
| pAG.H740.dhfr + pAG.LD.dhfr | 3.0 |
| pAG.H741.dhfr + pAG.LE.dhfr | 12.4 |
| pAG.H741.dhfr + pAG.LD.dhfr | 15.7 |
| pAG.H745.dhfr + pAG.LE.dhfr | 16.7 |
| pAG.H745.dhfr + pAG.LD.dhfr | 25.1 |

Unit; mU/day/$10^6$ cells

EXAMPLE 11

Figure 8:
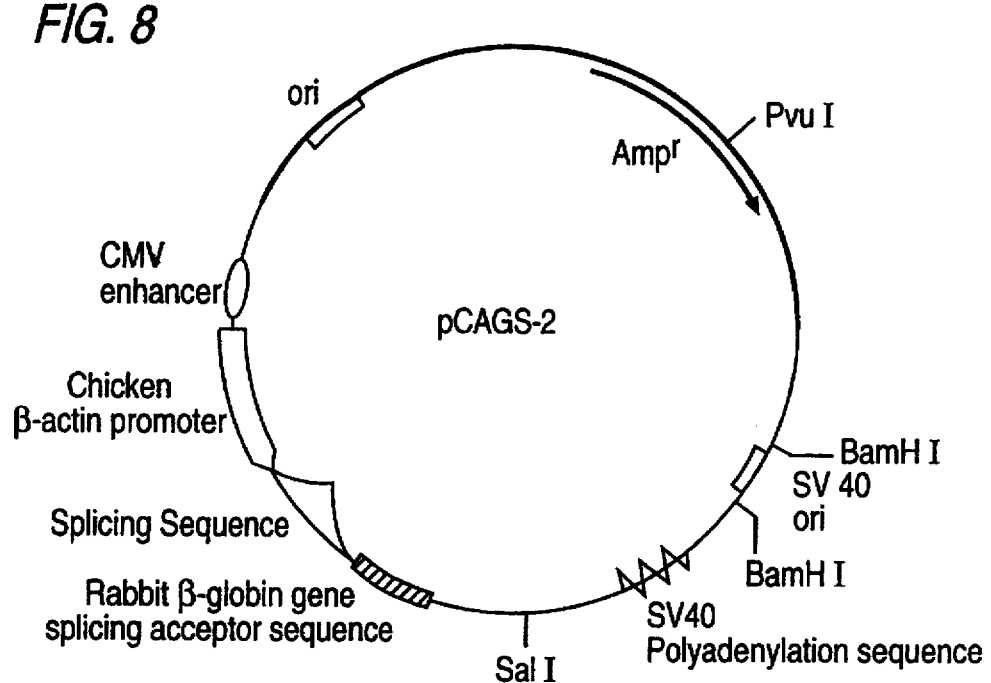
FIG. 8 illustrates the structure of the plasmid pCAGS-2.
Figure 9:
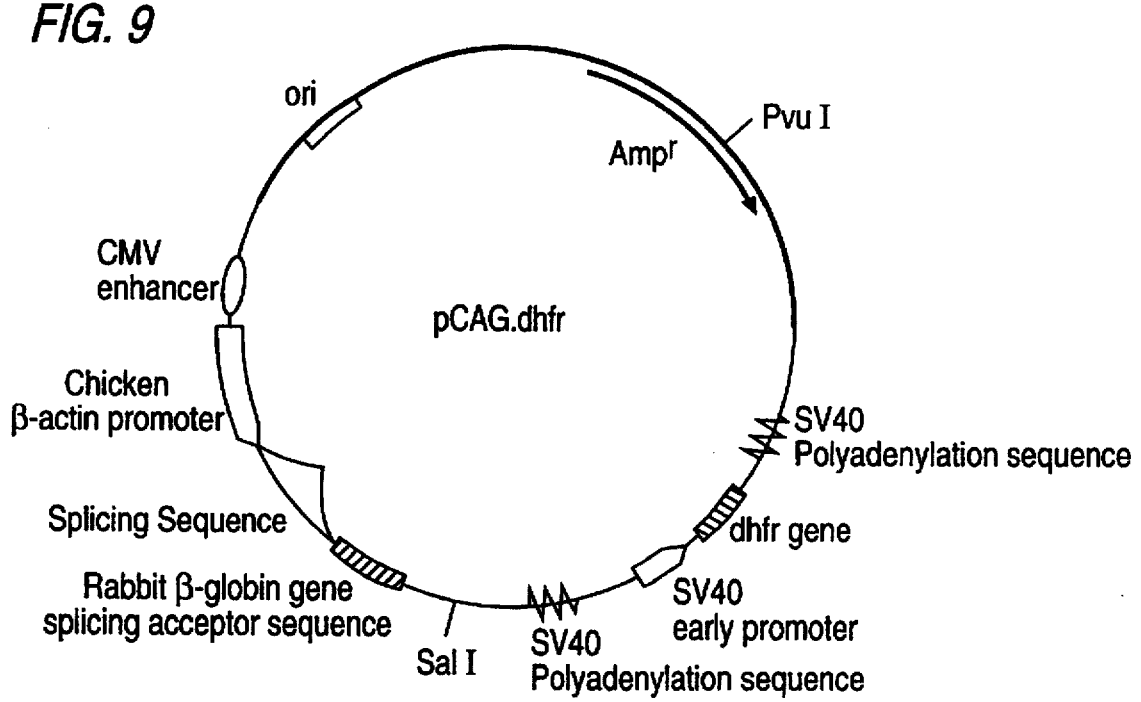
FIG. 9 illustrates the structure of the plasmid pCAG.dhfr constructed in Example 11.

Construction of expression plasmid pCAG.dhfr wherein enhancer sequence capable of enhancing promoter activity of β-actin promoter In order to increase the expression level of FVIII, the DHFR expression cassette for gene amplification was introduced into the expression plasmid pCAGS-2 (Japanese Patent First Publication No. 168087/1991; FIG. 8), in which an enhancer sequence of cytomegalovirus (CMV) was introduced into the upstream of the β-actin promoter in order to further increase the promoter activity of the β-actin promoter used in the conventional plasmid, in the same manner as in Example 1. The DHFR expression cassette was derived from the expression plasmid pSV2-DHFR as in Example 1.

pSV2-DHFR was digested with restriction enzyme PvuII and ligated to cyclize with T4-DNA ligase under the presence of phosphorylated BamHI linker (manufactured by Takara Shuzo; #4610P) to construct pSV2-DHFR2B. The plasmid pSV2-DHFR2B was digested with restriction enzyme BamHI, the obtained fragments were subjected to an agarose gel electrophoresis and a DNA fragment of about 1.7 kbp containing the DHFR expression cassette was extracted from the gel. The above plasmid pCAGS-2 was digested with restriction enzyme BamHI and the ends were dephosphorylated with an alkaline phosphatase derived from calf small intestine. The treatment with restriction enzyme BamHI removed the SV40 replication origin of 0.3 kbp in pCAGS-2. The obtained BamHI-digested pCAGS-2 fragment and the above DHFR fragment were ligated to cyclize with T4-DNA ligase to construct an expression plasmid pCAG.dhfr (FIG. 9) containing the DHFR expression cassette.

EXAMPLE 12

Construction of FVIII H-chain 741 type expression plasmid pCAG.H741.dhfr

Figure 10:
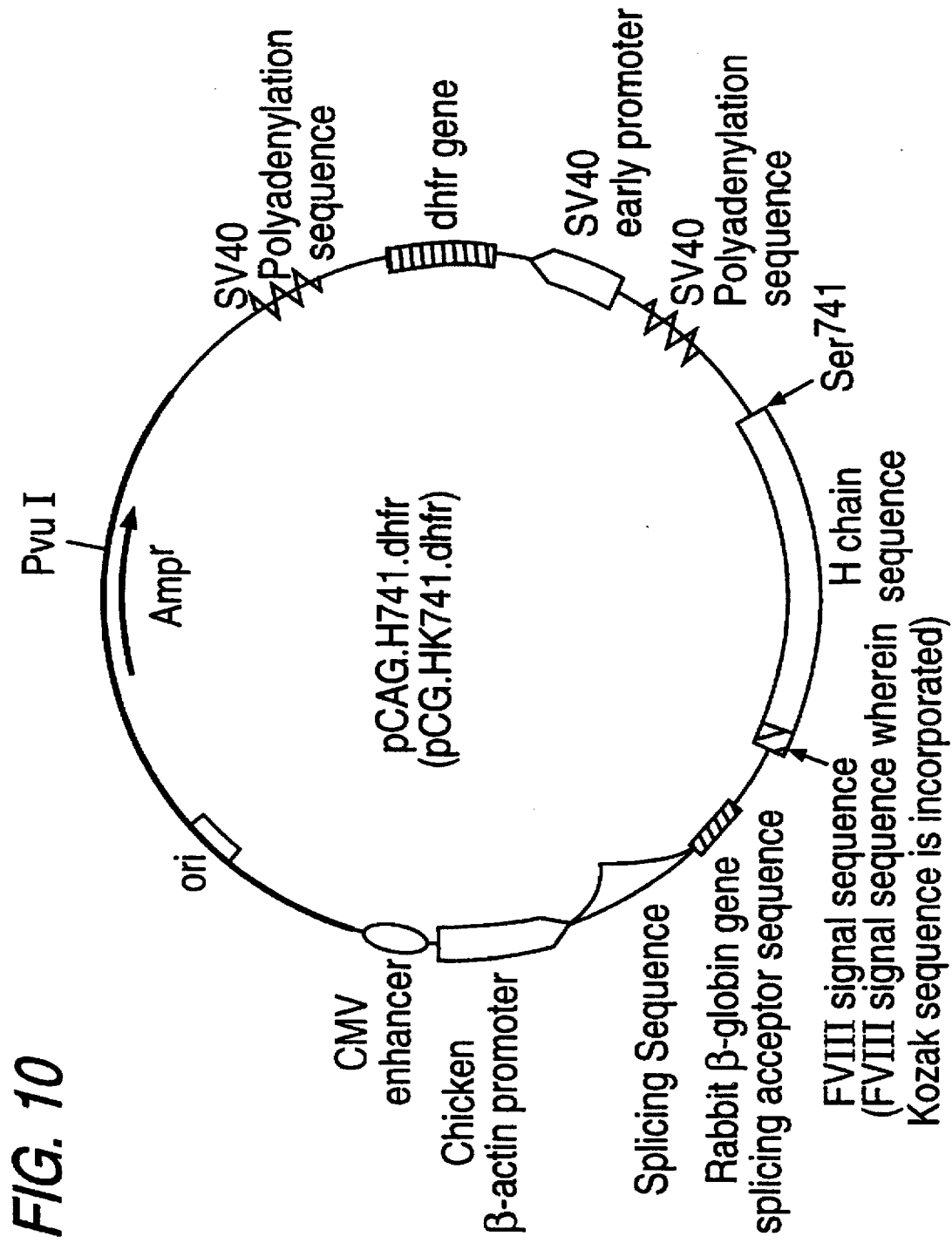
FIG. 10 illustrates the structure of the plasmids pCAG.H741.dhfr and pCAG.HK741.dhfr constructed in Example 12 and Example 13, respectively.

The H-chain 741 type fragment was introduced into the expression plasmid pCAG.dhfr constructed in Example 11. The plasmid pCAG.dhfr was digested with restriction enzyme SalI and the ends were dephosphorylated with an alkaline phosphatase derived from calf small intestine. This fragment was ligated with T4-DNA ligase to the XhoI-SalI DNA fragment coding for the FVIII H-chain obtained in Example 3 to cyclize to construct pCAG.H741.dhfr (FIG. 10).

EXAMPLE 13

Introduction of Kozak's consensus sequence into FVIII signal initiation codon region, and construction of expression plasmids pAG.HK741.dhfr and pCAG.HK741.dhfr for expression of H-chain 741 type wherein said signal is added In order to increase the expression level of H-chain, the Kozak's consensus sequence was introduced into the signal initiation codon region so that the translation efficiency from messenger RNA to protein is increased. The expression plasmid was constructed for the expression of 741 type which showed a high expression level in Example 5. The introduction of the Kozak sequence was carried out by the PCR method. The following two primers were employed.

Primer 1(SEQ ID NO:9):
5'-CCCTCGAGCCACCATGGAAATAGAGCTCTCC
Primer 2(SEQ ID NO:10):
5'-CCGGTCGACCCTCATCTTGGTTCAATGGCA The primer 1 coding for the N-terminus of the FVIII signal was modified at the 5'-end for inducing a mutation to introduce the NcoI site at the initiation codon. The primer 2 was the same as the primer 2 used in Example 2 for constructing the H-chain 740 type plasmid. A template for PCR was the plasmid 8.1 (FIG. 4). The PCR reaction was conducted under the same conditions as in Example 2. After completion of the reaction, the phenol extraction, the ether treatment and the ethanol precipitation were done. Then, the obtained PCR product was digested with restriction enzymes NcoI and SalI, the fragments were subjected to an agarose gel electrophoresis and a DNA fragment of about 2.3 kbp coding for the H-chain was extracted from the gel.

For subcloning, pUC18 was modified. pUC18 was digested with restriction enzyme EcoRI, blunt-ended with mung bean nuclease and ligated to cyclize with T4-DNA ligase in the presence of phosphorylated XhoI linker to construct pUCEnXh. By this treatment, the EcoRI recognition sites in the polylinker region of pUC18 were deleted and thereto were added XhoI recognition sites. The plasmid pUCEnXh was digested with restriction enzyme SmaI and ligated to cyclize with T4-DNA ligase under the presence of a synthetic NcoI linker having Kozak sequence (CCACCATGG) to construct a plasmid pUCEnXhSmnNck. The linker, after synthesis, was previously phosphorylated with T4 polynucleotide kinase.

Synthetic NcoI linker (SEQ ID NO:11);
5'-CCACCATGGTGG

The plasmid pUCEnXhSmnNck was digested with restriction enzymes NcoI and SalI and ligated to cyclize with the above PCR fragment with T4-DNA ligase to construct pUC.HK740. In order to remove a misreading and convert the expression to 741 type, a most DNA fragment except for the region where the Kozak's sequence is introduced was replaced with that of unamplified 741 type.

The plasmid pUC.HK740 was digested with restriction enzymes AflII and SalI and the ends were dephosphorylated with an alkaline phosphatase derived from bovine small intestine. The fragments were subjected to an agarose gel electrophoresis and a DNA fragment of about 3 kbp containing the H-chain signal region and the sequence derived from E. coli was extracted from the gel. The plasmid p11.H741 described in Example 3 was digested with restriction enzymes AflII and SalI, the fragments were subjected to an agarose gel electrophoresis and a DNA fragment of about 2 kbp coding for the C-terminal portion of the H-chain was extracted from the gel. This fragment was ligated to cyclize with the above fragment containing the Kozak's sequence with T4-DNA ligase to construct pUC.HK741. The DNA fragment of about 0.6 kbp between the NcoI and AflII sites coding for the signal and the N-terminal portion of the H-chain was subjected to DNA-sequencing by the dideoxy sequencing method and confirmed to be the correct sequence. The plasmid pUC.HK741 was digested with restriction enzymes XhoI and SalI, the fragments were subjected to an agarose gel electrophoresis and a fragment of about 2.3 kbp coding for the H-chain was extracted from the gel.

Figure 11:
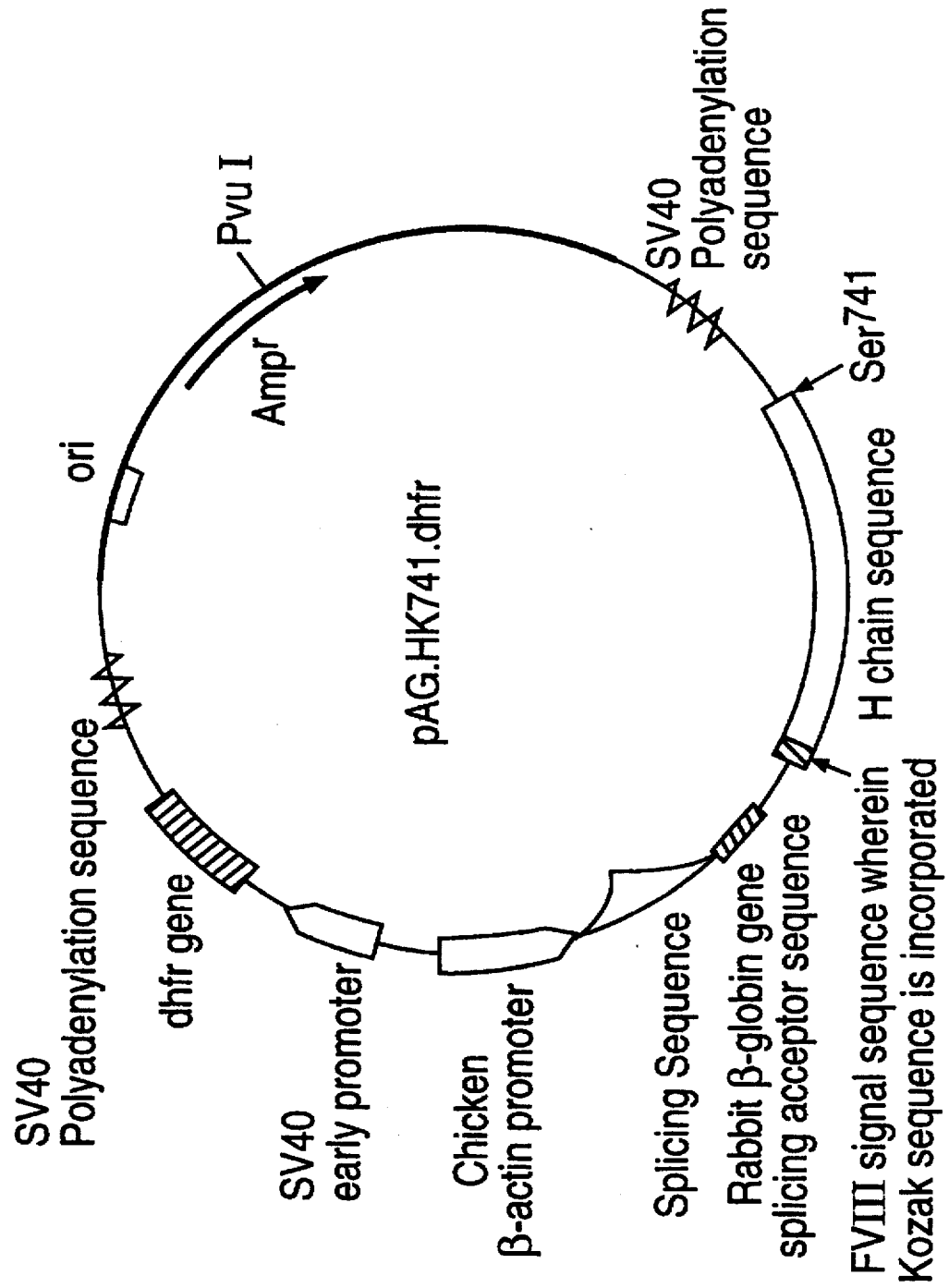
FIG. 11 illustrates the structure of the plasmid pAG.HK741.dhfr constructed in Example 13.

The expression plasmids pAG.dhfr and pCAG.dhfr were digested with restriction enzyme SalI and the ends were dephosphorylated with an alkaline phosphatase derived from calf small intestine. This was ligated to cyclize with the above fragment coding for the H-chain with T4-DNA ligase to construct H-chain expression plasmids pAG.HK741.dhfr and pCAG.HK741.dhfr wherein the Kozak sequence was introduced (FIG. 10 and FIG. 11).

EXAMPLE 14

Transfection of CHO cell with H-chain expression plasmid wherein Kozak's sequence was introduced and CAG expression plasmid wherein cytomegalovirus enhancer sequence was introduced CHO cells were transfected with the expression plasmids constructed in Examples 12 and 13. The H-chain expression plasmids pCAG.H741.dhfr, pCAG.HK741.dhfr and pAG.HK741.dhfr were previously digested with restriction enzyme PvuI to cyclize. The expression plasmid pAG.H741.dhfr constructed in Example 3 was also used as a control.

In order to determine the FVIII activity by the cotransfection with the H-chain expression plasmid and the L-chain expression plasmid, the L-chain 1563 type expression plasmid pAG.LD.dhfr was also digested with restriction enzyme PvuI. The transfection of the cells was conducted by using the Lipofectin reagent as in Example 5. CHO cells were transfected with the H-chain expression plasmid alone (4 expressions; Table 4) and cotransfected with the H-chain expression plasmid and the L-chain expression plasmid (4 expressions; Table 5). There were used 10 μg of the H-chain expression plasmid for the transformation of the H-chain alone and each 7 μg of the H-chain and L-chain expression plasmids for the cotransfection per 6-well multiplate for cell culture.

The cells were prepared and transfected in accordance with the procedure in Example 5. The culture was continued in a DHFR selection culture medium. For DHFR(+) cells, the expression level of the H-chain antigen was measured by the sandwich ELISA using a monoclonal antibodies specific for the H-chain and the FVIII activity was measured by Coatest kit. The results of the expression of the H-chain alone and of the coexpression of the H-chain and the L-chain are shown in Table 4 and Table 5, respectively.

TABLE 4

| Plasmid | Expression level of H-chain |
|---|---|
| pAG.H741.dhfr | 23 |
| pCAG.H741.dhfr | 100 |
| pAG.HK741.dhfr | 110 |
| pCAG.HK741.dhfr | 378 |

Unit; mU/day/$10^6$ cells

TABLE 5

| H-chain expression plasmid + L-chain expression plasmid | Factor VIII activity |
|---|---|
| pAG.H741.dhfr + pAG.LD.dhfr | 30 |
| pCAG.H741.dhfr + pAG.LD.dhfr | 104 |
| pAG.HK741.dhfr + pAG.LD.dhfr | 200 |
| pCAG.HK741.dhfr + pAG.LD.dhfr | 400 |

Unit; mU/day/$10^6$ cells

EXAMPLE 15

Cloning of CHO cell cotransfected with 741 type H-chain expression plasmid pAG.HK741.dhfr wherein Kozak's sequence is introduced and L-chain expression plasmid pAG. LD. dhfr and gene amplification thereof CHO cells were cotransfected with the H-chain 741 type expression plasmid pAG.HK741.dhfr wherein the Kozak sequence was introduced and the L-chain 1563 type expression plasmid pAG.LD.dhfr and cloned by the stainless steel cylinder method. CHO cells DG44 were inoculated onto a 6-well plate (Falcon) at $3 \times 10^5$ cells using MEM alpha culture medium containing 10% heat-inactivated fetal calf serum and cultured overnight. Using each 7 μg of the above expression plasmids pAG.HK741.dhfr and pAG.LD.dhfr previously digested with restriction enzyme PvuI to linearize, the cells were cotransfected by the Lipofectin method as in Example 10.

The culture was continued for two days after the transfection and then the cells were inoculated onto cell culture dishes of 15 cm diameter (Falcon) at $10^3$ cells/dish. The next day, the culture medium was replaced with the selection culture medium as mentioned above and the culture was continued while the culture medium was replaced with a fresh medium every 3 to 4 days. After about 7 to 10 days, cells transformed to DHFR(+) began to grow and formed colonies. These colonies (hereinafter referred to "clone") were separately peeled off using a stainless steel cylinder into a trypsin—EDTA solution, transferred to a 24-well plate (Nunc) for every clone and cultured in the selection culture medium. The next day, the culture medium was replaced with a fresh medium and the culture was continued. When the cells became confluent, the culture medium was replaced with a fresh medium and the FVIII activity in the culture supernatant after 24 hours was measured by Coatest kit. Among 244 clones obtained by the screening, 60 clones did not show the FVIII activity. These clones were supposed to be transformed with only either of the H-chain or L-chain expression plasmid and not to express both of the H-chain and the L-chain so that the activity could be detected.

In 149 clones among the above clones showing the FVIII activity in the above screening, the culture medium was replaced with the selection culture medium and the gene amplification was conducted using MTX in the same manner as in Example 5. The culture was continued for about 1 month while replacing the culture medium and thereby those MTX resistant cells gradually began to amplify. These cells were subcultured, and when almost became confluent, the culture medium was replaced with a fresh medium and the culture supernatant after 24 hours was screened by Coatest kit. Those clones showing a high FVIII expression activity in the screening was selected and further subjected to gene amplification with replacement of the culture medium with a selection medium containing a higher concentration of MTX. The gene amplification was carried out in the same schedule using MTX concentrations of 20 nM, 50 nM, 100 nM, 500 nM and 1 μM. The results of the screening by Coatest kit are shown in Table 6 for five clones which showed an especially high expression level.

TABLE 6

| | FVIII activity MTX concentration | | | | |
|---|---|---|---|---|---|
| Clone | 20 nM | 50 nM | 100 nM | 500 nM | 1 μM |
| No. 182 | 1690 | 1210 | 1980 | 5000 | 6340 |
| No. 389 | 1700 | 2270 | 3410 | 3300 | 5990 |
| No. 410 | 1780 | 2700 | 2500 | 4590 | 7020 |
| No. 455 | 1513 | 1750 | 2330 | 3490 | 10550 |

TABLE 6-continued

| | FVIII activity MTX concentration | | | | |
|---|---|---|---|---|---|
| Clone | 20 nM | 50 nM | 100 nM | 500 nM | 1 μM |
| No. 461 | 2247 | 2590 | 3810 | 3620 | 5050 |

Unit; mU/day/10⁶ cells

EXAMPLE 16

Gene amplification in CHO cells capable of producing 741 type H-chain wherein Kozak sequence is introduced which are transformed with CAG system expression plasmid (pCAG.HK741.dhfr) wherein cytomegalovirus enhancer is introduced CHO cells were transfected with the H-chain 741 type expression plasmid pCAG.HK741.dhfr wherein the Kozak's sequence was introduced (Example 13) and were subjected to the gene amplification using MTX. The MTX concentration was increased stepwise from 20 nM and the expression levels at each concentration were screened by ELISA using an antibodies specific for the H-chain. The results are shown in Table 7. As is clear from the results shown in Table 7, the expression level hardly increased at the lower concentrations of MTX (20 nM, 50 nM) and the increase of the expression level due to the gene amplification was firstly confirmed at the concentration 200 nM although the gene amplification was carried out starting from the same MTX concentration as that of Example 8.

TABLE 7

| | Before addition of MTX | MTX concentration | | |
|---|---|---|---|---|
| | | 20 nM MTX | 50 nM MTX | 200 nM MTX |
| Expression level of H-chain | 378 | 305 | 396 | 1080 |

Unit; mU/day/10⁶ cells

EXAMPLE 17

Construction of pCAG.tkdhfr wherein DHFR promoter of pCAG.dhfr is replaced with TK promoter As shown in Example 16, it was found that the gene amplification does not occur in the expression using the plasmid pCAG.dhfr unless a rather higher concentration of MTX is employed than that of the expression using the plasmid pAG.dhfr. This is probably because the CMV enhancer sequence contained in the expression plasmid pCAG.dhfr acts on the promoter for DHFR expression to enhance the promoter activity, resulting in the increase of the expression level of DHFR. In this respect, the promoter for DHFR expression was changed from the now used SV40 early promoter to a promoter of thymidine kinase (hereinafter referred to "TK") of herpes simplex virus which has a weaker promoter activity.

The TK promoter was obtained from the neomycin resistant gene expression plasmid pMC1neo-polyA (Stratagene). This plasmid was digested with restriction enzyme EcoRI and blunt-ended with T4-DNA polymerase and ligated to cyclize with T4-DNA ligase in the presence of phosphorylated BamHI linker to construct pMC1neo-E wherein the enhancer sequence of polyoma stem cell introduced into the TK promoter region of pMC1neo-polyA was removed. The plasmid pMC1neo-E was digested with restriction enzymes BamHI-PstI, the fragments were subjected to an agarose gel electrophoresis and a DNA fragment of about 200 bp coding for the TK promoter region was extracted from the gel. The DHFR expression plasmid pSV2-dhfr containing SV40 early promoter was digested with restriction enzyme HindIII and blunt-ended with T4-DNA polymerase and ligated to cyclize with T4-DNA ligase under the presence of phosphorylated PstI linker to construct pSV2-dhfr-P.

Figure 13:
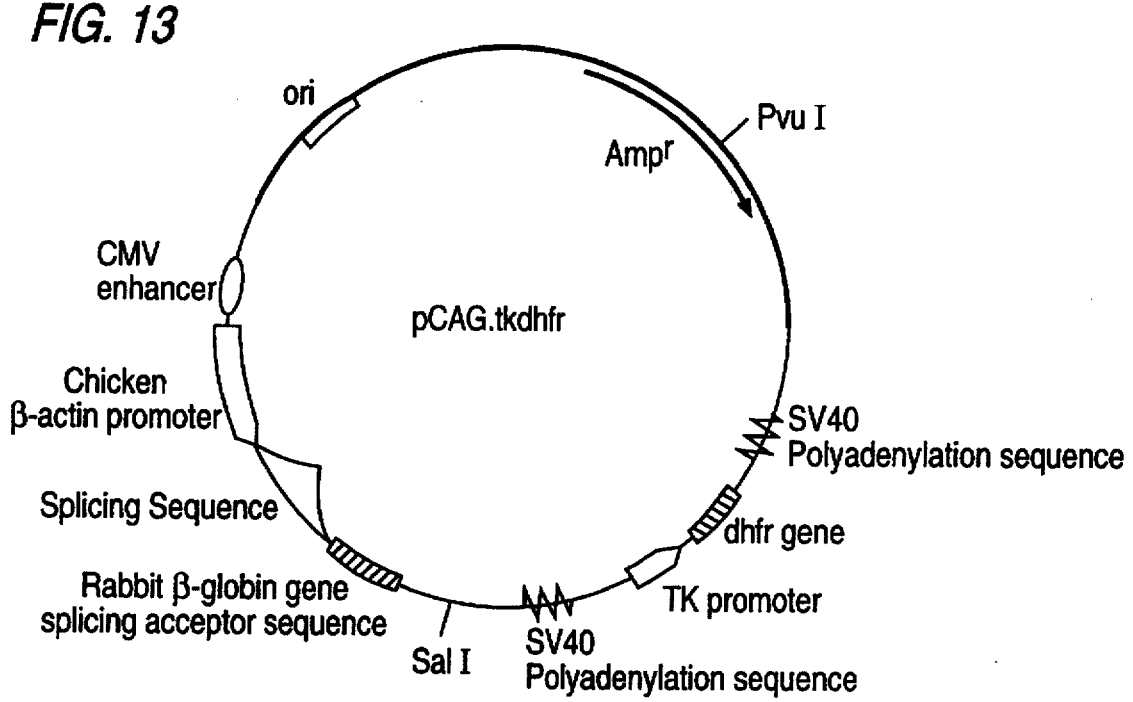
FIG. 13 shows the expression plasmid pCAG.tkdhfr which is constructed by replacing the DHFR promoter of the expression plasmid pCAG.dhfr with the TK promoter.

This plasmid was digested with restriction enzymes PstI-EcoRI, the fragments were subjected to an agarose gel electrophoresis and a DNA fragment of 1.3 kbp containing the DHFR structural gene and the SV40 polyadenylation signal was extracted from the gel. pUC18 was digested with restriction enzymes EcoRI-BamHI and the obtained fragment was ligated to cyclize with the above two DNA fragments with T4-DNA ligase to construct pUC.tkdhfr. The plasmid pUC.tkdhfr was digested with restriction enzyme BamHI, the fragments were subjected to an agarose gel electrophoresis and a DNA fragment of 1.1 kbp was extracted from the gel. The plasmid pCAGS-2 (FIG. 8) described in Example 11 was digested with restriction enzyme BamHI and the ends were dephosphorylated with an alkaline phosphatase derived from calf small intestine and then thereto was introduced the 1.1 kbp DNA fragment containing the TK promoter and the DHFR gene to construct an expression plasmid pCAG.tkdhfr (FIG. 13).

EXAMPLE 18

Introduction of H-chain 741 type gene with Kozak sequence and of L-chain 1563 type gene into pCAG.tkdhfr The FVIII H-chain and L-chain structural genes were introduced into pCAG.tkdhfr as described in Example 17.

Figure 14:
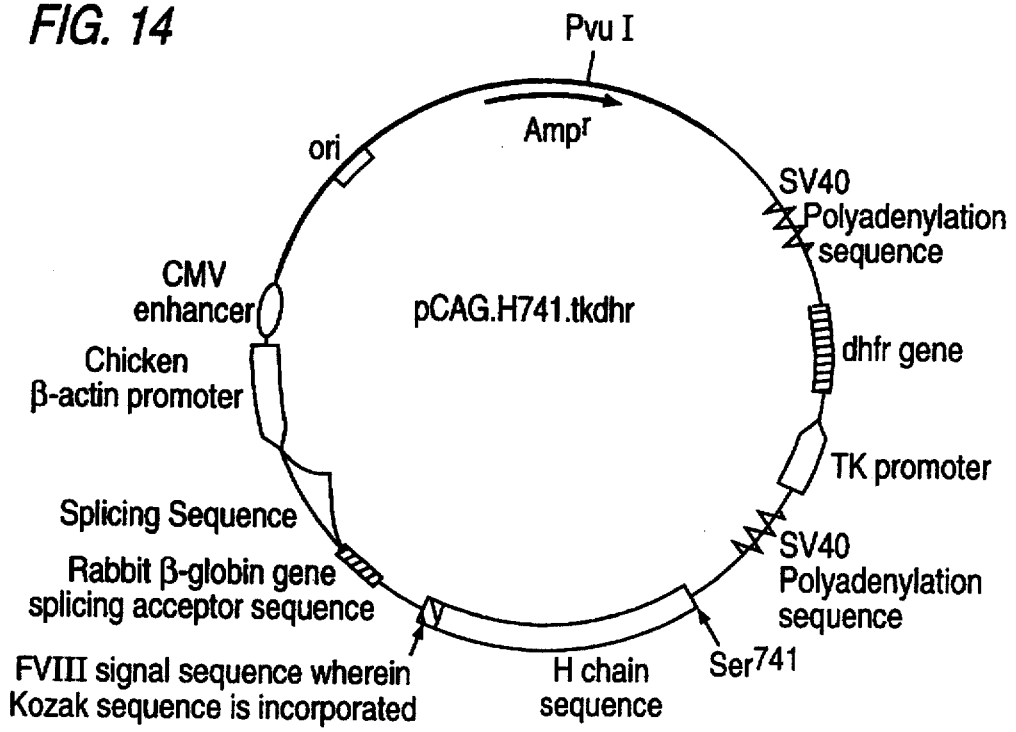
FIG. 14 shows the H-chain 741-type gene expression plasmid pCAG.HK741.dhfr with Kozak's sequence which is constructed by introducing the structural gene of the Factor VIII H-chain into the expression plasmid pCAG.tkdhfr.
Figure 15:
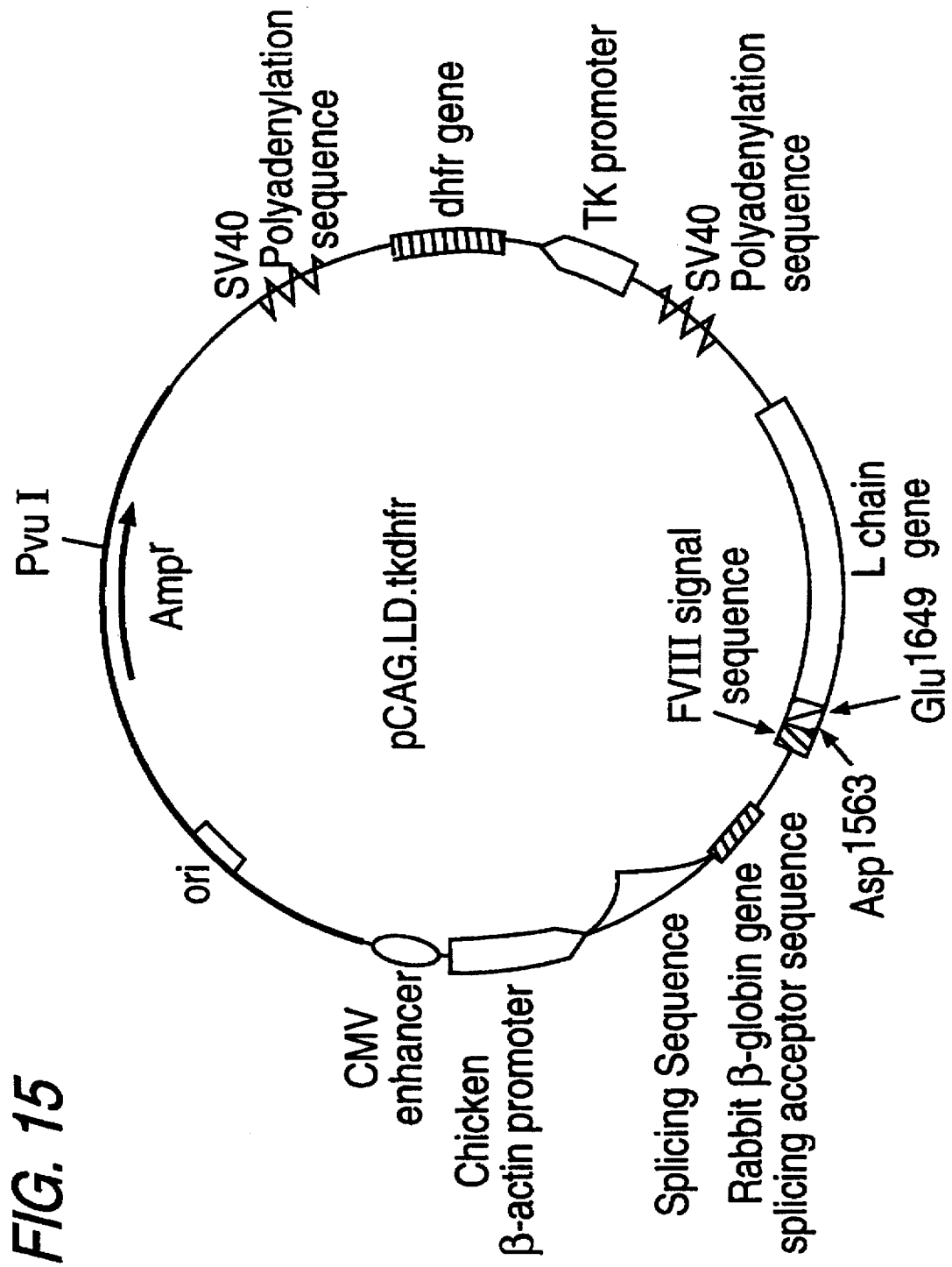
FIG. 15 shows the L-chain 1563-type gene expression plasmid pCAG.LD.dhfr which is constructed by introducing the structural gene of the Factor VIII L-chain into the expression plasmid pCAG.tkdhfr.

There were employed the expression of 741 type with Kozak's sequence as shown in Example 13 for the expression of H-chain and the expression of 1563 type as shown in Example 7 for the expression of L-chain. Each of the DNA fragments were obtained by the same procedures as in Example 13 and Example 7. The plasmid pCAG.tkdhfr was digested with restriction enzyme SalI and the ends were phosphorylated with an alkaline phosphatase derived from calf small intestine and thereto were ligated to cyclize the above DNA fragments with T4-DNA ligase to construct expression plasmids pCAG.HK741.tkdhfr and pCAG.LD.tkdhfr (FIG. 14 and FIG. 15), respectively.

EXAMPLE 19

Transfection of CHO cell with H-chain expression plasmid pCAG.HK741.tkdhfr and gene amplification thereof CHO cells were transfected with the expression plasmid pCAG.HK741.tkdhfr constructed in Example 18. The transfection was conducted by using the Lipofectin reagent as in Example 5. After transfection, the culture was continued in the DHFR selection medium and DHFR(+) cells were screened for the expression level by ELISA using a monoclonal antibodies specific for H-chain. Thereafter, the gene amplification by MTX was conducted wherein a lower MTX concentration than that of the conventional amplification was employed since, in the instant Example, the promoter for expression of DHFR was changed to the TK promoter. The cells were cultured at two MTX concentrations, 0.5 nM and 2 nM, and the culture was continued while the culture medium was replaced with a fresh medium until MTX-resistant cells began to grow. The MTX-resistant cells were reinoculated and then the expression level was screened by ELISA using a monoclonal antibodies specific for H-chain. The gene amplification was further conducted at the MTX concentrations of 5 nM and 20 nM for those cells resistant to 2 nM MTX. The results are shown in Table 8.

TABLE 8

|  | MTX concentration | | | | |
| --- | --- | --- | --- | --- | --- |
|  | 0 nM | 0.5 nM | 2 nM | 5 nM | 20 nM |
| Expression level of H-chain | 76 | 860 | 3440 | 6720 | 8430 |

Unit; mU/day/$10^6$ cells

EXAMPLE 20

Cotransfection of CHO cell with pCAG.HK741.tkdhfr and pCAG.LD.tkdhfr, cloning and gene amplification thereof CHO cells were cotransfected with the H-chain 741 type expression plasmid pCAG.HK741.tkdhfr and the L-chain 1563 type expression plasmid pCAG.LD.tkdhfr. The transfection was carried out by using the Lipofectin reagents as in Example 10. After transfection, for cloning by the stainless steel cylinder method, the cells were inoculated onto cell culture dishes of 15 cm diameter at $10^4$ cells/dish, and the next day, the culture medium was replaced with the DHFR selection medium. The culture was continued while the culture medium was replaced with a fresh medium until DHFR(+) cells formed a colony. The formed colonies were separately transferred to a 24-well plate using the stainless steel cylinder as in Example 15. These colonies (220 clones) were separately screened by Coatest kit and 167 clones having the FVIII activity were chosen and the gene amplification by MTX was conducted. With the MTX concentration increased stepwise by 5 nM, 10 nM and 20 nM, the cells were cultured while the clones showing higher increase of the expression level by the gene amplification were selected. The results of the screening of the FVIII activity are shown in Table 9.

TABLE 9

|  | FVIII activity MTX concentration | | |
| --- | --- | --- | --- |
| Clone | 5 nM | 10 nM | 20 nM |
| No. 378 | 1080 | 900 | 9000 |
| No. 501 | 1350 | 990 | 17540 |
| No. 502 | 2110 | 1010 | 6470 |
| No. 504 | 1670 | 790 | 7770 |
| No. 505 | 1820 | 960 | 20170 |

Unit; mU/day/$10^6$ cells

---

What we claim is:

1. A plasmid for expression of a human coagulation factor VIII heavy-chain, which comprises the following DNAs (a) to (d) in sequential order within the same cistron in a transcriptional direction:
   (a) a promoter capable of acting in an animal cell,
   (b) a DNA coding for a signal peptide including an initiation codon,
   (c) a DNA coding for an amino acid sequence selected from the group consisting of amino acid residues 1–741 or 1–745 of human coagulation factor VIII, and
   (d) a termination codon.

2. The plasmid of claim 1 wherein said DNA (b) coding for the signal peptide is derived from the human coagulation factor VIII gene.

3. The plasmid of claim 1 which further comprises an enhancer sequence at the upstream of said promoter.

4. The plasmid of claim 1 which further comprises an amplifiable gene.

5. The plasmid of claim 4 wherein said amplifiable gene is dihydrofolate reductase gene.

6. A transformed animal cell which is transformed with the plasmid as set forth in claim 1.

7. The transformed cell of claim 6 wherein the transformed animal cell is a Chinese hamster ovary cell.

8. A process for preparing a human coagulation factor VIII heavy-chain, which comprises forming a transformed animal cell by introducing the plasmid as set forth in claim 1 into an animal cell, culturing said cell to produce the human coagulation factor VIII heavy-chain in the culture medium, and collecting the thus produced human coagulation factor VIII heavy-chain.

9. A transformed animal cell which is cotransformed with both a plasmid for expression of a human coagulation factor VIII heavy-chain which comprises the following DNAs (a) to (d) in sequential order within the same cistron in a transcriptional direction:
   (a) a promoter capable of acting in an animal cell,
   (b) a DNA coding for a signal peptide including an initiation codon,
   (c) a DNA coding for an amino acid sequence selected from the group consisting of amino acid residues 1–741 or 1–745 of human coagulation factor VIII, and
   (d) a termination codon; and
   a plasmid for expression of a human coagulation factor VIII light-chain, which comprises the following DNAs (a') to (d') in sequential order within the same cistron in a transcriptional direction:
   (a') a promoter capable of acting in an animal cell,
   (b') a DNA coding for a signal peptide including an initiation codon,
   (c') a DNA coding for amino acid residues 1563–2332 of human coagulation factor VIII, and
   (d') a termination codon.

10. The transformed cell of claim 9 wherein the transformed animal cell is a Chinese hamster ovary cell.

11. A process for preparing a human coagulation factor VIII protein complex, which comprises forming a transformed animal cell by introducing both
   a plasmid for expression of a human coagulation factor VIII heavy-chain which comprises the following DNAs (a) to (d) in sequential order within the same cistron in a transcriptional direction:
   (a) a promoter capable of acting in an animal cell,
   (b) a DNA coding for a signal peptide including an initiation codon,
   (c) a DNA coding for an amino acid sequence selected from the group consisting of amino acid residues 1–741 or 1–745 of human coagulation factor VIII and
   (d) a termination codon; and
   a plasmid for expression of a human coagulation factor VIII light-chain, which comprises the following DNAs (a') to (d') in sequential order within the same cistron in a transcriptional direction:
   (a') a promoter capable of acting in an animal cell,
   (b') a DNA coding for a signal peptide including an initiation codon,
   (c') a DNA coding for amino acid residues 1563–2332 of human coagulation factor VIII, and
   (d') a termination codon into an animal cell, culturing said cell to produce the human coagulation factor VIII protein complex in the culture medium, and collecting the thus produced coagulation factor VIII protein complex.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 6999 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..6996

( x i ) SEQUENCE DESCRIPTION: SEQ ID NO:1:

```
GCC  ACC  AGA  AGA  TAC  TAC  CTG  GGT  GCA  GTG  GAA  CTG  TCA  TGG  GAC  TAT       48
Ala  Thr  Arg  Arg  Tyr  Tyr  Leu  Gly  Ala  Val  Glu  Leu  Ser  Trp  Asp  Tyr
 1              5                           10                          15

ATG  CAA  AGT  GAT  CTC  GGT  GAG  CTG  CCT  GTG  GAC  GCA  AGA  TTT  CCT  CCT       96
Met  Gln  Ser  Asp  Leu  Gly  Glu  Leu  Pro  Val  Asp  Ala  Arg  Phe  Pro  Pro
            20                          25                          30

AGA  GTG  CCA  AAA  TCT  TTT  CCA  TTC  AAC  ACC  TCA  GTC  GTG  TAC  AAA  AAG      144
Arg  Val  Pro  Lys  Ser  Phe  Pro  Phe  Asn  Thr  Ser  Val  Val  Tyr  Lys  Lys
        35                          40                          45

ACT  CTG  TTT  GTA  GAA  TTC  ACG  GAT  CAC  CTT  TTC  AAC  ATC  GCT  AAG  CCA      192
Thr  Leu  Phe  Val  Glu  Phe  Thr  Asp  His  Leu  Phe  Asn  Ile  Ala  Lys  Pro
    50                          55                          60

AGG  CCA  CCC  TGG  ATG  GGT  CTG  CTA  GGT  CCT  ACC  ATC  CAG  GCT  GAG  GTT      240
Arg  Pro  Pro  Trp  Met  Gly  Leu  Leu  Gly  Pro  Thr  Ile  Gln  Ala  Glu  Val
65                       70                          75                       80

TAT  GAT  ACA  GTG  GTC  ATT  ACA  CTT  AAG  AAC  ATG  GCT  TCC  CAT  CCT  GTC      288
Tyr  Asp  Thr  Val  Val  Ile  Thr  Leu  Lys  Asn  Met  Ala  Ser  His  Pro  Val
                85                          90                          95
```

-continued

| | | | | | | | | | | | | | | | | |
|---|---|---|---|---|---|---|---|---|---|---|---|---|---|---|---|---|
| AGT | CTT | CAT | GCT | GTT | GGT | GTA | TCC | TAC | TGG | AAA | GCT | TCT | GAG | GGA | GCT | 336 |
| Ser | Leu | His | Ala | Val | Gly | Val | Ser | Tyr | Trp | Lys | Ala | Ser | Glu | Gly | Ala | |
| | | 100 | | | | | 105 | | | | | 110 | | | | |
| GAA | TAT | GAT | GAT | CAG | ACC | AGT | CAA | AGG | GAG | AAA | GAA | GAT | GAT | AAA | GTC | 384 |
| Glu | Tyr | Asp | Asp | Gln | Thr | Ser | Gln | Arg | Glu | Lys | Glu | Asp | Asp | Lys | Val | |
| | | 115 | | | | | 120 | | | | | 125 | | | | |
| TTC | CCT | GGT | GGA | AGC | CAT | ACA | TAT | GTC | TGG | CAG | GTC | CTG | AAA | GAG | AAT | 432 |
| Phe | Pro | Gly | Gly | Ser | His | Thr | Tyr | Val | Trp | Gln | Val | Leu | Lys | Glu | Asn | |
| | | 130 | | | | | 135 | | | | | 140 | | | | |
| GGT | CCA | ATG | GCC | TCT | GAC | CCA | CTG | TGC | CTT | ACC | TAC | TCA | TAT | CTT | TCT | 480 |
| Gly | Pro | Met | Ala | Ser | Asp | Pro | Leu | Cys | Leu | Thr | Tyr | Ser | Tyr | Leu | Ser | |
| 145 | | | | | 150 | | | | | 155 | | | | | 160 | |
| CAT | GTG | GAC | CTG | GTA | AAA | GAC | TTG | AAT | TCA | GGC | CTC | ATT | GGA | GCC | CTA | 528 |
| His | Val | Asp | Leu | Val | Lys | Asp | Leu | Asn | Ser | Gly | Leu | Ile | Gly | Ala | Leu | |
| | | | | 165 | | | | | 170 | | | | | 175 | | |
| CTA | GTA | TGT | AGA | GAA | GGG | AGT | CTG | GCC | AAG | GAA | AAG | ACA | CAG | ACC | TTG | 576 |
| Leu | Val | Cys | Arg | Glu | Gly | Ser | Leu | Ala | Lys | Glu | Lys | Thr | Gln | Thr | Leu | |
| | | | 180 | | | | | 185 | | | | | 190 | | | |
| CAC | AAA | TTT | ATA | CTA | CTT | TTT | GCT | GTA | TTT | GAT | GAA | GGG | AAA | AGT | TGG | 624 |
| His | Lys | Phe | Ile | Leu | Leu | Phe | Ala | Val | Phe | Asp | Glu | Gly | Lys | Ser | Trp | |
| | | 195 | | | | | 200 | | | | | 205 | | | | |
| CAC | TCA | GAA | ACA | AAG | AAC | TCC | TTG | ATG | CAG | GAT | AGG | GAT | GCT | GCA | TCT | 672 |
| His | Ser | Glu | Thr | Lys | Asn | Ser | Leu | Met | Gln | Asp | Arg | Asp | Ala | Ala | Ser | |
| | 210 | | | | | 215 | | | | | 220 | | | | | |
| GCT | CGG | GCC | TGG | CCT | AAA | ATG | CAC | ACA | GTC | AAT | GGT | TAT | GTA | AAC | AGG | 720 |
| Ala | Arg | Ala | Trp | Pro | Lys | Met | His | Thr | Val | Asn | Gly | Tyr | Val | Asn | Arg | |
| 225 | | | | | 230 | | | | | 235 | | | | | 240 | |
| TCT | CTG | CCA | GGT | CTG | ATT | GGA | TGC | CAC | AGG | AAA | TCA | GTC | TAT | TGG | CAT | 768 |
| Ser | Leu | Pro | Gly | Leu | Ile | Gly | Cys | His | Arg | Lys | Ser | Val | Tyr | Trp | His | |
| | | | | 245 | | | | | 250 | | | | | 255 | | |
| GTG | ATT | GGA | ATG | GGC | ACC | ACT | CCT | GAA | GTG | CAC | TCA | ATA | TTC | CTC | GAA | 816 |
| Val | Ile | Gly | Met | Gly | Thr | Thr | Pro | Glu | Val | His | Ser | Ile | Phe | Leu | Glu | |
| | | | | 260 | | | | | 265 | | | | | 270 | | |
| GGT | CAC | ACA | TTT | CTT | GTG | AGG | AAC | CAT | CGC | CAG | GCG | TCC | TTG | GAA | ATC | 864 |
| Gly | His | Thr | Phe | Leu | Val | Arg | Asn | His | Arg | Gln | Ala | Ser | Leu | Glu | Ile | |
| | | 275 | | | | | 280 | | | | | 285 | | | | |
| TCG | CCA | ATA | ACT | TTC | CTT | ACT | GCT | CAA | ACA | CTC | TTG | ATG | GAC | CTT | GGA | 912 |
| Ser | Pro | Ile | Thr | Phe | Leu | Thr | Ala | Gln | Thr | Leu | Leu | Met | Asp | Leu | Gly | |
| | 290 | | | | | 295 | | | | | 300 | | | | | |
| CAG | TTT | CTA | CTG | TTT | TGT | CAT | ATC | TCT | TCC | CAC | CAA | CAT | GAT | GGC | ATG | 960 |
| Gln | Phe | Leu | Leu | Phe | Cys | His | Ile | Ser | Ser | His | Gln | His | Asp | Gly | Met | |
| 305 | | | | | 310 | | | | | 315 | | | | | 320 | |
| GAA | GCT | TAT | GTC | AAA | GTA | GAC | AGC | TGT | CCA | GAG | GAA | CCC | CAA | CTA | CGA | 1008 |
| Glu | Ala | Tyr | Val | Lys | Val | Asp | Ser | Cys | Pro | Glu | Glu | Pro | Gln | Leu | Arg | |
| | | | | 325 | | | | | 330 | | | | | 335 | | |
| ATG | AAA | AAT | AAT | GAA | GAA | GCG | GAA | GAC | TAT | GAT | GAT | GAT | CTT | ACT | GAT | 1056 |
| Met | Lys | Asn | Asn | Glu | Glu | Ala | Glu | Asp | Tyr | Asp | Asp | Asp | Leu | Thr | Asp | |
| | | | 340 | | | | | 345 | | | | | 350 | | | |
| TCT | GAA | ATG | GAT | GTG | GTC | AGG | TTT | GAT | GAT | GAC | AAC | TCT | CCT | TCC | TTT | 1104 |
| Ser | Glu | Met | Asp | Val | Val | Arg | Phe | Asp | Asp | Asp | Asn | Ser | Pro | Ser | Phe | |
| | | 355 | | | | | 360 | | | | | 365 | | | | |
| ATC | CAA | ATT | CGC | TCA | GTT | GCC | AAG | AAG | CAT | CCT | AAA | ACT | TGG | GTA | CAT | 1152 |
| Ile | Gln | Ile | Arg | Ser | Val | Ala | Lys | Lys | His | Pro | Lys | Thr | Trp | Val | His | |
| | 370 | | | | | 375 | | | | | 380 | | | | | |
| TAC | ATT | GCT | GCT | GAA | GAG | GAG | GAC | TGG | GAC | TAT | GCT | CCC | TTA | GTC | CTC | 1200 |
| Tyr | Ile | Ala | Ala | Glu | Glu | Glu | Asp | Trp | Asp | Tyr | Ala | Pro | Leu | Val | Leu | |
| 385 | | | | | 390 | | | | | 395 | | | | | 400 | |
| GCC | CCC | GAT | GAC | AGA | AGT | TAT | AAA | AGT | CAA | TAT | TTG | AAC | AAT | GGC | CCT | 1248 |
| Ala | Pro | Asp | Asp | Arg | Ser | Tyr | Lys | Ser | Gln | Tyr | Leu | Asn | Asn | Gly | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| CAG | CGG | ATT | GGT | AGG | AAG | TAC | AAA | AAA | GTC | CGA | TTT | ATG | GCA | TAC | ACA | 1296 |
| Gln | Arg | Ile | Gly 420 | Arg | Lys | Tyr | Lys | Lys 425 | Val | Arg | Phe | Met | Ala 430 | Tyr | Thr | |
| GAT | GAA | ACC | TTT | AAG | ACT | CGT | GAA | GCT | ATT | CAG | CAT | GAA | TCA | GGA | ATC | 1344 |
| Asp | Glu | Thr 435 | Phe | Lys | Thr | Arg | Glu | Ala 440 | Ile | Gln | His | Glu 445 | Ser | Gly | Ile | |
| TTG | GGA | CCT | TTA | CTT | TAT | GGG | GAA | GTT | GGA | GAC | ACA | CTG | TTG | ATT | ATA | 1392 |
| Leu | Gly 450 | Pro | Leu | Leu | Tyr | Gly 455 | Glu | Val | Gly | Asp | Thr 460 | Leu | Leu | Ile | Ile | |
| TTT | AAG | AAT | CAA | GCA | AGC | AGA | CCA | TAT | AAC | ATC | TAC | CCT | CAC | GGA | ATC | 1440 |
| Phe 465 | Lys | Asn | Gln | Ala | Ser 470 | Arg | Pro | Tyr | Asn | Ile 475 | Tyr | Pro | His | Gly | Ile 480 | |
| ACT | GAT | GTC | CGT | CCT | TTG | TAT | TCA | AGG | AGA | TTA | CCA | AAA | GGT | GTA | AAA | 1488 |
| Thr | Asp | Val | Arg | Pro 485 | Leu | Tyr | Ser | Arg | Arg 490 | Leu | Pro | Lys | Gly | Val 495 | Lys | |
| CAT | TTG | AAG | GAT | TTT | CCA | ATT | CTG | CCA | GGA | GAA | ATA | TTC | AAA | TAT | AAA | 1536 |
| His | Leu | Lys | Asp 500 | Phe | Pro | Ile | Leu | Pro 505 | Gly | Glu | Ile | Phe | Lys 510 | Tyr | Lys | |
| TGG | ACA | GTG | ACT | GTA | GAA | GAT | GGG | CCA | ACT | AAA | TCA | GAT | CCT | CGG | TGC | 1584 |
| Trp | Thr | Val 515 | Thr | Val | Glu | Asp | Gly 520 | Pro | Thr | Lys | Ser | Asp 525 | Pro | Arg | Cys | |
| CTG | ACC | CGC | TAT | TAC | TCT | AGT | TTC | GTT | AAT | ATG | GAG | AGA | GAT | CTA | GCT | 1632 |
| Leu | Thr 530 | Arg | Tyr | Tyr | Ser | Ser 535 | Phe | Val | Asn | Met | Glu 540 | Arg | Asp | Leu | Ala | |
| TCA | GGA | CTC | ATT | GGC | CCT | CTC | CTC | ATC | TGC | TAC | AAA | GAA | TCT | GTA | GAT | 1680 |
| Ser 545 | Gly | Leu | Ile | Gly | Pro 550 | Leu | Leu | Ile | Cys | Tyr 555 | Lys | Glu | Ser | Val | Asp 560 | |
| CAA | AGA | GGA | AAC | CAG | ATA | ATG | TCA | GAC | AAG | AGG | AAT | GTC | ATC | CTG | TTT | 1728 |
| Gln | Arg | Gly | Asn | Gln 565 | Ile | Met | Ser | Asp | Lys 570 | Arg | Asn | Val | Ile | Leu 575 | Phe | |
| TCT | GTA | TTT | GAT | GAG | AAC | CGA | AGC | TGG | TAC | CTC | ACA | GAG | AAT | ATA | CAA | 1776 |
| Ser | Val | Phe | Asp 580 | Glu | Asn | Arg | Ser | Trp 585 | Tyr | Leu | Thr | Glu | Asn 590 | Ile | Gln | |
| CGC | TTT | CTC | CCC | AAT | CCA | GCT | GGA | GTG | CAG | CTT | GAG | GAT | CCA | GAG | TTC | 1824 |
| Arg | Phe | Leu 595 | Pro | Asn | Pro | Ala | Gly 600 | Val | Gln | Leu | Glu | Asp 605 | Pro | Glu | Phe | |
| CAA | GCC | TCC | AAC | ATC | ATG | CAC | AGC | ATC | AAT | GGC | TAT | GTT | TTT | GAT | AGT | 1872 |
| Gln | Ala 610 | Ser | Asn | Ile | Met | His 615 | Ser | Ile | Asn | Gly | Tyr 620 | Val | Phe | Asp | Ser | |
| TTG | CAG | TTG | TCA | GTT | TGT | TTG | CAT | GAG | GTG | GCA | TAC | TGG | TAC | ATT | CTA | 1920 |
| Leu 625 | Gln | Leu | Ser | Val | Cys 630 | Leu | His | Glu | Val | Ala 635 | Tyr | Trp | Tyr | Ile | Leu 640 | |
| AGC | ATT | GGA | GCA | CAG | ACT | GAC | TTC | CTT | TCT | GTC | TTC | TTC | TCT | GGA | TAT | 1968 |
| Ser | Ile | Gly | Ala | Gln 645 | Thr | Asp | Phe | Leu | Ser 650 | Val | Phe | Phe | Ser | Gly 655 | Tyr | |
| ACC | TTC | AAA | CAC | AAA | ATG | GTC | TAT | GAA | GAC | ACA | CTC | ACC | CTA | TTC | CCA | 2016 |
| Thr | Phe | Lys | His 660 | Lys | Met | Val | Tyr | Glu 665 | Asp | Thr | Leu | Thr | Leu 670 | Phe | Pro | |
| TTC | TCA | GGA | GAA | ACT | GTC | TTC | ATG | TCG | ATG | GAA | AAC | CCA | GGT | CTA | TGG | 2064 |
| Phe | Ser | Gly 675 | Glu | Thr | Val | Phe | Met 680 | Ser | Met | Glu | Asn | Pro 685 | Gly | Leu | Trp | |
| ATT | CTG | GGG | TGC | CAC | AAC | TCA | GAC | TTT | CGG | AAC | AGA | GGC | ATG | ACC | GCC | 2112 |
| Ile | Leu | Gly 690 | Cys | His | Asn | Ser | Asp 695 | Phe | Arg | Asn | Arg | Gly 700 | Met | Thr | Ala | |
| TTA | CTG | AAG | GTT | TCT | AGT | TGT | GAC | AAG | AAC | ACT | GGT | GAT | TAT | TAC | GAG | 2160 |
| Leu 705 | Leu | Lys | Val | Ser | Ser 710 | Cys | Asp | Lys | Asn | Thr 715 | Gly | Asp | Tyr | Tyr | Glu 720 | |
| GAC | AGT | TAT | GAA | GAT | ATT | TCA | GCA | TAC | TTG | CTG | AGT | AAA | AAC | AAT | GCC | 2208 |
| Asp | Ser | Tyr | Glu | Asp 725 | Ile | Ser | Ala | Tyr | Leu 730 | Leu | Ser | Lys | Asn | Asn 735 | Ala | |

```
ATT GAA CCA AGA AGC TTC TCC CAG AAT TCA AGA CAC CGT AGC ACT AGG       2256
Ile Glu Pro Arg Ser Phe Ser Gln Asn Ser Arg His Arg Ser Thr Arg
            740                 745                 750

CAA AAG CAA TTT AAT GCC ACC ACA ATT CCA GAA AAT GAC ATA GAG AAG       2304
Gln Lys Gln Phe Asn Ala Thr Thr Ile Pro Glu Asn Asp Ile Glu Lys
        755                 760                 765

ACT GAC CCT TGG TTT GCA CAC AGA ACA CCT ATG CCT AAA ATA CAA AAT       2352
Thr Asp Pro Trp Phe Ala His Arg Thr Pro Met Pro Lys Ile Gln Asn
    770                 775                 780

GTC TCC TCT AGT GAT TTG TTG ATG CTC TTG CGA CAG AGT CCT ACT CCA       2400
Val Ser Ser Ser Asp Leu Leu Met Leu Leu Arg Gln Ser Pro Thr Pro
785                 790                 795                 800

CAT GGG CTA TCC TTA TCT GAT CTC CAA GAA GCC AAA TAT GAG ACT TTT       2448
His Gly Leu Ser Leu Ser Asp Leu Gln Glu Ala Lys Tyr Glu Thr Phe
                805                 810                 815

TCT GAT GAT CCA TCA CCT GGA GCA ATA GAC AGT AAT AAC AGC CTG TCT       2496
Ser Asp Asp Pro Ser Pro Gly Ala Ile Asp Ser Asn Asn Ser Leu Ser
            820                 825                 830

GAA ATG ACA CAC TTC AGG CCA CAG CTC CAT CAC AGT GGG GAC ATG GTA       2544
Glu Met Thr His Phe Arg Pro Gln Leu His His Ser Gly Asp Met Val
        835                 840                 845

TTT ACC CCT GAG TCA GGC CTC CAA TTA AGA TTA AAT GAG AAA CTG GGG       2592
Phe Thr Pro Glu Ser Gly Leu Gln Leu Arg Leu Asn Glu Lys Leu Gly
    850                 855                 860

ACA ACT GCA GCA ACA GAG TTG AAG AAA CTT GAT TTC AAA GTT TCT AGT       2640
Thr Thr Ala Ala Thr Glu Leu Lys Lys Leu Asp Phe Lys Val Ser Ser
865                 870                 875                 880

ACA TCA AAT AAT CTG ATT TCA ACA ATT CCA TCA GAC AAT TTG GCA GCA       2688
Thr Ser Asn Asn Leu Ile Ser Thr Ile Pro Ser Asp Asn Leu Ala Ala
                885                 890                 895

GGT ACT GAT AAT ACA AGT TCC TTA GGA CCC CCA AGT ATG CCA GTT CAT       2736
Gly Thr Asp Asn Thr Ser Ser Leu Gly Pro Pro Ser Met Pro Val His
            900                 905                 910

TAT GAT AGT CAA TTA GAT ACC ACT CTA TTT GGC AAA AAG TCA TCT CCC       2784
Tyr Asp Ser Gln Leu Asp Thr Thr Leu Phe Gly Lys Lys Ser Ser Pro
        915                 920                 925

CTT ACT GAG TCT GGT GGA CCT CTG AGC TTG AGT GAA GAA AAT AAT GAT       2832
Leu Thr Glu Ser Gly Gly Pro Leu Ser Leu Ser Glu Glu Asn Asn Asp
    930                 935                 940

TCA AAG TTG TTA GAA TCA GGT TTA ATG AAT AGC CAA GAA AGT TCA TGG       2880
Ser Lys Leu Leu Glu Ser Gly Leu Met Asn Ser Gln Glu Ser Ser Trp
945                 950                 955                 960

GGA AAA AAT GTA TCG TCA ACA GAG AGT GGT AGG TTA TTT AAA GGG AAA       2928
Gly Lys Asn Val Ser Ser Thr Glu Ser Gly Arg Leu Phe Lys Gly Lys
                965                 970                 975

AGA GCT CAT GGA CCT GCT TTG TTG ACT AAA GAT AAT GCC TTA TTC AAA       2976
Arg Ala His Gly Pro Ala Leu Leu Thr Lys Asp Asn Ala Leu Phe Lys
            980                 985                 990

GTT AGC ATC TCT TTG TTA AAG ACA AAC AAA ACT TCC AAT AAT TCA GCA       3024
Val Ser Ile Ser Leu Leu Lys Thr Asn Lys Thr Ser Asn Asn Ser Ala
        995                 1000                1005

ACT AAT AGA AAG ACT CAC ATT GAT GGC CCA TCA TTA TTA ATT GAG AAT       3072
Thr Asn Arg Lys Thr His Ile Asp Gly Pro Ser Leu Leu Ile Glu Asn
    1010                1015                1020

AGT CCA TCA GTC TGG CAA AAT ATA TTA GAA AGT GAC ACT GAG TTT AAA       3120
Ser Pro Ser Val Trp Gln Asn Ile Leu Glu Ser Asp Thr Glu Phe Lys
1025                1030                1035                1040

AAA GTG ACA CCT TTG ATT CAT GAC AGA ATG CTT ATG GAC AAA AAT GCT       3168
Lys Val Thr Pro Leu Ile His Asp Arg Met Leu Met Asp Lys Asn Ala
                1045                1050                1055
```

| | | | | | | | | | | | | | | | | |
|---|---|---|---|---|---|---|---|---|---|---|---|---|---|---|---|---|
| ACA | GCT | TTG | AGG | CTA | AAT | CAT | ATG | TCA | AAT | AAA | ACT | ACT | TCA | TCA | AAA | 3216 |
| Thr | Ala | Leu | Arg 1060 | Leu | Asn | His | Met | Ser 1065 | Asn | Lys | Thr | Thr | Ser 1070 | Ser | Lys | |
| AAC | ATG | GAA | ATG | GTC | CAA | CAG | AAA | AAA | GAG | GGC | CCC | ATT | CCA | CCA | GAT | 3264 |
| Asn | Met | Glu 1075 | Met | Val | Gln | Gln | Lys 1080 | Lys | Glu | Gly | Pro | Ile 1085 | Pro | Pro | Asp | |
| GCA | CAA | AAT | CCA | GAT | ATG | TCG | TTC | TTT | AAG | ATG | CTA | TTC | TTG | CCA | GAA | 3312 |
| Ala | Gln | Asn 1090 | Pro | Asp | Met | Ser | Phe 1095 | Phe | Lys | Met | Leu | Phe 1100 | Leu | Pro | Glu | |
| TCA | GCA | AGG | TGG | ATA | CAA | AGG | ACT | CAT | GGA | AAG | AAC | TCT | CTG | AAC | TCT | 3360 |
| Ser | Ala | Arg 1105 | Trp | Ile | Gln 1110 | Arg | Thr | His | Gly | Lys 1115 | Asn | Ser | Leu | Asn 1120 | Ser | |
| GGG | CAA | GGC | CCC | AGT | CCA | AAG | CAA | TTA | GTA | TCC | TTA | GGA | CCA | GAA | AAA | 3408 |
| Gly | Gln | Gly | Pro | Ser 1125 | Pro | Lys | Gln | Leu | Val 1130 | Ser | Leu | Gly | Pro | Glu 1135 | Lys | |
| TCT | GTG | GAA | GGT | CAG | AAT | TTC | TTG | TCT | GAG | AAA | AAC | AAA | GTG | GTA | GTA | 3456 |
| Ser | Val | Glu | Gly 1140 | Gln | Asn | Phe | Leu | Ser 1145 | Glu | Lys | Asn | Lys | Val 1150 | Val | Val | |
| CGA | AAG | GGT | GAA | TTT | ACA | AAG | GAC | GTA | GGA | CTC | AAA | GAG | ATG | GTT | TTT | 3504 |
| Arg | Lys | Gly | Glu 1155 | Phe | Thr | Lys | Asp | Val 1160 | Gly | Leu | Lys | Glu | Met 1165 | Val | Phe | |
| CCA | AGC | AGC | AGA | AAC | CTA | TTT | CTT | ACT | AAC | TTG | GAT | AAT | TTA | CAT | GAA | 3552 |
| Pro | Ser | Ser 1170 | Arg | Asn | Leu | Phe | Leu 1175 | Thr | Asn | Leu | Asp | Asn 1180 | Leu | His | Glu | |
| AAT | AAT | ACA | CAC | AAT | CAA | GAA | AAA | AAA | ATT | CAG | GAA | GAA | ATA | GAA | AAG | 3600 |
| Asn 1185 | Asn | Thr | His | Asn | Gln 1190 | Glu | Lys | Lys | Ile | Gln 1195 | Glu | Glu | Ile | Glu | Lys 1200 | |
| AAG | GAA | ACA | TTA | ATC | CAA | GAG | AAT | GTA | GTT | TTG | CCT | CAG | ATA | CAT | ACA | 3648 |
| Lys | Glu | Thr | Leu | Ile 1205 | Gln | Glu | Asn | Val | Val 1210 | Leu | Pro | Gln | Ile | His 1215 | Thr | |
| GTG | ACT | GGC | ACT | AAG | AAT | TTC | ATG | AAG | AAC | CTT | TTC | TTA | CTG | AGC | ACT | 3696 |
| Val | Thr | Gly | Thr | Lys 1220 | Asn | Phe | Met | Lys | Asn 1225 | Leu | Phe | Leu | Leu | Ser 1230 | Thr | |
| AGG | CAA | AAT | GTA | GAA | GGT | TCA | TAT | GAC | GGG | GCA | TAT | GCT | CCA | GTA | CTT | 3744 |
| Arg | Gln | Asn | Val | Glu 1235 | Gly | Ser | Tyr | Asp | Gly 1240 | Ala | Tyr | Ala | Pro | Val 1245 | Leu | |
| CAA | GAT | TTT | AGG | TCA | TTA | AAT | GAT | TCA | ACA | AAT | AGA | ACA | AAG | AAA | CAC | 3792 |
| Gln | Asp | Phe | Arg 1250 | Ser | Leu | Asn | Asp | Ser 1255 | Thr | Asn | Arg | Thr | Lys 1260 | Lys | His | |
| ACA | GCT | CAT | TTC | TCA | AAA | AAA | GGG | GAG | GAA | GAA | AAC | TTG | GAA | GGC | TTG | 3840 |
| Thr | Ala | His | Phe | Ser 1265 | Lys | Lys | Gly | Glu | Glu 1270 | Glu | Asn | Leu | Glu | Gly 1275 | Leu 1280 | |
| GGA | AAT | CAA | ACC | AAG | CAA | ATT | GTA | GAG | AAA | TAT | GCA | TGC | ACC | ACA | AGG | 3888 |
| Gly | Asn | Gln | Thr | Lys 1285 | Gln | Ile | Val | Glu | Lys 1290 | Tyr | Ala | Cys | Thr | Thr 1295 | Arg | |
| ATA | TCT | CCT | AAT | ACA | AGC | CAG | CAG | AAT | TTT | GTC | ACG | CAA | CGT | AGT | AAG | 3936 |
| Ile | Ser | Pro | Asn | Thr 1300 | Ser | Gln | Gln | Asn | Phe 1305 | Val | Thr | Gln | Arg | Ser 1310 | Lys | |
| AGA | GCT | TTG | AAA | CAA | TTC | AGA | CTC | CCA | CTA | GAA | GAA | ACA | GAA | CTT | GAA | 3984 |
| Arg | Ala | Leu | Lys 1315 | Gln | Phe | Arg | Leu | Pro 1320 | Leu | Glu | Glu | Thr | Glu 1325 | Leu | Glu | |
| AAA | AGG | ATA | ATT | GTG | GAT | GAC | ACC | TCA | ACC | CAG | TGG | TCC | AAA | AAC | ATG | 4032 |
| Lys | Arg | Ile 1330 | Ile | Val | Asp | Asp 1335 | Thr | Ser | Thr | Gln | Trp 1340 | Ser | Lys | Asn | Met | |
| AAA | CAT | TTG | ACC | CCG | AGC | ACC | CTC | ACA | CAG | ATA | GAC | TAC | AAT | GAG | AAG | 4080 |
| Lys 1345 | His | Leu | Thr | Pro | Ser 1350 | Thr | Leu | Thr | Gln | Ile 1355 | Asp | Tyr | Asn | Glu | Lys 1360 | |
| GAG | AAA | GGG | GCC | ATT | ACT | CAG | TCT | CCC | TTA | TCA | GAT | TGC | CTT | ACG | AGG | 4128 |
| Glu | Lys | Gly | Ala | Ile 1365 | Thr | Gln | Ser | Pro | Leu 1370 | Ser | Asp | Cys | Leu | Thr 1375 | Arg | |

```
AGT CAT AGC ATC CCT CAA GCA AAT AGA TCT CCA TTA CCC ATT GCA AAG    4176
Ser His Ser Ile Pro Gln Ala Asn Arg Ser Pro Leu Pro Ile Ala Lys
        1380                    1385                    1390

GTA TCA TCA TTT CCA TCT ATT AGA CCT ATA TAT CTG ACC AGG GTC CTA    4224
Val Ser Ser Phe Pro Ser Ile Arg Pro Ile Tyr Leu Thr Arg Val Leu
        1395                    1400                    1405

TTC CAA GAC AAC TCT TCT CAT CTT CCA GCA GCA TCT TAT AGA AAG AAA    4272
Phe Gln Asp Asn Ser Ser His Leu Pro Ala Ala Ser Tyr Arg Lys Lys
        1410                    1415                    1420

GAT TCT GGG GTC CAA GAA AGC AGT CAT TTC TTA CAA GGA GCC AAA AAA    4320
Asp Ser Gly Val Gln Glu Ser Ser His Phe Leu Gln Gly Ala Lys Lys
1425                    1430                    1435            1440

AAT AAC CTT TCT TTA GCC ATT CTA ACC TTG GAG ATG ACT GGT GAT CAA    4368
Asn Asn Leu Ser Leu Ala Ile Leu Thr Leu Glu Met Thr Gly Asp Gln
                1445                    1450                    1455

AGA GAG GTT GGC TCC CTG GGG ACA AGT GCC ACA AAT TCA GTC ACA TAC    4416
Arg Glu Val Gly Ser Leu Gly Thr Ser Ala Thr Asn Ser Val Thr Tyr
                1460                    1465                    1470

AAG AAA GTT GAG AAC ACT GTT CTC CCG AAA CCA GAC TTG CCC AAA ACA    4464
Lys Lys Val Glu Asn Thr Val Leu Pro Lys Pro Asp Leu Pro Lys Thr
                1475                    1480                    1485

TCT GGC AAA GTT GAA TTG CTT CCA AAA GTT CAC ATT TAT CAG AAG GAC    4512
Ser Gly Lys Val Glu Leu Leu Pro Lys Val His Ile Tyr Gln Lys Asp
        1490                    1495                    1500

CTA TTC CCT ACG GAA ACT AGC AAT GGG TCT CCT GGC CAT CTG GAT CTC    4560
Leu Phe Pro Thr Glu Thr Ser Asn Gly Ser Pro Gly His Leu Asp Leu
1505                    1510                    1515            1520

GTG GAA GGG AGC CTT CTT CAG GGA ACA GAG GGA GCG ATT AAG TGG AAT    4608
Val Glu Gly Ser Leu Leu Gln Gly Thr Glu Gly Ala Ile Lys Trp Asn
                        1525                    1530                    1535

GAA GCA AAC AGA CCT GGA AAA GTT CCC TTT CTG AGA GTA GCA ACA GAA    4656
Glu Ala Asn Arg Pro Gly Lys Val Pro Phe Leu Arg Val Ala Thr Glu
                1540                    1545                    1550

AGC TCT GCA AAG ACT CCC TCC AAG CTA TTG GAT CCT CTT GCT TGG GAT    4704
Ser Ser Ala Lys Thr Pro Ser Lys Leu Leu Asp Pro Leu Ala Trp Asp
        1555                    1560                    1565

AAC CAC TAT GGT ACT CAG ATA CCA AAA GAA GAG TGG AAA TCC CAA GAG    4752
Asn His Tyr Gly Thr Gln Ile Pro Lys Glu Glu Trp Lys Ser Gln Glu
        1570                    1575                    1580

AAG TCA CCA GAA AAA ACA GCT TTT AAG AAA AAG GAT ACC ATT TTG TCC    4800
Lys Ser Pro Glu Lys Thr Ala Phe Lys Lys Lys Asp Thr Ile Leu Ser
1585                    1590                    1595            1600

CTG AAC GCT TGT GAA AGC AAT CAT GCA ATA GCA GCA ATA AAT GAG GGA    4848
Leu Asn Ala Cys Glu Ser Asn His Ala Ile Ala Ala Ile Asn Glu Gly
                        1605                    1610                    1615

CAA AAT AAG CCC GAA ATA GAA GTC ACC TGG GCA AAG CAA GGT AGG ACT    4896
Gln Asn Lys Pro Glu Ile Glu Val Thr Trp Ala Lys Gln Gly Arg Thr
                1620                    1625                    1630

GAA AGG CTG TGC TCT CAA AAC CCA CCA GTC TTG AAA CGC CAT CAA CGG    4944
Glu Arg Leu Cys Ser Gln Asn Pro Pro Val Leu Lys Arg His Gln Arg
        1635                    1640                    1645

GAA ATA ACT CGT ACT ACT CTT CAG TCA GAT CAA GAG GAA ATT GAC TAT    4992
Glu Ile Thr Arg Thr Thr Leu Gln Ser Asp Gln Glu Glu Ile Asp Tyr
        1650                    1655                    1660

GAT GAT ACC ATA TCA GTT GAA ATG AAG AAG GAA GAT TTT GAC ATT TAT    5040
Asp Asp Thr Ile Ser Val Glu Met Lys Lys Glu Asp Phe Asp Ile Tyr
1665                    1670                    1675            1680

GAT GAG GAT GAA AAT CAG AGC CCC CGC AGC TTT CAA AAG AAA ACA CGA    5088
Asp Glu Asp Glu Asn Gln Ser Pro Arg Ser Phe Gln Lys Lys Thr Arg
                        1685                    1690                    1695
```

```
CAC TAT TTT ATT GCT GCA GTG GAG AGG CTC TGG GAT TAT GGG ATG AGT        5136
His Tyr Phe Ile Ala Ala Val Glu Arg Leu Trp Asp Tyr Gly Met Ser
        1700                1705                1710

AGC TCC CCA CAT GTT CTA AGA AAC AGG GCT CAG AGT GGC AGT GTC CCT        5184
Ser Ser Pro His Val Leu Arg Asn Arg Ala Gln Ser Gly Ser Val Pro
        1715                1720                1725

CAG TTC AAG AAA GTT GTT TTC CAG GAA TTT ACT GAT GGC TCC TTT ACT        5232
Gln Phe Lys Lys Val Val Phe Gln Glu Phe Thr Asp Gly Ser Phe Thr
        1730                1735                1740

CAG CCC TTA TAC CGT GGA GAA CTA AAT GAA CAT TTG GGA CTC CTG GGG        5280
Gln Pro Leu Tyr Arg Gly Glu Leu Asn Glu His Leu Gly Leu Leu Gly
1745                1750                1755                1760

CCA TAT ATA AGA GCA GAA GTT GAA GAT AAT ATC ATG GTA ACT TTC AGA        5328
Pro Tyr Ile Arg Ala Glu Val Glu Asp Asn Ile Met Val Thr Phe Arg
                1765                1770                1775

AAT CAG GCC TCT CGT CCC TAT TCC TTC TAT TCT AGC CTT ATT TCT TAT        5376
Asn Gln Ala Ser Arg Pro Tyr Ser Phe Tyr Ser Ser Leu Ile Ser Tyr
                1780                1785                1790

GAG GAA GAT CAG AGG CAA GGA GCA GAA CCT AGA AAA AAC TTT GTC AAG        5424
Glu Glu Asp Gln Arg Gln Gly Ala Glu Pro Arg Lys Asn Phe Val Lys
        1795                1800                1805

CCT AAT GAA ACC AAA ACT TAC TTT TGG AAA GTG CAA CAT CAT ATG GCA        5472
Pro Asn Glu Thr Lys Thr Tyr Phe Trp Lys Val Gln His His Met Ala
1810                1815                1820

CCC ACT AAA GAT GAG TTT GAC TGC AAA GCC TGG GCT TAT TTC TCT GAT        5520
Pro Thr Lys Asp Glu Phe Asp Cys Lys Ala Trp Ala Tyr Phe Ser Asp
1825                1830                1835                1840

GTT GAC CTG GAA AAA GAT GTG CAC TCA GGC CTG ATT GGA CCC CTT CTG        5568
Val Asp Leu Glu Lys Asp Val His Ser Gly Leu Ile Gly Pro Leu Leu
                1845                1850                1855

GTC TGC CAC ACT AAC ACA CTG AAC CCT GCT CAT GGG AGA CAA GTG ACA        5616
Val Cys His Thr Asn Thr Leu Asn Pro Ala His Gly Arg Gln Val Thr
                1860                1865                1870

GTA CAG GAA TTT GCT CTG TTT TTC ACC ATC TTT GAT GAG ACC AAA AGC        5664
Val Gln Glu Phe Ala Leu Phe Phe Thr Ile Phe Asp Glu Thr Lys Ser
        1875                1880                1885

TGG TAC TTC ACT GAA AAT ATG GAA AGA AAC TGC AGG GCT CCC TGC AAT        5712
Trp Tyr Phe Thr Glu Asn Met Glu Arg Asn Cys Arg Ala Pro Cys Asn
1890                1895                1900

ATC CAG ATG GAA GAT CCC ACT TTT AAA GAG AAT TAT CGC TTC CAT GCA        5760
Ile Gln Met Glu Asp Pro Thr Phe Lys Glu Asn Tyr Arg Phe His Ala
1905                1910                1915                1920

ATC AAT GGC TAC ATA ATG GAT ACA CTA CCT GGC TTA GTA ATG GCT CAG        5808
Ile Asn Gly Tyr Ile Met Asp Thr Leu Pro Gly Leu Val Met Ala Gln
                1925                1930                1935

GAT CAA AGG ATT CGA TGG TAT CTG CTC AGC ATG GGC AGC AAT GAA AAC        5856
Asp Gln Arg Ile Arg Trp Tyr Leu Leu Ser Met Gly Ser Asn Glu Asn
                1940                1945                1950

ATC CAT TCT ATT CAT TTC AGT GGA CAT GTG TTC ACT GTA CGA AAA AAA        5904
Ile His Ser Ile His Phe Ser Gly His Val Phe Thr Val Arg Lys Lys
        1955                1960                1965

GAG GAG TAT AAA ATG GCA CTG TAC AAT CTC TAT CCA GGT GTT TTT GAG        5952
Glu Glu Tyr Lys Met Ala Leu Tyr Asn Leu Tyr Pro Gly Val Phe Glu
        1970                1975                1980

ACA GTG GAA ATG TTA CCA TCC AAA GCT GGA ATT TGG CGG GTG GAA TGC        6000
Thr Val Glu Met Leu Pro Ser Lys Ala Gly Ile Trp Arg Val Glu Cys
1985                1990                1995                2000

CTT ATT GGC GAG CAT CTA CAT GCT GGG ATG AGC ACA CTT TTT CTG GTG        6048
Leu Ile Gly Glu His Leu His Ala Gly Met Ser Thr Leu Phe Leu Val
                2005                2010                2015
```

```
TAC AGC AAT AAG TGT CAG ACT CCC CTG GGA ATG GCT TCT GGA CAC ATT      6096
Tyr Ser Asn Lys Cys Gln Thr Pro Leu Gly Met Ala Ser Gly His Ile
            2020            2025            2030

AGA GAT TTT CAG ATT ACA GCT TCA GGA CAA TAT GGA CAG TGG GCC CCA      6144
Arg Asp Phe Gln Ile Thr Ala Ser Gly Gln Tyr Gly Gln Trp Ala Pro
        2035            2040            2045

AAG CTG GCC AGA CTT CAT TAT TCC GGA TCA ATC AAT GCC TGG ACG ACC      6192
Lys Leu Ala Arg Leu His Tyr Ser Gly Ser Ile Asn Ala Trp Thr Thr
2050            2055            2060

AAG GAG CCC TTT TCT TGG ATC AAG GTG GAT CTG TTG GCA CCA ATG ATT      6240
Lys Glu Pro Phe Ser Trp Ile Lys Val Asp Leu Leu Ala Pro Met Ile
2065            2070            2075            2080

ATT CAC GGC ATC AAG ACC CAG GGT GCC CGT CAG AAG TTC TCC AGC CTC      6288
Ile His Gly Ile Lys Thr Gln Gly Ala Arg Gln Lys Phe Ser Ser Leu
            2085            2090            2095

TAC ATC TCT CAG TTT ATC ATC ATG TAT AGT CTT GAT GGG AAG AAG TGG      6336
Tyr Ile Ser Gln Phe Ile Ile Met Tyr Ser Leu Asp Gly Lys Lys Trp
        2100            2105            2110

CAG ACT TAT CGA GGA AAT TCC ACT GGA ACC TTA ATG GTC TTC TTT GGC      6384
Gln Thr Tyr Arg Gly Asn Ser Thr Gly Thr Leu Met Val Phe Phe Gly
        2115            2120            2125

AAT GTG GAT TCA TCT GGG ATA AAA CAC AAT ATT TTT AAC CCT CCA ATT      6432
Asn Val Asp Ser Ser Gly Ile Lys His Asn Ile Phe Asn Pro Pro Ile
        2130            2135            2140

ATT GCT CGA TAC ATC CGT TTG CAC CCA ACT CAT TAT AGC ATT CGC AGC      6480
Ile Ala Arg Tyr Ile Arg Leu His Pro Thr His Tyr Ser Ile Arg Ser
2145            2150            2155            2160

ACT CTT CGC ATG GAG TTG ATG GGC TGT GAT TTA AAT AGT TGC AGC ATG      6528
Thr Leu Arg Met Glu Leu Met Gly Cys Asp Leu Asn Ser Cys Ser Met
            2165            2170            2175

CCA TTG GGA ATG GAG AGT AAA GCA ATA TCA GAT GCA CAG ATT ACT GCT      6576
Pro Leu Gly Met Glu Ser Lys Ala Ile Ser Asp Ala Gln Ile Thr Ala
        2180            2185            2190

TCA TCC TAC TTT ACC AAT ATG TTT GCC ACC TGG TCT CCT TCA AAA GCT      6624
Ser Ser Tyr Phe Thr Asn Met Phe Ala Thr Trp Ser Pro Ser Lys Ala
        2195            2200            2205

CGA CTT CAC CTC CAA GGG AGG AGT AAT GCC TGG AGA CCT CAG GTG AAT      6672
Arg Leu His Leu Gln Gly Arg Ser Asn Ala Trp Arg Pro Gln Val Asn
2210            2215            2220

AAT CCA AAA GAG TGG CTG CAA GTG GAC TTC CAG AAG ACA ATG AAA GTC      6720
Asn Pro Lys Glu Trp Leu Gln Val Asp Phe Gln Lys Thr Met Lys Val
2225            2230            2235            2240

ACA GGA GTA ACT ACT CAG GGA GTA AAA TCT CTG CTT ACC AGC ATG TAT      6768
Thr Gly Val Thr Thr Gln Gly Val Lys Ser Leu Leu Thr Ser Met Tyr
            2245            2250            2255

GTG AAG GAG TTC CTC ATC TCC AGC AGT CAA GAT GGC CAT CAG TGG ACT      6816
Val Lys Glu Phe Leu Ile Ser Ser Ser Gln Asp Gly His Gln Trp Thr
        2260            2265            2270

CTC TTT TTT CAG AAT GGC AAA GTA AAG GTT TTT CAG GGA AAT CAA GAC      6864
Leu Phe Phe Gln Asn Gly Lys Val Lys Val Phe Gln Gly Asn Gln Asp
        2275            2280            2285

TCC TTC ACA CCT GTG GTG AAC TCT CTA GAC CCA CCG TTA CTG ACT CGC      6912
Ser Phe Thr Pro Val Val Asn Ser Leu Asp Pro Pro Leu Leu Thr Arg
        2290            2295            2300

TAC CTT CGA ATT CAC CCC CAG AGT TGG GTG CAC CAG ATT GCC CTG AGG      6960
Tyr Leu Arg Ile His Pro Gln Ser Trp Val His Gln Ile Ala Leu Arg
2305            2310            2315            2320

ATG GAG GTT CTG GGC TGC GAG GCA CAG GAC CTC TAC TGA                  6999
Met Glu Val Leu Gly Cys Glu Ala Gln Asp Leu Tyr
            2325            2330
```

( 2 ) INFORMATION FOR SEQ ID NO:2:

( i ) SEQUENCE CHARACTERISTICS:
        ( A ) LENGTH: 2332 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ala Thr Arg Arg Tyr Tyr Leu Gly Ala Val Glu Leu Ser Trp Asp Tyr
 1               5                  10                  15
Met Gln Ser Asp Leu Gly Glu Leu Pro Val Asp Ala Arg Phe Pro Pro
             20                  25                  30
Arg Val Pro Lys Ser Phe Pro Phe Asn Thr Ser Val Val Tyr Lys Lys
         35                  40                  45
Thr Leu Phe Val Glu Phe Thr Asp His Leu Phe Asn Ile Ala Lys Pro
     50                  55                  60
Arg Pro Pro Trp Met Gly Leu Leu Gly Pro Thr Ile Gln Ala Glu Val
 65                  70                  75                  80
Tyr Asp Thr Val Val Ile Thr Leu Lys Asn Met Ala Ser His Pro Val
                 85                  90                  95
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
        115                 120                 125
Phe Pro Gly Gly Ser His Thr Tyr Val Trp Gln Val Leu Lys Glu Asn
    130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
```

```
Ile Gln Ile Arg Ser Val Ala Lys Lys His Pro Lys Thr Trp Val His
    370             375                 380
Tyr Ile Ala Ala Glu Glu Glu Asp Trp Asp Tyr Ala Pro Leu Val Leu
385             390                 395                         400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
            515                 520                 525
Leu Thr Arg Tyr Tyr Ser Ser Phe Val Asn Met Glu Arg Asp Leu Ala
    530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
    595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
    675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Arg Ser Thr Arg
            740                 745                 750
Gln Lys Gln Phe Asn Ala Thr Thr Ile Pro Glu Asn Asp Ile Glu Lys
    755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
```

```
                785                    790                    795                    800
           His Gly Leu Ser Leu Ser Asp Leu Gln Glu Ala Lys Tyr Glu Thr Phe
                           805                    810                815
           Ser Asp Asp Pro Ser Pro Gly Ala Ile Asp Ser Asn Asn Ser Leu Ser
                           820                    825                830
           Glu Met Thr His Phe Arg Pro Gln Leu His His Ser Gly Asp Met Val
                           835                    840                845
           Phe Thr Pro Glu Ser Gly Leu Gln Leu Arg Leu Asn Glu Lys Leu Gly
                           850                    855                860
           Thr Thr Ala Ala Thr Glu Leu Lys Lys Leu Asp Phe Lys Val Ser Ser
           865                    870                    875                    880
           Thr Ser Asn Asn Leu Ile Ser Thr Ile Pro Ser Asp Asn Leu Ala Ala
                           885                    890                895
           Gly Thr Asp Asn Thr Ser Ser Leu Gly Pro Pro Ser Met Pro Val His
                           900                    905                910
           Tyr Asp Ser Gln Leu Asp Thr Thr Leu Phe Gly Lys Lys Ser Ser Pro
                           915                    920                925
           Leu Thr Glu Ser Gly Gly Pro Leu Ser Leu Ser Glu Glu Asn Asn Asp
               930                    935                    940
           Ser Lys Leu Leu Glu Ser Gly Leu Met Asn Ser Gln Glu Ser Ser Trp
           945                    950                    955                    960
           Gly Lys Asn Val Ser Ser Thr Glu Ser Gly Arg Leu Phe Lys Gly Lys
                           965                    970                975
           Arg Ala His Gly Pro Ala Leu Leu Thr Lys Asp Asn Ala Leu Phe Lys
                           980                    985                990
           Val Ser Ile Ser Leu Leu Lys Thr Asn Lys Thr Ser Asn Asn Ser Ala
                           995                    1000               1005
           Thr Asn Arg Lys Thr His Ile Asp Gly Pro Ser Leu Leu Ile Glu Asn
               1010                   1015                   1020
           Ser Pro Ser Val Trp Gln Asn Ile Leu Glu Ser Asp Thr Glu Phe Lys
           1025                   1030                   1035                   1040
           Lys Val Thr Pro Leu Ile His Asp Arg Met Leu Met Asp Lys Asn Ala
                           1045                   1050               1055
           Thr Ala Leu Arg Leu Asn His Met Ser Asn Lys Thr Thr Ser Ser Lys
                           1060                   1065               1070
           Asn Met Glu Met Val Gln Gln Lys Lys Glu Gly Pro Ile Pro Pro Asp
                           1075                   1080               1085
           Ala Gln Asn Pro Asp Met Ser Phe Phe Lys Met Leu Phe Leu Pro Glu
                           1090                   1095               1100
           Ser Ala Arg Trp Ile Gln Arg Thr His Gly Lys Asn Ser Leu Asn Ser
           1105                   1110                   1115                   1120
           Gly Gln Gly Pro Ser Pro Lys Gln Leu Val Ser Leu Gly Pro Glu Lys
                           1125                   1130               1135
           Ser Val Glu Gly Gln Asn Phe Leu Ser Glu Lys Asn Lys Val Val Val
                           1140                   1145               1150
           Arg Lys Gly Glu Phe Thr Lys Asp Val Gly Leu Lys Glu Met Val Phe
                           1155                   1160               1165
           Pro Ser Ser Arg Asn Leu Phe Leu Thr Asn Leu Asp Asn Leu His Glu
               1170                   1175                   1180
           Asn Asn Thr His Asn Gln Glu Lys Lys Ile Gln Glu Glu Ile Glu Lys
           1185                   1190                   1195                   1200
           Lys Glu Thr Leu Ile Gln Glu Asn Val Val Leu Pro Gln Ile His Thr
                           1205                   1210               1215
```

```
Val Thr Gly Thr Lys Asn Phe Met Lys Asn Leu Phe Leu Leu Ser Thr
         1220                1225                1230
Arg Gln Asn Val Glu Gly Ser Tyr Asp Gly Ala Tyr Ala Pro Val Leu
         1235                1240                1245
Gln Asp Phe Arg Ser Leu Asn Asp Ser Thr Asn Arg Thr Lys Lys His
         1250                1255                1260
Thr Ala His Phe Ser Lys Lys Gly Glu Glu Glu Asn Leu Glu Gly Leu
1265                1270                1275                1280
Gly Asn Gln Thr Lys Gln Ile Val Glu Lys Tyr Ala Cys Thr Thr Arg
             1285                1290                1295
Ile Ser Pro Asn Thr Ser Gln Gln Asn Phe Val Thr Gln Arg Ser Lys
         1300                1305                1310
Arg Ala Leu Lys Gln Phe Arg Leu Pro Leu Glu Glu Thr Glu Leu Glu
         1315                1320                1325
Lys Arg Ile Ile Val Asp Asp Thr Ser Thr Gln Trp Ser Lys Asn Met
         1330                1335                1340
Lys His Leu Thr Pro Ser Thr Leu Thr Gln Ile Asp Tyr Asn Glu Lys
1345                1350                1355                1360
Glu Lys Gly Ala Ile Thr Gln Ser Pro Leu Ser Asp Cys Leu Thr Arg
             1365                1370                1375
Ser His Ser Ile Pro Gln Ala Asn Arg Ser Pro Leu Pro Ile Ala Lys
         1380                1385                1390
Val Ser Ser Phe Pro Ser Ile Arg Pro Ile Tyr Leu Thr Arg Val Leu
         1395                1400                1405
Phe Gln Asp Asn Ser Ser His Leu Pro Ala Ala Ser Tyr Arg Lys Lys
         1410                1415                1420
Asp Ser Gly Val Gln Glu Ser Ser His Phe Leu Gln Gly Ala Lys Lys
1425                1430                1435                1440
Asn Asn Leu Ser Leu Ala Ile Leu Thr Leu Glu Met Thr Gly Asp Gln
             1445                1450                1455
Arg Glu Val Gly Ser Leu Gly Thr Ser Ala Thr Asn Ser Val Thr Tyr
         1460                1465                1470
Lys Lys Val Glu Asn Thr Val Leu Pro Lys Pro Asp Leu Pro Lys Thr
         1475                1480                1485
Ser Gly Lys Val Glu Leu Leu Pro Lys Val His Ile Tyr Gln Lys Asp
         1490                1495                1500
Leu Phe Pro Thr Glu Thr Ser Asn Gly Ser Pro Gly His Leu Asp Leu
1505                1510                1515                1520
Val Glu Gly Ser Leu Leu Gln Gly Thr Glu Gly Ala Ile Lys Trp Asn
             1525                1530                1535
Glu Ala Asn Arg Pro Gly Lys Val Pro Phe Leu Arg Val Ala Thr Glu
         1540                1545                1550
Ser Ser Ala Lys Thr Pro Ser Lys Leu Leu Asp Pro Leu Ala Trp Asp
         1555                1560                1565
Asn His Tyr Gly Thr Gln Ile Pro Lys Glu Glu Trp Lys Ser Gln Glu
         1570                1575                1580
Lys Ser Pro Glu Lys Thr Ala Phe Lys Lys Lys Asp Thr Ile Leu Ser
1585                1590                1595                1600
Leu Asn Ala Cys Glu Ser Asn His Ala Ile Ala Ala Ile Asn Glu Gly
             1605                1610                1615
Gln Asn Lys Pro Glu Ile Glu Val Thr Trp Ala Lys Gln Gly Arg Thr
         1620                1625                1630
Glu Arg Leu Cys Ser Gln Asn Pro Pro Val Leu Lys Arg His Gln Arg
         1635                1640                1645
```

Glu Ile Thr Arg Thr Thr Leu Gln Ser Asp Gln Glu Ile Asp Tyr
1650                    1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
            1685                1690                1695

His Tyr Phe Ile Ala Ala Val Glu Arg Leu Trp Asp Tyr Gly Met Ser
                1700                1705                1710

Ser Ser Pro His Val Leu Arg Asn Arg Ala Gln Ser Gly Ser Val Pro
            1715                1720                1725

Gln Phe Lys Lys Val Val Phe Gln Glu Phe Thr Asp Gly Ser Phe Thr
1730                    1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
                1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Arg Lys Asn Phe Val Lys
            1795                1800                1805

Pro Asn Glu Thr Lys Thr Tyr Phe Trp Lys Val Gln His His Met Ala
1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
                1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
            1875                1880                1885

Trp Tyr Phe Thr Glu Asn Met Glu Arg Asn Cys Arg Ala Pro Cys Asn
            1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
                1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
            1955                1960                1965

Glu Glu Tyr Lys Met Ala Leu Tyr Asn Leu Tyr Pro Gly Val Phe Glu
1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
                2005                2010                2015

Tyr Ser Asn Lys Cys Gln Thr Pro Leu Gly Met Ala Ser Gly His Ile
            2020                2025                2030

Arg Asp Phe Gln Ile Thr Ala Ser Gly Gln Tyr Gly Gln Trp Ala Pro
            2035                2040                2045

Lys Leu Ala Arg Leu His Tyr Ser Gly Ser Ile Asn Ala Trp Thr Thr
2050                2055                2060

Lys Glu Pro Phe Ser Trp Ile Lys Val Asp Leu Leu Ala Pro Met Ile

-continued

```
2065                    2070                    2075                    2080
Ile His Gly Ile Lys Thr Gln Gly Ala Arg Gln Lys Phe Ser Ser Leu
                2085                    2090                    2095
Tyr Ile Ser Gln Phe Ile Ile Met Tyr Ser Leu Asp Gly Lys Lys Trp
            2100                    2105                    2110
Gln Thr Tyr Arg Gly Asn Ser Thr Gly Thr Leu Met Val Phe Phe Gly
            2115                    2120                    2125
Asn Val Asp Ser Ser Gly Ile Lys His Asn Ile Phe Asn Pro Pro Ile
            2130                    2135                    2140
Ile Ala Arg Tyr Ile Arg Leu His Pro Thr His Tyr Ser Ile Arg Ser
2145                    2150                    2155                    2160
Thr Leu Arg Met Glu Leu Met Gly Cys Asp Leu Asn Ser Cys Ser Met
                2165                    2170                    2175
Pro Leu Gly Met Glu Ser Lys Ala Ile Ser Asp Ala Gln Ile Thr Ala
            2180                    2185                    2190
Ser Ser Tyr Phe Thr Asn Met Phe Ala Thr Trp Ser Pro Ser Lys Ala
            2195                    2200                    2205
Arg Leu His Leu Gln Gly Arg Ser Asn Ala Trp Arg Pro Gln Val Asn
2210                    2215                    2220
Asn Pro Lys Glu Trp Leu Gln Val Asp Phe Gln Lys Thr Met Lys Val
2225                    2230                    2235                    2240
Thr Gly Val Thr Thr Gln Gly Val Lys Ser Leu Leu Thr Ser Met Tyr
                2245                    2250                    2255
Val Lys Glu Phe Leu Ile Ser Ser Ser Gln Asp Gly His Gln Trp Thr
            2260                    2265                    2270
Leu Phe Phe Gln Asn Gly Lys Val Lys Val Phe Gln Gly Asn Gln Asp
        2275                    2280                    2285
Ser Phe Thr Pro Val Val Asn Ser Leu Asp Pro Pro Leu Leu Thr Arg
    2290                    2295                    2300
Tyr Leu Arg Ile His Pro Gln Ser Trp Val His Gln Ile Ala Leu Arg
2305                    2310                    2315                    2320
Met Glu Val Leu Gly Cys Glu Ala Gln Asp Leu Tyr
                2325                    2330
```

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AGAGATCTAG CTTCA    15

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCGGTCGACC CTCATCTTGG TTCAATGGCA    30

( 2 ) INFORMATION FOR SEQ ID NO:5:

( i ) SEQUENCE CHARACTERISTICS:

( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

ACTGGATCCA AGCTT                                                                              15

( 2 ) INFORMATION FOR SEQ ID NO:6:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

ACTAAAGCAG AATCG                                                                              15

( 2 ) INFORMATION FOR SEQ ID NO:7:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

GAAATAACTC GTACT                                                                              15

( 2 ) INFORMATION FOR SEQ ID NO:8:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

AGCTTTGGGG CCCAC                                                                              15

( 2 ) INFORMATION FOR SEQ ID NO:9:

( i ) SEQUENCE CHARACTERISTICS:
            ( A ) LENGTH: 31 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

CCCTCGAGCC ACCATGGAAA TAGAGCTCTC C                                                             31

( 2 ) INFORMATION FOR SEQ ID NO:10:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

CCGGTCGACC CTCATCTTGG TTCAATGGCA                                                               30

( 2 ) INFORMATION FOR SEQ ID NO:11:

( i ) SEQUENCE CHARACTERISTICS:
            ( A ) LENGTH: 12 base pairs
            ( B ) TYPE: nucleic acid (C) STRANDEDNESS: single
(D) TOPOLOGY: linear (xi) SEQUENCE DESCRIPTION: SEQ ID NO:11:

CCACCATGGT GG　　　　　　　　　　　　　　　　　　　　　　　　　　　12